United States Patent
Jenkins

(10) Patent No.: US 11,318,132 B2
(45) Date of Patent: May 3, 2022

(54) DIVERSION-RESISTANT OPIOID FORMULATIONS

(71) Applicant: Elysium Therapeutics, Inc., Danville, CA (US)

(72) Inventor: Thomas E. Jenkins, Half Moon Bay, CA (US)

(73) Assignee: Elysium Therapeutics, Inc., Akron, OH (US)

( * ) Notice: Subject to any disclaimer, the term of this patent is extended or adjusted under 35 U.S.C. 154(b) by 0 days.

(21) Appl. No.: 16/393,812

(22) Filed: Apr. 24, 2019

(65) Prior Publication Data

US 2020/0113893 A1   Apr. 16, 2020

Related U.S. Application Data

(62) Division of application No. 14/918,464, filed on Oct. 20, 2015, now Pat. No. 10,314,839.

(60) Provisional application No. 62/066,221, filed on Oct. 20, 2014.

(51) Int. Cl.
*A61K 31/485* (2006.01)
*A61K 45/06* (2006.01)
*A61K 9/48* (2006.01)
*A61K 47/60* (2017.01)
*A61K 47/55* (2017.01)

(52) U.S. Cl.
CPC .......... *A61K 31/485* (2013.01); *A61K 9/4866* (2013.01); *A61K 45/06* (2013.01); *A61K 47/55* (2017.08); *A61K 47/60* (2017.08)

(58) Field of Classification Search
CPC .................................................. A61K 31/485
See application file for complete search history.

(56) References Cited

U.S. PATENT DOCUMENTS

| 5,159,081 A | 10/1992 | Cantrell et al. |
| 5,250,542 A | 10/1993 | Cantrell et al. |
| 5,270,328 A | 12/1993 | Cantrell et al. |
| 5,434,171 A | 7/1995 | Frank et al. |

(Continued)

FOREIGN PATENT DOCUMENTS

| WO | WO-9745442 A1 | 12/1997 |
| WO | WO-2008101187 A2 | 8/2008 |

(Continued)

OTHER PUBLICATIONS

International search report and written opinion dated Jan. 22, 2016 for PCT/US2015/056514.

(Continued)

*Primary Examiner* — Benjamin J Packard
(74) *Attorney, Agent, or Firm* — Wilson Sonsini Goodrich & Rosati

(57) ABSTRACT

The present invention provides a composition comprising an opioid agonist, and a polymer-antagonist conjugate. The polymer-antagonist conjugate preferably does not hydrolyze upon administration to a patient, and does not bind to the opioid receptors. The covalent bond between the polymer and the antagonist in the conjugate is broken over a defined period of time to release the antagonist into the formulation. The released antagonist attenuates the liking of the agonist, thereby eliminating the incentive to the diversion of the medicines.

24 Claims, 4 Drawing Sheets

(56) References Cited

U.S. PATENT DOCUMENTS

| | | |
|---|---|---|
| 6,228,863 B1 | 5/2001 | Palermo et al. |
| 6,375,957 B1 | 4/2002 | Kaiko et al. |
| 7,338,939 B2 | 3/2008 | Mickle et al. |
| 7,375,082 B2 | 5/2008 | Mickle et al. |
| 7,662,365 B2 | 2/2010 | Bentley et al. |
| 8,101,661 B2 | 1/2012 | Mickle |
| 8,133,881 B2 | 3/2012 | Mickle et al. |
| 8,217,005 B2 | 7/2012 | Jenkins et al. |
| 9,040,032 B2 | 5/2015 | Jenkins et al. |
| 10,314,839 B2 | 6/2019 | Jenkins |
| 2003/0124086 A1* | 7/2003 | Bentley .................. A61P 25/04 424/78.17 |
| 2006/0105046 A1 | 5/2006 | Bentley et al. |
| 2008/0026052 A1 | 1/2008 | Schoenhard |
| 2009/0287005 A1 | 11/2009 | Baker, Jr. et al. |
| 2010/0144645 A1 | 6/2010 | Kirk et al. |
| 2010/0305147 A1 | 12/2010 | Bentley et al. |
| 2011/0262359 A1 | 10/2011 | Jenkins et al. |
| 2011/0262360 A1 | 10/2011 | Jenkins et al. |
| 2011/0281886 A1 | 11/2011 | Jenkins et al. |
| 2012/0142718 A1 | 6/2012 | Jenkins et al. |
| 2012/0178773 A1 | 7/2012 | Jenkins et al. |
| 2016/0136153 A1 | 5/2016 | Jenkins |

FOREIGN PATENT DOCUMENTS

| | | |
|---|---|---|
| WO | WO-2011002991 A1 | 1/2011 |
| WO | WO-2011002995 A1 | 1/2011 |

OTHER PUBLICATIONS

Office action dated May 24, 2017 for U.S. Appl. No. 14/918,464.
Office action dated Dec. 21, 2016 for U.S. Appl. No. 14/918,464.
Pittelkow, et al. Selective synthesis of carbamate protected polyamines using alkyl phenyl carbonates. Synthesis. 2002; (15):2195-2202.
U.S. Appl. No. 14/918,464 Office Action dated Oct. 25, 2018.
U.S. Appl. No. 14/918,464 Office Action dated Feb. 23, 2018.
U.S. Appl. No. 14/918,464 Notice of Allowance dated Jan. 24, 2019.
Verschoyle, et al. British J. Cancer, 1999, 80, Suppl. 2, 96. Poster Presentations.

* cited by examiner

DIVERSION-RESISTANT OPIOID FORMULATIONS

CROSS-REFERENCE

This application is a division of U.S. patent application Ser. No. 14/918,464, filed Oct. 20, 2015, now U.S. Pat. No. 10,314,839; which claims the benefit of U.S. Provisional Application Ser. No. 62/066,221, filed on Oct. 20, 2014; all of which are incorporated herein by reference in their entirety and to which applications we claim priority under 35 USC § 120.

STATEMENT AS TO FEDERALLY SPONSORED RESEARCH

This invention was made with the support of the United States government under SBIR Grant number 1R44DA037908 by the National Institute on Drug Abuse (NIDA), one of the National Institutes of Health (NIH) in the U.S. Department of Health and Human Services.

TECHNICAL FIELD

The present invention relates to an opioid agonist and antagonist containing composition. More particularly, the present invention is directed to an opioid composition wherein the antagonist is covalently linked to a high molecular weight polymer, and the antagonist is released over a period of time thereby providing resistance to abuse and diversion of the medicament.

BACKGROUND

The class of drugs exhibiting opium or morphine-like properties is referred to as opioid agonists, or opioids, and they interact with opioid receptors in the brain, the peripheral nervous system and other tissues. The three major opioid receptor subtypes are mu, delta, and kappa. Each of these receptors has a unique anatomical distribution in the central nervous system, the peripheral nervous system and the gastrointestinal tract. Most of the clinically used opioids exert their desired therapeutic action (i.e. analgesia) at the mu receptor subtype.

Opioids include morphine, codeine, oxycodone, hydrocodone, hydromorphone, and the like. Examples of marketed opioids in the United States include OxyContin®, Vicodin®, and Percocet®. The opioids have diverse effects, including analgesia, euphoria, drowsiness, changes in mood and alterations of the endocrine and autonomic nervous systems. Opioid analgesics comprise the major class of drugs used in the management of moderate to severe pain. As a class, opioids are among the most prescribed drugs in the US. IMS data shows that about 9 billion hydrocodone containing pills are prescribed annually.

One of the major concerns with the prescription of opioids is the diversion of the drugs for non-prescribed use. It has been found that unused prescription opioid drugs are frequently diverted to people who misuse or abuse them without prescriptions. More than three out of four people who misuse prescription painkillers use drugs previously prescribed to someone else. For example, among new abusers who began to misuse pain relievers in the past year, 68 percent obtained their pills from a friend or relative, while only 9 percent purchased their pills from a friend, dealer, or over the internet. Strategies aimed at reducing the diversion of the vast surplus of unused prescription opioids are currently limited to programs aimed at encouraging people to "responsibly and appropriately" dispose of their leftover prescriptions. However, only a small percentage of unused opioid prescriptions are disposed of responsibly and appropriately because patients often reserve surplus pills for self-medication or recreational abuse. A critical aspect enabling the widespread issue of opioid diversion relates to the fact that the potency of prescription opioids diminishes very little over time. The long half-life of unused prescription opioids enables them to be stored, diverted, and abused almost indefinitely.

SUMMARY OF THE INVENTION

In some instances, the disclosure provides a composition, the composition comprising: an opioid agonist; and a compound comprising formula I, $(D-X-Z)_m-P(I)$, wherein D is an opioid antagonist; X is a labile functionality capable of being hydrolyzed or fragmented to release D under controlled conditions; Z is a covalent linkage between X and the polymer; P is a polymer; and m is an integer selected to be between 1 and 100,000.

In some embodiments, the disclosure provides a method for providing analgesia to a subject in need thereof, the method comprising administrating to the subject a dose unit form comprising: i) an opioid agonist; and ii) a opioid antagonist-polymer conjugate; wherein the opioid antagonist-polymer conjugate provides an opioid antagonist at a rate that limits the therapeutically-effective plasma level of the opioid agonist to a first period of time.

In some embodiments, the disclosure provides, a softgel capsule comprising a sheath enclosing a liquid fill, the fill comprising: an effective amount of an opioid agonist; a opioid antagonist-polymer conjugate; a pharmaceutically acceptable liquid carrier; and a reactive agent capable of hydrolyzing the opioid antagonist-polymer conjugate.

In some embodiments, the disclosure provides a dose unit form for use in treating a condition, wherein the dose unit form comprises: i) an opioid agonist; ii) a polymer-opioid antagonist conjugate, wherein the polymer-opioid antagonist liberates, releases, or hydrolyses an amount of an opioid antagonist over a period of time.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
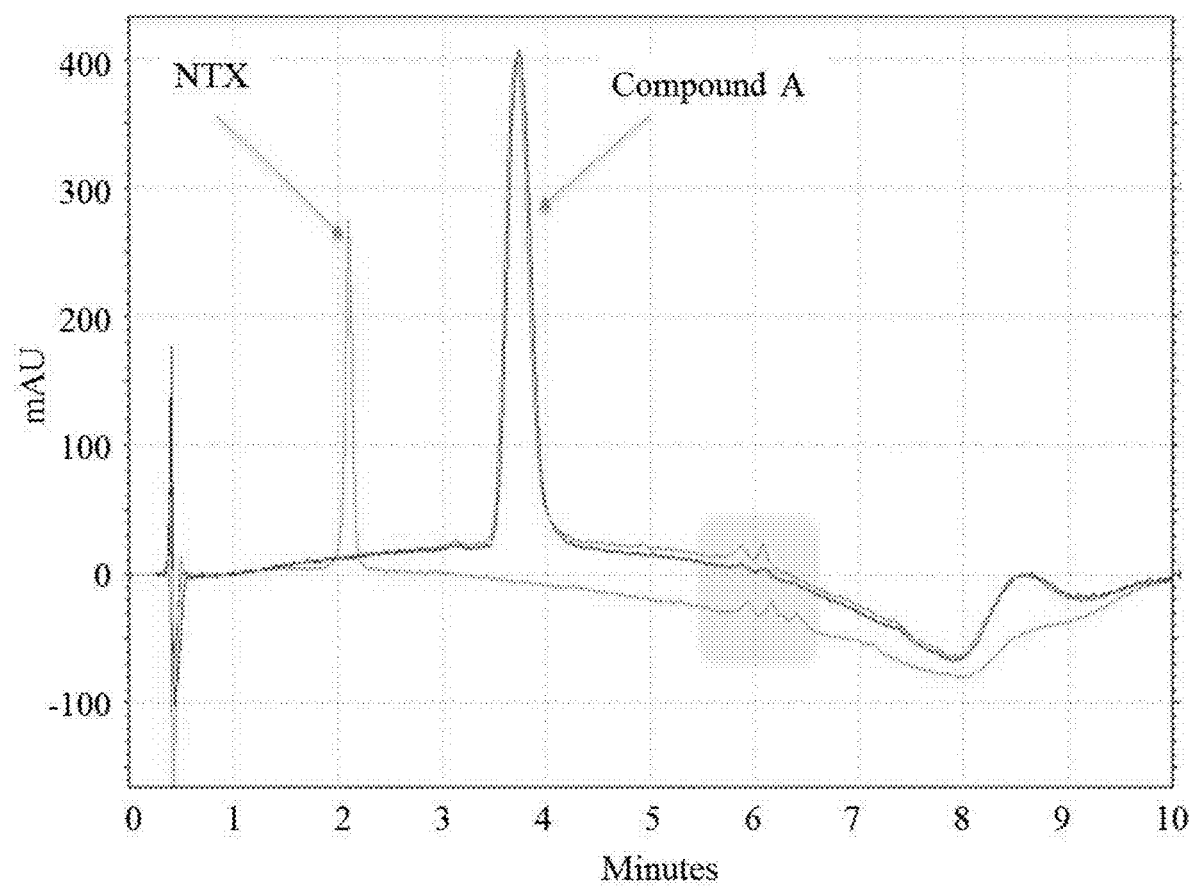
FIG. 1 illustrates the analytical HPLC data for Compound A.2TFA salt immediately following purification (black) and after several months of storage under ambient conditions (blue).

The present invention discloses a composition that significantly reduces the diversion of prescription opioid medicines. The disclosure describes novel opioid antagonist-polymer conjugates that can deactivate an opioid agonist-containing formulation over a well-defined period of time.

Previously, some attempts have been made to combine fixed ratios of opioid agonist and antagonists in order to provide dosage forms that are tamper- or abuse-resistant, or to mitigate the undesirable side-effects of opioid agonists. Existing human data suggests that a formulation containing a fixed ratio formulation of an opioid agonist and an opioid antagonist (i) does not effectively deters abuse and diversion, and (ii) does not provide fully effective analgesia to patients suffering from pain. U.S. Pat. No. 6,228,863 to Palermo et al. teaches the reduction of the abuse potential of oral dosage forms of opioid analgesics by combining naloxone, an opioid antagonist, with an opioid agonist where the antagonist cannot be easily extracted from the agonist. The antagonist is in such a concentration that the combination will cause an aversive effect in a physically dependent human subject but not in a naive individual. U.S. Pat. No. 6,375,957 to Kaiko et al. describes static or fixed combinations of opioid agonist, NSAID or acetaminophen, and an orally active opioid antagonist that may reduce the abuse potential of an opioid analgesic when abused by opioid tolerant individuals. U.S. Pat. No. 7,662,365 to Bentley et al. describes a formulation containing a low molecular weight PEG-naloxone conjugate and an opioid agonist, whereby the PEG-naloxone conjugate is hydrolytically stable, active in the peripheral nervous system, and does not cross the blood-brain barrier.

Clearly there is a need for a delivery system for commonly used oral dosage formulations of drugs, and in particular, analgesics such as opioid analgesics, that provides (i) adequate analgesia to patients in pain, and (ii) significantly deters abuse and diversion. The present invention effectively addresses these needs. Compositions and formulations of the invention (i) provide effective analgesia to patients during a prescribed time interval, and (ii) markedly reduce diversion of unused pills by having them irreversibly auto-deactivate (i.e. lose opioid agonist potency) over a defined time period.

The present invention provides a composition comprising an opioid agonist and a polymer-antagonist conjugate. In some embodiments, the opioid antagonist-polymer conjugate does not hydrolyze upon oral administration to a patient, and does not bind to opioid receptors. The covalent bond between the polymer and the antagonist is broken over a defined period of time to release orally bioavailable, antagonist molecules within the dosage form. After the time required for manufacturing, dispensation to, and appropriate use by the patient has lapsed, the increasing concentration of the opioid antagonist released from the opioid antagonist-polymer conjugate within the unit dosage form at first attenuates (i.e., reduces), then ultimately ablates the effects of the opioid agonist. In contrast to formulations that provide fixed ratios of bioavailable antagonist co-formulated with an opioid agonist, patients will benefit from analgesic potency during the prescribed use period of their opioid agonist that is essentially unmitigated by the very small fraction of released antagonist. Experienced opioid abusers can become wary of abusing compositions, softgel capsules, and pills of the invention as the increasing dose of released antagonist may be sufficient to induce rapid and severe withdrawal symptoms. These aspects of the invention provide abuse-deterrence, and effectively reduce the potential for diversion.

In one aspect, the disclosure provides a self-expiring drug, wherein the drug is encapsulated in a capsule, wherein the drug is available to provide an analgesic effect to a subject up to about 2 years of being manufactured.

In one aspect of the invention, a composition is provided where the composition comprises an opioid agonist and an opioid antagonist-polymer conjugate compound comprising formula I:

$$(D-X-Z)_m-P \quad (I)$$

wherein D is an opioid antagonist; X is a labile functionality capable of being hydrolyzed or fragmented to release D under controlled conditions; Z is a covalent linkage between X and the polymer; P is a polymer; and m is an integer selected to be between 1 and 100,000.

In yet another aspect of the invention, a softgel capsule comprising a sheath enclosing a liquid fill is provided where the fill comprises an effective amount of an opioid agonist; a opioid antagonist-polymer conjugate; a pharmaceutically acceptable liquid carrier; and an optional reactive agent capable of hydrolyzing the opioid antagonist-polymer conjugate to release the monomeric antagonist.

Definitions

Unless otherwise stated, the following terms used in this application, including the specification and claims, have the definitions given below. Definition of standard chemistry terms may be found in reference works, including Carey and Sundberg (2004) "Advanced Organic Chemistry 4rd Ed." Vols. A and B, Springer, New York. The practice of the present invention will employ, unless otherwise indicated, conventional methods of mass spectroscopy, protein chemistry, biochemistry, synthetic organic chemistry, and pharmacology, within the skill of the art.

The term "modulator" means a molecule that interacts with a target. The interactions include, but are not limited to, agonism, antagonism, and the like, as defined herein.

The term "agonist" means a molecule such as a compound, a drug, an enzyme activator or a hormone that enhances the activity of another molecule or the activity of the target receptor.

The term "antagonist" means a molecule such as a compound, a drug, an enzyme inhibitor, or a hormone, that diminishes or prevents the action of another molecule or the activity of the target receptor.

The term "alkyl" means the monovalent branched or unbranched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, butyl, isobutyl, sec-butyl, tert-butyl, pentyl, n-hexyl, octyl, dodecyl, and the like.

The term "alkylene" as used herein means the divalent linear or branched saturated hydrocarbon radical, consisting solely of carbon and hydrogen atoms, having from one to eight carbon atoms inclusive, unless otherwise indicated. Examples of alkylene radicals include, but are not limited to, methylene, ethylene, trimethylene, propylene, tetramethylene, pentamethylene, ethylethylene, and the like.

The term "alkenylene" means the divalent linear or branched unsaturated hydrocarbon radical, containing at least one double bond and having from two to eight carbon atoms inclusive, unless otherwise indicated. The alkenylene radical includes the cis or trans ((E) or (Z)) isomeric groups or mixtures thereof generated by the asymmetric carbons. Examples of alkenylene radicals include, but are not limited to ethenylene, 2-propenylene, 1-propenylene, 2-butenyl, 2-pentenylene, and the like.

The term "aryl" means the monovalent monocyclic aromatic hydrocarbon radical consisting of one or more fused rings in which at least one ring is aromatic in nature, which can optionally be substituted with hydroxy, cyano, lower alkyl, lower alkoxy, thioalkyl, halogen, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl radicals include, but are not limited to, phenyl, naphthyl, biphenyl, indanyl, anthraquinolyl, and the like.

The term "halogen" as used herein refers to fluoro, bromo, chloro and/or iodo.

The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system.

As used herein, the terms "treat" or "treatment" are used interchangeably and are meant to indicate a postponement of development of diseases and/or a reduction in the severity and/or duration of such symptoms that will or are expected to develop. The terms further include ameliorating existing symptoms, and ameliorating the underlying symptoms.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

The term "pharmaceutically acceptable salt" of a compound means a salt that is pharmaceutically acceptable and that possesses the desired pharmacological activity of the parent compound. Such salts, for example, include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "opioid" means a substance, whether agonist, antagonist, or mixed agonist-antagonist, that interacts with one or more receptor sites that can be bound by endogenous opioid peptides, such as the enkephalins, endorphins and the dynorphins.

The terms "opioid agonist", "opioid analgesic" or "opioids" mean a group of drugs, of natural, synthetic, or semi-synthetic origin, that displays opium or morphine-like properties. Opioids include, for example, morphine, heroin, hydromorphone, oxymorphone, buprenorphine, levorphanol, butorphanol, codeine, dihydrocodeine, hydrocodone, oxycodone, meperidine, methadone, nalbulphine, opium, pentazocine, propoxyphene, as well as less widely employed compounds such as alfentanil, allylprodine, alphaprodine, anileridine, benzylmorphine, bezitramide, clonitazene, cyclazocine, desomorphine, dextromoramide, dezocine, diampromide, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydroxypethidine, isomethadone, ketobemidone, levallorphan, levophenacylmorphan, lofentanil, meptazinol, metazocine, metopon, myrophine, narceine, nicomorphine, norpipanone, papvretum, phenadoxone, phenomorphan, phenazocine, phenoperidine, piminodine, propiram, sufentanil, tramadol, tilidine, salts, prodrugs and mixtures thereof.

The term an "opioid antagonist" refers to any molecule that blocks the action of an opioid agonist at one or more opioid receptor types, including so-called "agonist-antagonist" and "partial agonist" molecules that act as an antagonist for one opioid receptor type and an agonist for another receptor type, such as, for example, naloxone, naltrexone, nalorphine, buprenorphine, or pentazocine.

The term "optional" or "optionally" means that the subsequently described event or circumstance may or may not occur, and that the description includes instances where the event or circumstance occurs and instances where it does not.

The term "prodrug" refers to a derivative of an active agent that requires a transformation within the body to release the active agent. Prodrugs are frequently, although not necessarily, pharmacologically inactive until converted to the active agent.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

Overview

In one aspect, the disclosure provides a composition comprising an opioid agonist and an opioid antagonist-polymer conjugate. The opioid antagonist-polymer conjugate preferably does not hydrolyze (and release opioid antagonist) upon oral administration to a patient. In some cases, the opioid antagonist-polymer conjugate does not act as a potent agonist or antagonist of opioid receptors. In some instances, the covalent bond between the polymer and the antagonist in the conjugate is broken over a defined period of time to release the antagonist into the formulation matrix. Over a defined time period, the released antagonist can at first attenuate, and subsequently ablate the effects of the opioid agonist, thereby preventing the potential for abuse or lethal overdoses.

In one aspect of the invention, the opioid antagonist-polymer conjugates are not bioavailable, centrally penetrant, or active at opioid receptors. Therefore, the adverse effects of the opioid antagonist polymer-conjugate on patients can be minimal. Further, the initial concentration of the monomeric antagonist released from the opioid antagonist-polymer conjugate is very low when dispensed to the patient, therefore, there will be minimal impact on the analgesic effect of the opioid agonist during the time required for the manufacture, distribution, and use of the formulation. The antagonist is irreversibly released over a specified time period and the agonist and antagonist are essentially impossible for abusers to physically separate due to their nearly identical chemical structures and physiochemical properties. At well-defined and pre-selected times, the antagonist concentration becomes high enough to (i) significantly reduce the liking of the opioids by potential abusers and present the serious risk of withdrawal to chronic opioid abusers, and (ii) render the pills devoid of opioid agonist effects. Therefore, the formulation becomes irreversibly deactivated and the incentive for abuse together with the diversion of abusable pills has been eliminated.

Opioid Agonist

Any opioid agonist, therapeutically acceptable salt, opioid agonist derivative, opioid agonist analog, opioid agonist homologue, polymorph or prodrug can be used in the present invention. In one aspect of the invention, the opioid agonist can be orally administered. In another aspect of the invention, opioid agonists susceptible to abuse are used. Other drugs commonly susceptible to abuse can also be used including analgesics and psychoactive drugs, including but not limited to opioids and amphetamines and benzodiazepines.

Non-limiting examples of opioid agonists that can be used in the present disclosure include: alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, mixtures of any of the foregoing, salts thereof, prodrugs thereof, and derivatives, analogs, homologues, and polymorphs thereof. In certain embodiments, the amount of the opioid agonist can be from about 75 ng to about 750 mg.

In one aspect of the invention, a pharmaceutical composition of the present invention includes one or more opioids such as hydrocodone, hydromorphone, morphine, oxycodone, oxymorphone, and/or salts or prodrugs thereof, as the therapeutically active ingredient. Prodrugs of opioids include such as those described in U.S. Pat. No. 8,217,005 to Jenkins et al., U.S. Pat. No. 8,101,661 to Mickle, and U.S. Pat. Nos. 8,133,881, 7,375,082 and 7,338,939 all to Mickle et al., and those described in U.S. Publication Nos. 20120178773, 20120142718, 20110281886, 20110262360, and 20110262359, and those described in PCT publication Nos. WO 2011/002995 and WO 2011/002991. Typically in a suitable dosage form, as described in more detail below, the drug can be present in such dosage forms in an amount normally prescribed, typically about 0.5 to about 25 percent by weight, based on the total weight of the formulation.

In a unit dose form, the amount of the opioid agonist can be from about 5 mg, 25 mg, 50 mg, 75 mg, 100 mg, 125 mg, 150 mg, 175 mg, 200 mg, or another suitable amount/range described herein. More typically, the drug can be present in an amount from about 1 mg to about 500 mg, preferably about 5 mg to 200 mg. As will be understood by one of skill in the art, a dosage form preferably contains an appropriate amount of drug to provide a therapeutic effect.

Opioid Antagonist

An opioid antagonist is a molecule that blocks the action of an opioid agonist at one or more opioid receptor types. The opioid antagonist preferably exhibits no agonist activity for an opioid receptor type and preferably exhibits antagonist activity for the mu-receptors. Suitable opioid antagonists include, but are not limited to, buprenorphine, cyclazocine, cyclorphan, naloxone, N-methylnaloxone, naltrexone, N-methylnaltrexone, nalmephene, 6-amino-6-desoxo-naloxone, levallorphan, nalbuphine, naltrendol, naltrindole, nalorphine, nor-binaltorphimine, oxilorphan, pentazocine, piperidine-N-alkylcarboxylate opioid antagonists such as those described in U.S. Pat. Nos. 5,159,081, 5,250,542, 5,270,328, and 5,434,171, and derivatives, mixtures, salts, polymorphs, or prodrugs thereof.

In one aspect of the invention, the opioid antagonist includes naltrexone, nalmefene, cyclazacine, levallorphan and mixtures thereof. In another aspect of the invention, the opioid antagonist is naltrexone or naloxone. The molar ratio of the delivered opioid antagonist to agonist can be from about 0.001:1 to about 10:1, preferably about 0.01:1 to about 2:1.

In a unit dose form, the amount of the opioid antagonist-polymer conjugate can be about 5 mg, 25 mg, 50 mg, 75 mg, 100 mg, 125 mg, 150 mg, 175 mg, 200 mg or another suitable amount/range described herein. More typically, the opioid antagonist-polymer conjugate can be present in an amount from about 1 mg to about 500 mg, preferably about 5 mg to 200 mg. As will be understood by one of skill in the art, a dosage form preferably delivers an appropriate amount of opioid antagonist to provide the desired abuse-deterrent and anti-diversion effects.

In one aspect of the invention, the antagonist is naloxone. Naloxone is almost devoid of agonist effects. Subcutaneous doses of up to 12 mg of naloxone produce no discernable subjective effects, and 24 mg naloxone causes only slight drowsiness. Small doses (0.4-0.8 mg) of naloxone given intramuscularly or intravenously, in man, prevent or reverse the effects of morphine-like opioid agonists. One mg of naloxone administered intravenously has been reported to completely block the effect of 25 mg of heroin. The effects of naloxone are seen almost immediately after intravenous administration. The drug is absorbed after oral administration but has been reported to be rapidly and extensively metabolized into an inactive form via first-pass metabolism. Therefore, it has been demonstrated to have significantly lower potency when delivered orally than when parenterally administered. Oral dosages of more than 1 g have been reported to be almost completely metabolized in less than 24 hours.

Other exemplary opioid antagonists include cyclazocine and naltrexone, both of which have cyclopropylmethyl substitutions on the nitrogen, retain much of their efficacy by the oral route and their durations of action are much longer, approaching 24 hours after oral doses.

In another aspect of the invention, the antagonist is naltrexone. Naltrexone is known as a synthetic congener of oxymorphone with no opioid agonist properties, and differs in structure from oxymorphone by replacement of the methyl group located on the nitrogen atom of oxymorphone with a cyclopropylmethyl group. As a result, the physicochemical properties of naltrexone (and chemically related antagonists) are nearly identical to those inherent to structurally related opioid agonists. This renders the physical separation of naltrexone-opioid agonist mixtures essentially impossible without the employment of highly sophisticated chemical separation techniques (e.g. high-performance liquid chromatography—HPLC). Naltrexone has been reported to exert strong preferential blocking action against mu over delta receptor sub-types. The hydrochloride salt of naltrexone is soluble in water up to about 100 mg/mL. Following oral administration, naltrexone is rapidly absorbed (within 1 hour) and has an oral bioavailability ranging from 5-40%. Naltrexone's protein binding is approximately 21% and the volume of distribution following single-dose administration is 16.1 L/kg.

It is known that when co-administered with morphine, heroin or other opioids, naltrexone blocks the development of physical dependence to opioids. In the treatment of patients previously addicted to opioids, naltrexone has been used in large oral doses (over 100 mg) to prevent the euphorigenic effects of opioid agonists. Naltrexone is commercially available in tablet form (Revia®) for the treatment of alcohol dependence and for the blockade of exogenously administered opioids. An oral dosage of 50 mg Revia® blocks the pharmacological effects of 25 mg of IV administered heroin for up to 24 hours.

The oral dosage form of the present invention can further include, in addition to an opioid agonist and an opioid antagonist-polymer conjugate, one or more drugs that may or may not act synergistically therewith. Thus, in one aspect of the invention, the oral dosage form can contain one or more opioid agonist, one or more opioid antagonist-polymer conjugate, and a non-opioid drug. Such non-opioid drugs would preferably provide additional analgesia and/or anti-inflammatory effects, and include, for example, aspirin, acetaminophen, non-steroidal anti-inflammatory drugs ("NSAIDS") such as, for example, naproxen, ibuprofen, ketoprofen, N-methyl-D-aspartate (NMDA) receptor antagonists, such as, for example, a morphinan such as dextromethorphan or dextrorphan, or ketamine, a cycooxygenase-II inhibitors ("COX-II inhibitors"); and/or glycine receptor antagonists.

Opioid Antagonist-Polymer Conjugate

An opioid antagonist-polymer conjugate can have the generalized structure as shown below:

$$(D\text{-}X\text{---}Z)_m\text{---}P \quad\quad (I)$$

wherein D is an opioid antagonist; X is a labile functionality capable of being hydrolyzed or fragmented to release D under controlled conditions; Z is a covalent linkage between X and the polymer; P is a polymer. The polymer can have a total molecular weight ranging from 1,000 to 1,000,000. Wherein m is an integer that represents the number of (D-X—Z—) units in the antagonist-polymer conjugate. The value for m can be derived from the degree of substitution, Ds, of the polymer defined as the percent of the total monomer units in the polymer that are functionalized with (—Z—X-D). The values for Ds can range from 0.001% to 100%. In one aspect of the invention, Ds is between 1% and 90%, preferably, between 1% and 80%, more preferably between 10% and 50%. The value of m will depend on the selected polymer as well as on the amount of loading onto the polymer.

In one aspect of the invention, an opioid antagonist-polymer conjugate of the invention may comprise a water-soluble polymer such as poly(ethylene glycol), covalently attached directly, or via a suitable linker, to an opioid antagonist and having a generalized structure as shown below.

$$(D\text{-}X\text{---}Z)_m\text{-PEG} \quad\quad (II)$$

wherein D is an opioid antagonist; X is a labile functionality capable of being hydrolyzed or fragmented to release D under controlled conditions; Z is a covalent linkage between X and the polymer; PEG is a PEG-based (or related linear, dendrimeric, or branched polyalkylene glycol) polymer; and m is an integer selected to be between 1 and 25, preferably, between 1 and 20, more preferably between 1 and 10. Thus, m can be 1, 2, 3, 4, 5, 6, 7, 8, 9, 10, 15, and the like.

In some embodiments, m can be an integer from about 1 to about 100, from about 100 to about 200, from about 200 to about 300, from about 300 to about 400, from about 400 to about 500, from about 500 to about 600, from about 600 to about 700, from about 700 to about 800, from about 800 to about 900, or from about 900 to about 1000, such as the integers 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 142, 143, 144, 145, 146, 147, 148, 149, 150, 151, 152, 153, 154, 155, 156, 157, 158, 159, 160, 161, 162, 163, 164, 165, 166, 167, 168, 169, 170, 172, 173, 174, 175, 176, 177, 178, 179, 180, 181, 182, 183, 184, 185, 186, 187, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 314, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000.

The PEG polymer includes polyglycols such as poly (ethylene glycol) or alkyl substituted analogs such as poly (propylene)glycol in any form, including linear forms (e.g., alkoxy PEG or bifunctional PEG), branched or multi-arm forms (e.g., forked PEG or PEG attached to a polyol core), pendant PEG, and the like.

Commercially available polymers suitable for use in the invention include, but are not limited to, mPEG-NH$_2$ ($M_w$~10 kDa, ~20 KDa), mPEG-OH ($M_w$~1 kDa, 2 KDa, ~3 KDa, ~5 KDa, ~10 KDa, ~12 KDa, ~20 KDa), 3-arm PEG-triol ($M_w$~10 kDa glycerol core, 15 kDa glycerol core, ~20 kDa glycerol core), 4-arm PEG-tetrol ($M_w$~2 kDa pentaerythritol core, ~10 kDa pentaerythritol core, ~15 kDa pentaerythritol core, ~20 kDa pentaerythritol core), 8-arm PEG-octol ($M_w$~2 kDa hexaglycerine, ~10 kDa hexaglycerine, ~15 kDa hexaglycerine, ~20 kDa hexaglycerine, ~40 kDa hexaglycerine); such as Poly(acrylic acid), $M_w$~50 kDa, Poly(l-glycerol methacrylate), Poly(acrylamide-co-acrylic acid), Poly(ethylene oxide-block-propylene oxide), Poly(L-lysine) hydrobromide, Poly(styrenesulfonic acid), Poly(vinyl alcohol), Poly(vinyl amine) hydrochloride, poly(caprolactone) diol; O,O'-bis(2-carboxyethyl)dodecaethylene glycol, Poly(allyl amine), Poly(antholesulfonic acid, sodium salt), Poly(caprolactone)triol 1,1,1-tris(hydroxymethyl)propane core, Poly(di(ethylene glycol) phthalate) diol, Poly(di (ethylene glycol)/trimethylolpropane-alt-adipic acid), polyol, PEG-bis(3-aminopropyl) terminated, PEG-bis(carboxymethyl) ether $M_w$~250 Da, PEG-bis(carboxymethyl) ether $M_w$~600 Da, PEG-block-PPG-block-PEG diol ($M_w$~1, 100 Da, ~1,900 Da, ~2,000 Da, ~2,800 Da, ~2,900 Da, ~4,400 Da, ~5,800 Da, ~8,400 Da, ~14,600 Da), PEG-ran-PPG diol ($M_w$~2,500 Da, ~12,000 Da, ~970 Da, ~1,700 Da, ~3,900 Da), PEG-tetrahydrofurfuryl ether, Poly(2-hydroxyethyl methacrylate), Polyoxyethylene bis(amine) $M_w$~2,000 Da, Polyoxyethylene bis(amine) $M_w$~20,000 Da, PPG diol ($M_w$~425 Da, ~725 Da, ~1,000 Da, ~2,000 Da, ~2,700 Da, ~3,500 Da), Poly(DL-lysine) hydrobromide ($M_w$~1,000-4,000 Da, ~30,000-70,000 Da, ~500-2,000 Da, ~1,000-4,000 Da, ~4,000-15,000 Da, ~15,000-30,000 Da, ~30,000-70,000 Da), Poly(D-lysine) hydrobromide ($M_w$~1,000-4,000 Da, ~4,000-15,000 Da, ~15,000-30,000 Da, ~30,000-70,000 Da), Poly(L-tyrosine) $M_w$~10,000-40,000 Da, Poly(L-serine) $M_w$~5,000-10,000 Da, Poly(L-threonine) $M_w$~5,000-15,000 Da, PAMAM Dendrimer G(0)-NH$_2$, ethylenediamine core (surface groups: 4, 8, 16, 32, or 64), PAMAM Dendrimer G(2)-OH, ethylenediamine core (surface groups: 16, 32, 64), DAB-AM-4, polypropyleneimine tetraamine dendrimer (surface groups: 4, 8, 16, 32, 64), PAMAM-tris (hydroxymethyl)amidomethane dendrimer, Generation 2, ethylenediamine core (surface groups: 48), PAMAM-tris (hydroxymethyl)amidomethane dendrimer, Generation 3, ethylenediamine core (surface groups: 96), PAMAM-succinamic acid dendrimer, ethylenediamine core, Generation 2 (surface groups: 16), Amino-dPEG$_2$™ t-butyl ester, Amino-dPEG$_4$™ t-butyl ester, Amino-dPEG$_8$™ t-butyl ester, Amino-dPEG$_{12}$™ t-butyl ester, Amino-dPEG$_{24}$™ t-butyl ester, m-dPEG$_4$™ amine, m-dPEG$_{12}$™ amine, m-dPEG$_{24}$™ amine, Hydroxy-dPEG$_4$™ t-butyl ester, Hydroxy-dPEG$_8$™ t-butyl ester, m-dPEG$_{11}$™ alcohol, dPEG$_{12}$™ diol, Mono-N-t-boc-amido-dPEG$_3$™-amine, Mono-N-t-boc-amido-dPEG$_{11}$™-amine, Mono-N-t-CBZ-amido-dPEG$_3$™-amine, N-t-boc-amido-dPEG$_4$™ alcohol, N-t-boc-amido-dPEG$_{12}$™ alcohol, Bis-dPEG$_5$™ acid, Bis-dPEG$_7$™ acid, Bis-dPEG$_5$™ half benzyl half acid, Bis-dPEG$_9$™ half benzyl half acid, N-Fmoc-amido-dPEG$_2$™ acid, N-Fmoc-amido-dPEG$_4$™ acid, N-Fmoc-amido-dPEG$_8$™ acid, N-Fmoc-amido-dPEG$_{12}$™ acid, N-Fmoc-amido-dPEG$_{24}$™ acid, N-CBZ-amido-dPEG$_4$™-acid, N-CBZ-amido-dPEG$_8$™-acid, N-CBZ-amido-dPEG$_{12}$™-acid, N-CBZ-amido-dPEG$_{24}$™-acid, N-t-boc-amido-dPEG$_4$™-acid, and the like.

Non-limiting examples of other polymers for use in the present invention include: polyesters, polyethers, poly(orthoesters), poly(vinyl alcohols), polyamides, polycarbonates, polyacrylamides, polyalkylene glycols, polyalkylene oxides, polyalkylene terephthalates, polyolefins, polyvinyl ethers, polyvinyl esters, polyvinyl halides, polyvinylpyrrolidone, polyglycolides, polysiloxanes, polylactides, polyurethanes, polyethylenes, polyanhydrides, polyhydroxyacids, polypropylfumerates, polycaprolactones, polyacetals, polyurethanes, polyphosphazenes, polyacrylates, polymethacrylates, polycyanoacrylates, polyureas, polystyrenes, polyamines, olefinic polymers derived from metatheses reactions with functionalized monomers, and block- or co-polymers thereof.

In some cases, the polymer is a biopolymer. Non-limiting examples of biopolymers for use in the present invention include: polyesters such as polyhyroxyalkanoates, polylactic acid and the like; proteins such as silks, collagens, gelatins, elastin, resilin, adhesives, polyamino acids, soy, zein, wheat gluten, casein, serum albumin and the like; polysaccharides such as xanthan, dextran, gellan, levan, curd ian, polygalactosamine, cellulose, pullulan, elsinan, yeast glucans, starch, agar, alginate, carrageenan, pectin, konjac, and various gums (e.g. guar), chitin, chitosan, hyaluronic acid, and the like; lipids/surfactants such as acetoglycerides, waxes, emulsions, and the like; polyphenols such as lignin, tannin, humic acid and the like; speciality polymers such as shellac, poly-gamma-glutamic acid, natural rubbers, synthetic rubbers from natural fats, and the like. Also included are chemically modified versions (to enhance solubility/functionality in the drug product formulation, resist digestion/degradation, facilitate chemical modification with antagonist synthons, etc.) of the above biopolymers.

In one aspect of the invention, the molecular weight of the polymer portion of a polymer conjugate of the invention is greater than about 1,000 daltons (Da), and more preferably is greater than about 2,000 Da. In another aspect of the invention, the polymer has a molecular weight of about 10,000 Da to about 250,000 Da. Thus, the ranges of molecular weights for the polymer portion of the conjugate can be from about 1,000 Da to about 200,000 Da, preferably about 1,000 Da to about 50,000 Da, more preferably about 7,000 Da to about 50,000 Da, or from about 10,000 Da to about 50,000 Da. The polymer backbones having an average molecular weight of about 5,000 Da, about 7,000 Da, about 10,000, about 15,000 Da and about 17,500 Da, about 20,000 Da, about 30,000 Da, about 35,000 Da, about 40,000 Da, about 45,000 Da, and about 50,000 Da are particularly preferred.

The covalent linkage between the polymer backbone and the opioid antagonist ("Z" in Formula I, above) is preferably stable enough under physiological conditions so that the monomeric opioid antagonist containing fragment is not released from the polymer following administration to a subject. The labile linkage "X" is chosen so that it is not significantly hydrolyzed when orally ingested by the pain patient, but is hydrolyzed in a predictable manner under controlled conditions over a predetermined period of time within the drug product formulation. Thus, the labile linkage X for connecting the opioid antagonist and the polymer may include, but is not limited to: ester, thioester, amide, amine, carbamate, carbonate, ether, thioether, and urea linkages or linkages designed to undergo elimination and/or cyclization-release reactions including, but not limited to, alkyesters or alkylamides substituted in the beta position of the carbonyl moiety with -D or —OC(O)-D, or appropriately tethered nucleophiles (e.g. amines, thiols, anilines, carboxylates, phenols, etc.) that are capable of releasing the opioid agonist via a kinetically controlled intramolecular cyclization-release reaction. The particular linkage and linkage chemistry employed will depend upon the available functional groups on the opioid antagonist for attachment to a polymer or conversion to a suitable attachment moiety, the presence of additional functional groups within the molecule, and the like, and can be readily determined by one skilled in the art based upon the guidance presented herein.

Using naltrexone as the exemplary opioid antagonist, the opioid-linkage for use in the invention includes the following:

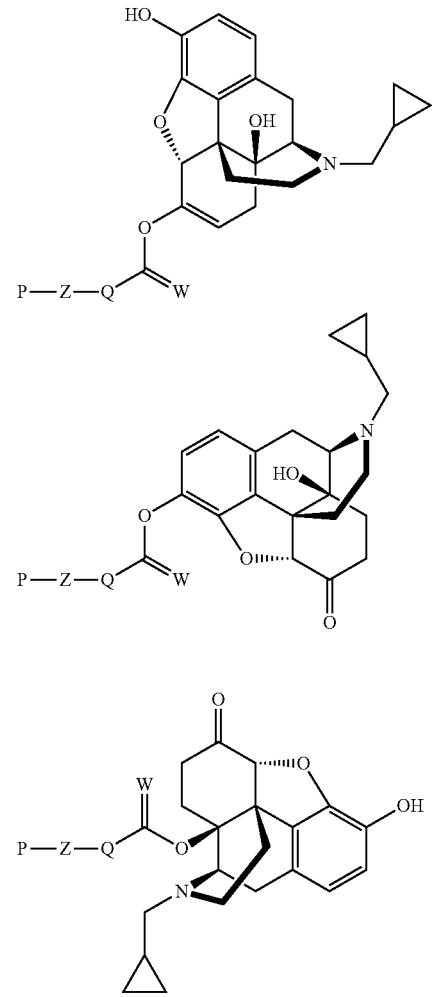

-continued

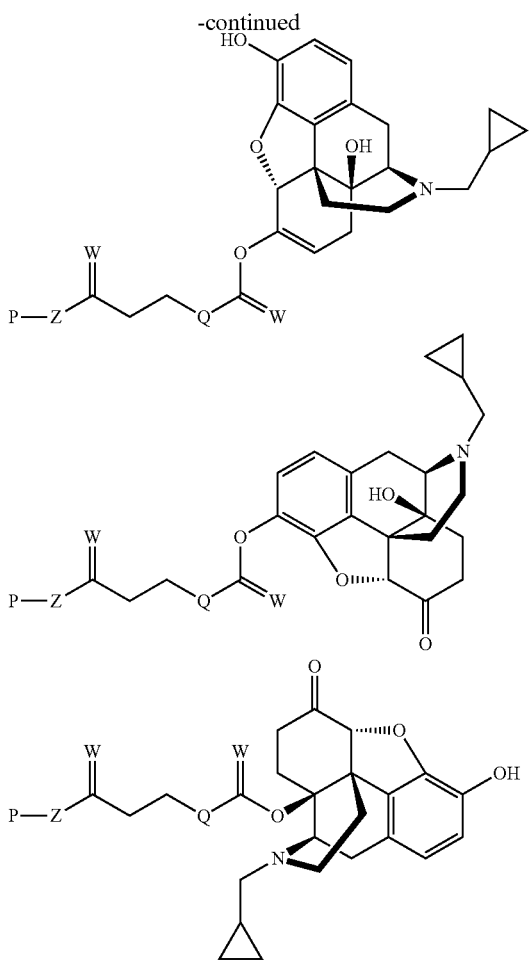

where W can be O, S, NH, NR;
Q can be O, N, S, NH, NR, C(R', R"), where R, R', and R" can be independently selected to be hydrogen, alkyl, aryl, heteroaryl. In some cases, Q can be substituted with a tethered nucleophile capable of mediating cyclization-release of the opioid antagonist via an intramolecular reaction of the carbon bearing Q;
Z can be a direct bond, an alkyl amine, a nitrogen atom, an oxygen atom, a sulfur atom, a substituted amine, an alkyl group, a cyclo-alkyl group, a heteroalkyl group, an aryl group, or an amino acid.

The opioid antagonist-polymer conjugates of the invention are not required to have, and preferably do not have opioid antagonist activity. Thus, in one aspect of the invention, a polymer conjugate in accordance with the invention will retain from about 0% to about 30% of the specific activity of the unmodified parent opioid antagonist compound. Such activity may be determined using suitable in-vivo, or in-vitro assays, depending upon the known activity of the particular opioid antagonist parent compound. For example, a functional opioid receptor based assay, or an in vivo hot-plate or tail-flick analgesia assay can be used to assess the level of antagonist activity of the polymer conjugates of the invention. Thus, an opioid antagonist-polymer conjugate of the invention will possess a specific activity of about 0%, 0.25%, 0.5%, 0.75%, 1% 2%, 5%, 10%, 15%, 25%, or 30% relative to that of the unmodified parent opioid antagonist, when measured in a suitable model, such as those well known in the art. Preferably, an opioid antagonist-polymer conjugate of the invention will have <5% of the opioid antagonist activity of the unmodified parent compound.

In another aspect of the invention, the opioid antagonist-polymer conjugates of the invention are not required to be, and preferably are not, bioavailable. Thus, in one aspect of the invention, an opioid antagonist-polymer conjugate in accordance with the invention will retain from about 0% to about 30% of the bioavailability of the unmodified parent opioid antagonist compound. Bioavailability can be determined using suitable in-vivo or in-vitro assays. Thus, an opioid antagonist-polymer conjugate of the invention will possess bioavailability of about 0%, 0.25%, 0.5%, 0.75%, 1% 2%, 5%, 10%, 15%, 25%, or 30% relative to that of the unmodified parent opioid antagonist, when measured in a suitable model, such as those well known in the art.

Non-limiting examples of polymers for use in the present invention include: polyesters, polyethers, poly(orthoesters), poly(vinyl alcohols), polyamides, polycarbonates, polyacrylamides, polyalkylene glycols, polyalkylene oxides, polyalkylene terephthalates, polyolefins, polyvinyl ethers, polyvinyl esters, polyvinyl halides, polyvinylpyrrolidone, polyglycolides, polysiloxanes, polylactides, polyurethanes, polyethylenes, polyanhydrides, polyhydroxyacids, polypropylfumerates, polycaprolactones, polyacetals, polyurethanes, polyphosphazenes, polyacrylates, polymethacrylates, polycyanoacrylates, polyureas, polystyrenes, polyamines, olefinic polymers derived from ROMP reaction with functionalized monomers, and block- or co-polymers thereof.

Non-limiting examples of biopolymers for use in the present invention include: polyesters such as polyhyroxyalkanoates, polylactic acid and the like; proteins such as silks, collagens, gelatins, elastin, resilin, adhesives, polyamino acids, soy, zein, wheat gluten, casein, serum albumin and the like; polysaccharides such as xanthan, dextran, gellan, levan, curd ian, polygalactosamine, cellulose, pullulan, elsinan, yeast glucans, starch, agar, alginate, carrageenan, pectin, konjac, and various gums (e.g. guar), chitin, chitosan, hyaluronic acid, and the like; lipids/surfactants such as acetoglycerides, waxes, emulsions, and the like; polyphenols such as lignin, tannin, humic acid and the like; speciality polymers such as shellac, poly-gamma-glutamic acid, natural rubbers, synthetic rubbers from natural fats, and the like. Also included are chemically modified versions (to enhance solubility/functionality in the drug product formulation, resist digestion/degradation, facilitate chemical modification with antagonist synthons, etc.) of the above biopolymers.

Non-limiting examples of polysaccharides and biopolymers for use in the present invention include amylose, amylopectin, glycogen, cellulose, hyaluronic acid, chondroitin sulfate, heparin, dextrin, inulin, mannan, chitin, galactose, guar gum, carrageenan, agar, furcellaran, xanthan gum, other hydrocolloid gums, pectic acid and pectin, locust bean gum, acacia, ghatti gum, pentosan, arabinogalactan, alginates and alginate derivatives, gellan, gellan gum, glucose, collagen (and gelatin), cellulose, carboxymethylcellulose, hydroxymethylcellulose, hydroxypropylmethylcellulose, methylcellulose, and methoxycellulose, fibrin, xanthan and xanthan gum, agarose, chitosan (polycationic polysaccharide polymers), albumin, human gamma globulin, pullulan, carrageenan (polyanionic polysaccharide polymers), dextrin, dextran, dextran sulfate, keratin, inulin, dextrose, amylose, glycogen, amylopectin, polylysine and other polyamino acids, and copolymers, graft copolymers, synthetic derivatives, blends and other mixtures of the above.

Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, silks, collagen, elastin, resilin, polyamino acids, soy, wheat gluten, and casein.

Non-limiting examples of polyesters include polylactic acid, polyglycolic acid, poly(lactide-co-glycolide), poly(e-caprolactone), polydioxanone, poly(ethylene terephthalate), poly(malic acid), poly(tartronic acid), polyphosphazenes, poly(orthoester), poly(valeric acid), poly(buteric acid), polyhydroxybutyrate, polyhydroxyvalerate, polyanhydride, and copolymers of the monomers used to synthesize any of the above-mentioned polymers, e.g., poly(lactic-co-glycolic acid) (PLGA) or the copolymer of polyhydroxy butyrate with hydroxyvaleric acid.

Polyethers and poly(orthoesters) can also be used in preparing the polymer conjugate for use in the present invention. These polymers can be incorporated into multiblocks resulting in block polymers having diverse degradation rates, mechanical strengths, porosities, diffusivities, and inherent viscosities. Examples of polyethers include polyethylene glycol and polypropylene glycol. An example of a multi-block copolymer is poly(ether ester amide). Additionally, triblock copolymers of poly(orthoesters) with various poly(ethylene glycol) contents are useful for their stability in water/oil (w/o) emulsions. Other useful block copolymers include di-block copolymers of poly (lactic-co-glycolic acid) and poly(ethylene glycol) (PEG), triblock copolymers of PEG-PLGA-PEG, copolymers of PLGA and polylysine, and poly (ester ether) block copolymers.

In one aspect of the invention, the polymer is poly (ethylene glycol) (PEG) or a related poly(alkylene glycol). The term PEG includes poly(ethylene glycol) in any its forms, including linear forms (e.g., alkoxy PEG or bifunctional PEG), branched or multi-arm forms (e.g., forked PEG or PEG attached to a polyol core), pendant PEG, and the like. The general formula of PEG is —CH$_2$CH$_2$O—(CH$_2$CH$_2$O)$_n$—CH$_2$CH$_2$— wherein n is from about 0 to about 500, typically from about 2 to about 200. Similar polymers can also be comprised of polypropylene glycol and related poly(alkylene) glycols.

Multi-armed or branched PEG molecules, such as those described in U.S. Pat. No. 5,932,462 can also be used as the PEG polymer. Generally speaking, multi-armed, branched, or star or dendrimeric polymers possess two or more polymer arms extending from a central branch point that is covalently attached, either directly or indirectly via intervening connecting atoms, to one or more active moieties such as an opioid antagonist. It is understood by those skilled in the art that the term poly(ethylene glycol) or PEG represents or includes all the above forms of PEG or poly(alkylene glycols).

In another aspect of the invention, the opioid antagonist-polymer conjugates are naltrexone-PEG-dimers depicted below

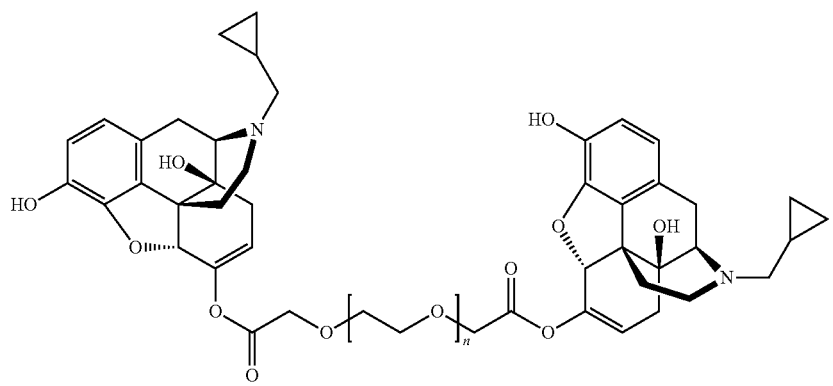

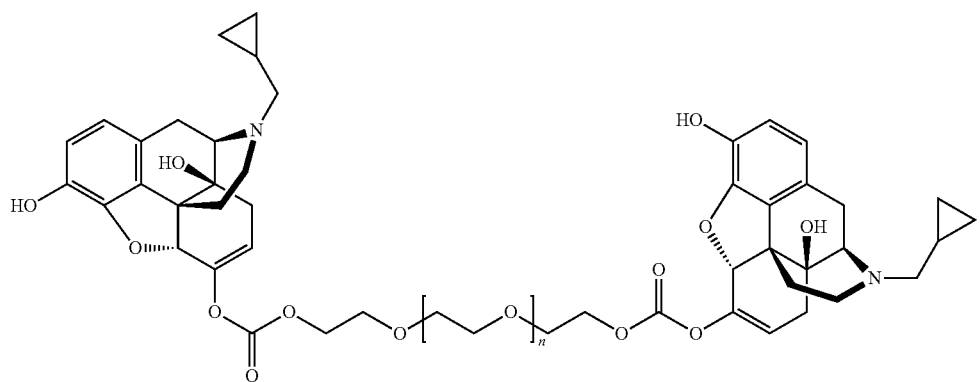
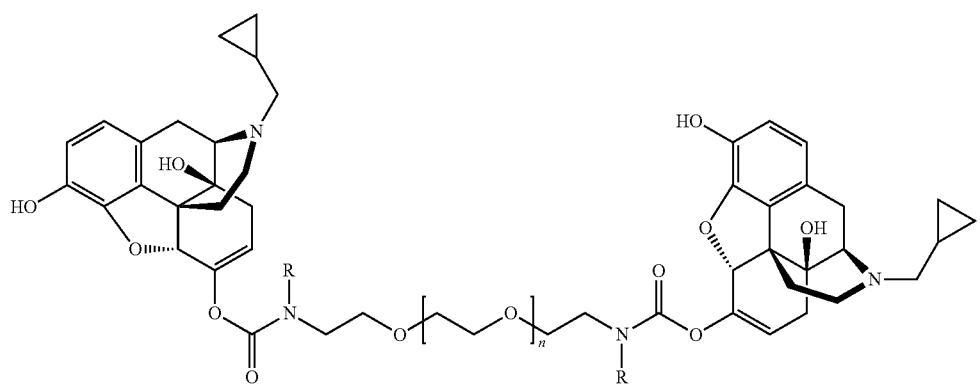
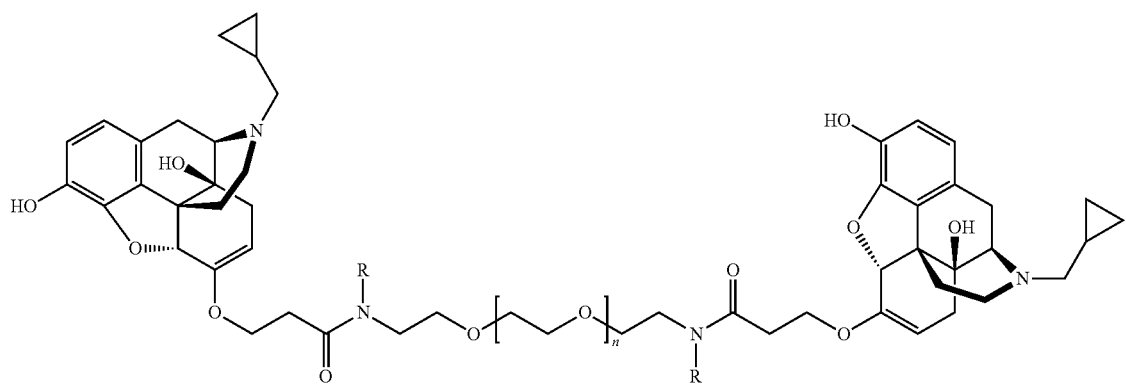
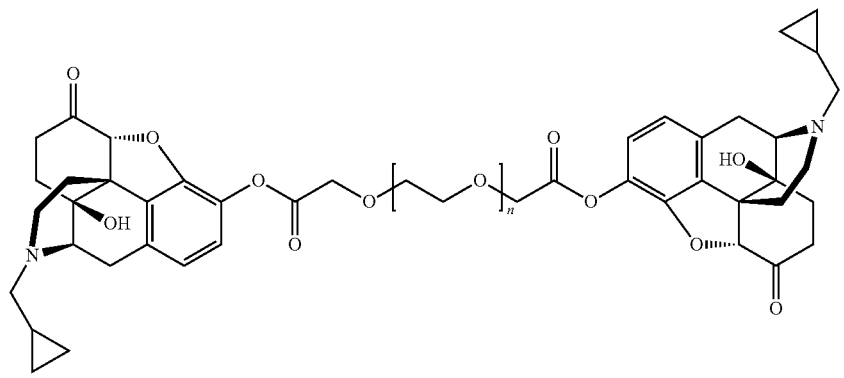

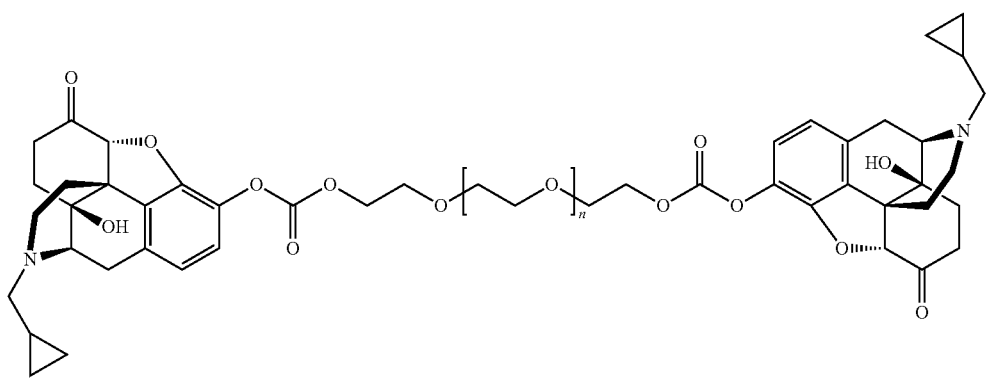
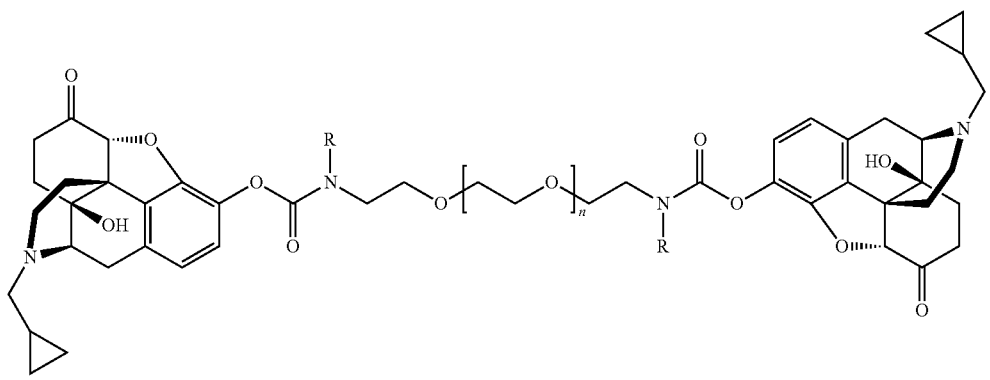
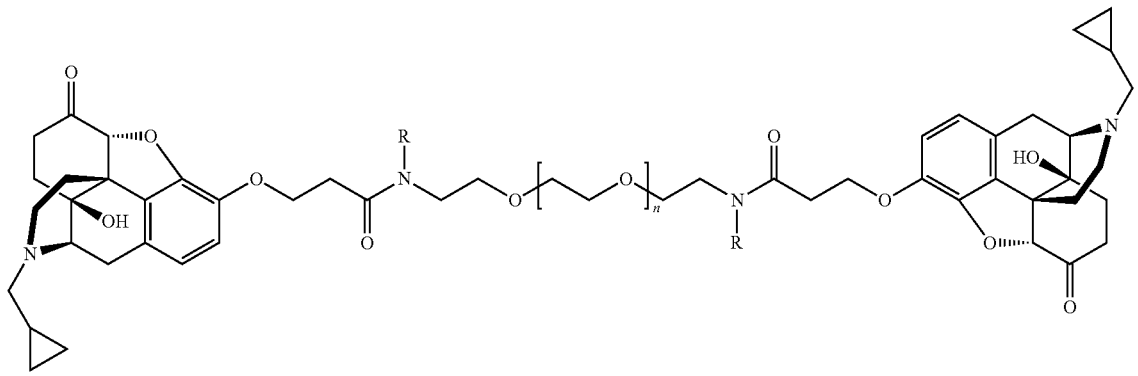
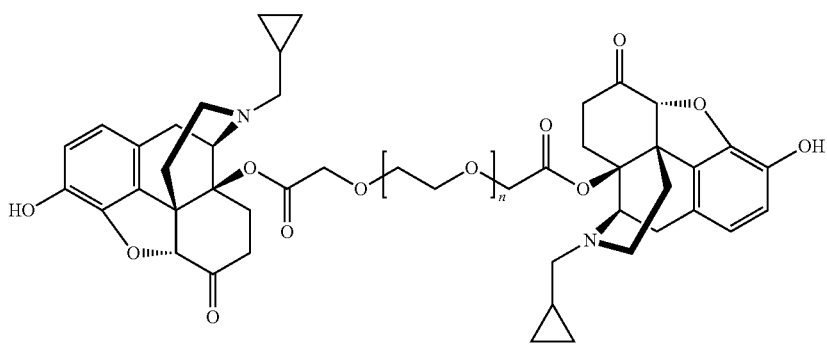

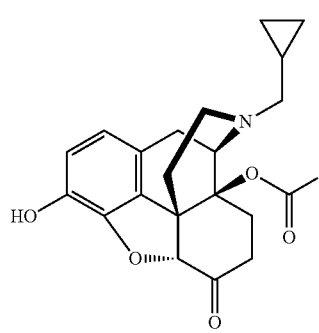
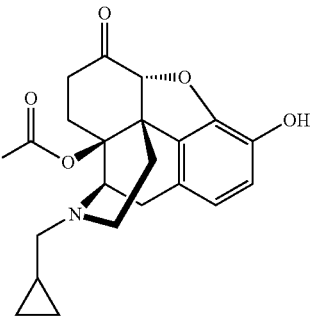
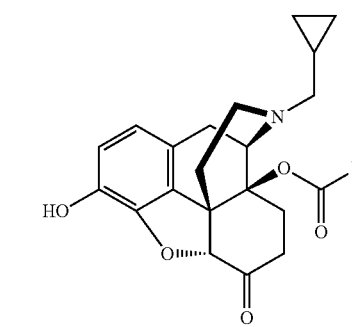
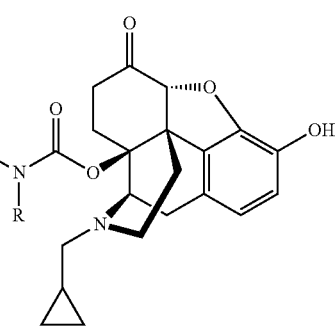

where R can be H or lower alkyl, and n can be an integer between 1 and 10,000, preferably between 1 and 100.

The opioid antagonist-polymer conjugates of the invention can be synthesized using techniques and materials known to those of skill in the art, such as described, for example, in Smith and March, MARCH'S ADVANCED ORGANIC CHEMISTRY: Reactions, Mechanisms, and Structure, Fifth Edition, (Wiley-Interscience, 2001), Vogel, A TEXTBOOK OF PRACTICAL ORGANIC CHEMISTRY, Including Qualitative Organic Analysis, Fourth Edition, New York, (Longman, 1978), Carey and Sundberg, ADVANCED ORGANIC CHEMISTY $3^{rd}$ Ed., Vols. A and B (Plenum 1992), and Green and Wuts, PROTECTIVE GROUPS IN ORGANIC SYNTHESIS $2^{nd}$ Ed. (Wiley 1991). Starting materials for the compounds of the invention can be obtained using standard techniques and commercially available precursor materials, such as those available from Aldrich Chemical Co. (Milwaukee, Wis.), Sigma Chemical Co. (St. Louis, Mo.), Lancaster Synthesis (Ward Hill, Mass.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention can include one or more steps of protection and deprotection (e.g., the formation and removal of suitable protecting groups). In addition, the synthetic procedures disclosed below can include various purifications, such as column chromatography, flash chromatography, thin-layer chromatography (TLC), recrystallization, distillation, high-pressure liquid chromatography (HPLC), dialysis, size-exclusion chromatography, and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS), and multi-angle light scattering (MALS) can be used as well. Methods of protection and deprotection, purification and identification and quantification are well known in the chemical arts.

In general, the synthetic methods use a polymer having a functional group, where the functional group can react with a functional group on the opioid antagonist, or a suitably modified opioid antagonist, thereby providing a covalently-bonded opioid antagonist-polymer conjugate. The functional group of the polymer can be, for example, a carboxylic acid, an ester, an aldehyde, an alcohol, an amine, an isocyanate, and the like. The functional group of the polymer can be selected such that it can form a covalent bond either at the phenolic group, tertiary alcohol, amine, or the ketone group of the antagonist. Optionally, the opioid antagonist can be chemically modified either at the phenolic group, tertiary alcohol, amine, or the ketone group with an appropriate moiety prior to attachment to the polymer. The syntheses of opioid antagonist-polymer conjugates covalently bonded via an ester linkage, a carbonate linkage, a primary or secondary carbamate linkage are generally described herein.

For example, the polymer and the antagonist can be bonded using a coupling reagent to form an ester linkage, or an activated antagonist, such as an antagonist whose phenolic group is activated as a para-nitrophenyl carbamate, or related activated derivative, that can be reacted with an alcohol-containing or amine-containing polymer to form a carbonate or a carbamate linkage, respectively. In another aspect, the polymer and the antagonist can be directly attached. In yet another aspect, the polymer and the antagonist can be bonded via a labile functional group X that is capable of being hydrolyzed or fragmented under controlled conditions.

The opioid antagonist-polymer conjugate product can be collected and purified using methods known in the art. In general, compounds as described herein can be purified by any of the means known in the art, including chromatographic means, such as high performance liquid chromatography (HPLC), preparative thin layer chromatography, flash column chromatography and ion exchange chromatography, size exclusion chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

In one aspect of the invention, opioid antagonists where the ketone group has been modified are provided, wherein the opioid antagonist has an optionally substituted morphinan structure:

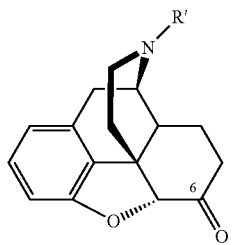

wherein the ketone is situated at the 6-position of the morphinan structure and R' is hydrogen or other group, such as, but not limited to, alkyl or substituted alkyl. The opioid antagonist can be any of the antagonists containing a ketone group. In certain instances, a ketone-containing opioid antagonist is selected from naloxone and naltrexone.

In certain embodiments, the opioid antagonist has the following optionally substituted morphinan structure:

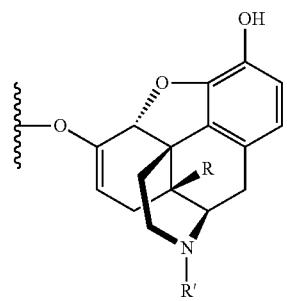

wherein R' is hydrogen or other group, such as, but not limited to, alkyl or substituted alkyl, and R is hydrogen, hydroxyl, methoxy, ethoxy, alkyl or substituted alkyl. The structure is shown as an enol, in which attachment to the polymer, preferably using a linker, is through the enolic oxygen atom of the ketone moiety such that the hydrogen atom of the corresponding enolic group of the ketone-containing opioid is replaced.

In certain embodiments, the opioid antagonist D has the following optionally substituted morphinan structure:

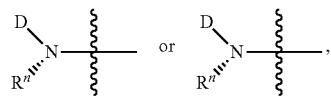

wherein D is an opioid and R″ is hydrogen or other group, such as, but not limited to, alkyl or substituted alkyl. The structures above result from a ketone that has been reductively aminated, in which attachment to the polymer is through the resulting amino group such that the hydrogen atom of the corresponding amino group is replaced.

In certain embodiments, the opioid antagonist has the structure where the ketone can be reductively aminated and the attachment to the polymer is through the amino group that is generated from reductive amination of the ketone moiety. A representative formula of such an opioid antagonist is below:

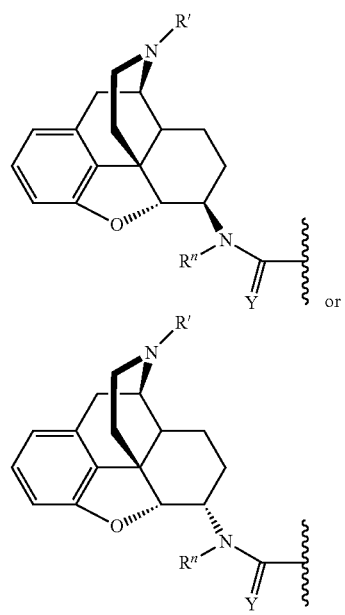

wherein R' is hydrogen or other group, such as, but not limited to, alkyl or substituted alkyl and R" is hydrogen or other group, such as, but not limited to, alkyl or substituted alkyl. As shown, the attachment to the polymer is through the amino group generated from reductive amination of the ketone moiety such that the hydrogen atom of the amino group is replaced by a covalent bond to the polymer or a linker that is attached to the polymer. For example, the ketone group of naloxone or naltrexone can be subjected to reductive amination to form an amino derivative of naloxone or naltrexone using known methodology. The amino derivative can then reacted with an active ester- or active carbonate-terminated polymer to form an amide or carbamate linkage.

A representative synthesis for an antagonist-polymer conjugate, where the covalent bond is via the ketone group of the opioid-antagonist is shown below in Scheme I.

Scheme I

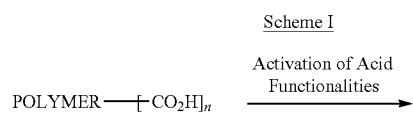

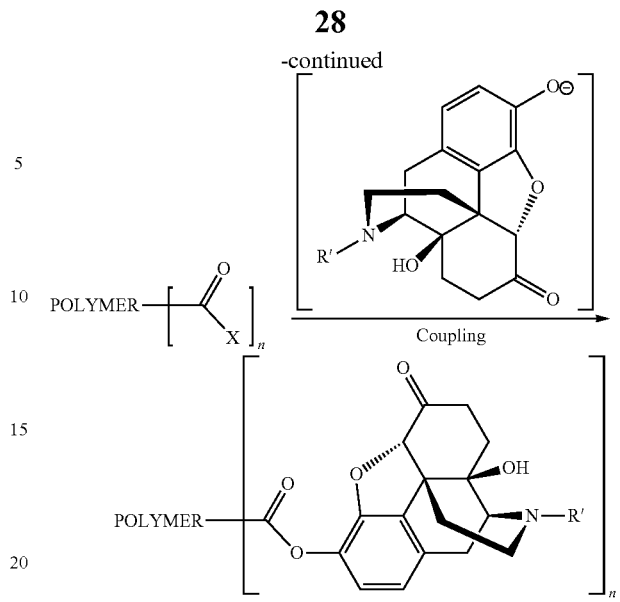

A representative synthesis for an antagonist-polymer conjugate, where the covalent bond is via the phenolic group of the opioid-antagonist is shown below in Schemes II and III.

Scheme II

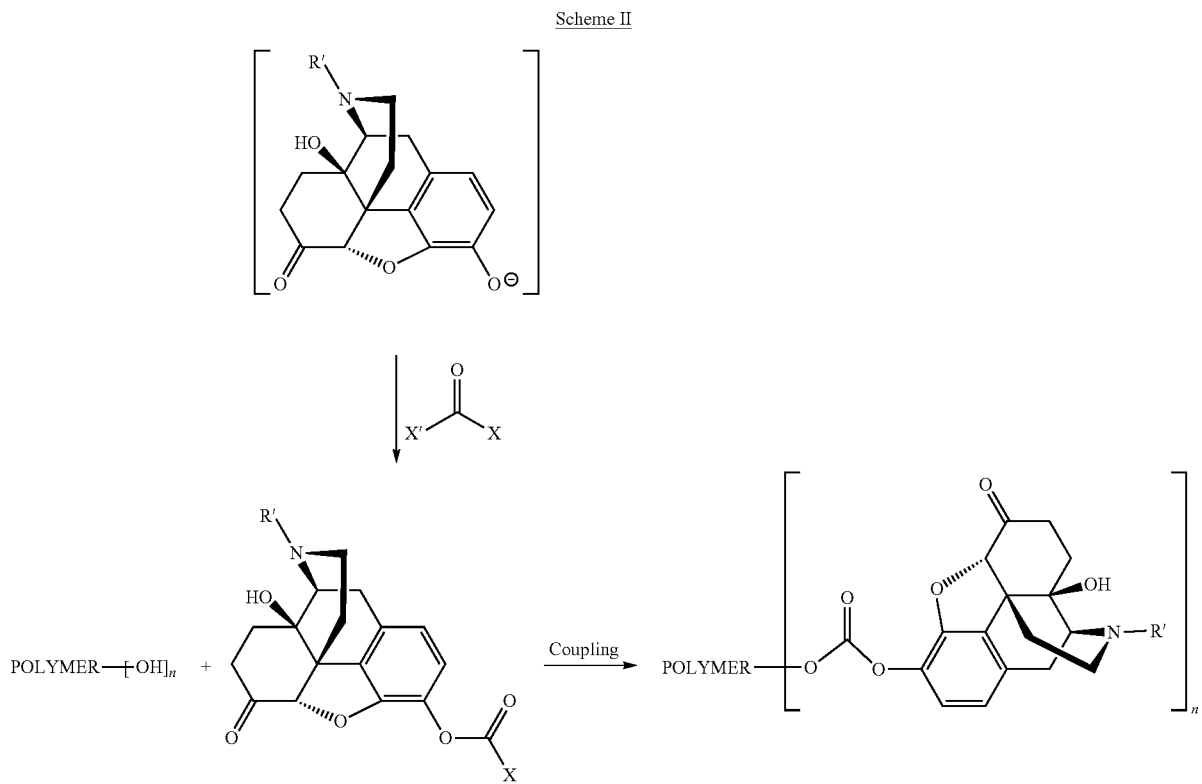

Scheme III
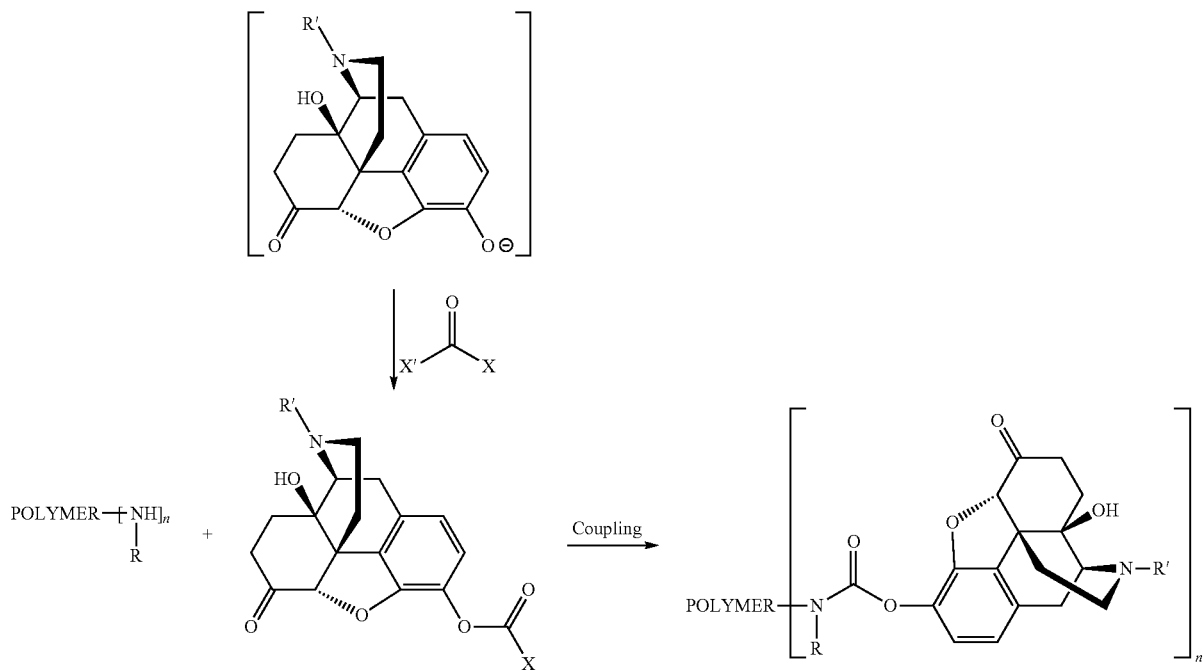
A representative synthesis for an antagonist-polymer conjugate, where the covalent bond is via the phenolic group of the opioid-antagonist, and the attachment to the polymer is via an amide bond is shown below in Scheme IV.
Scheme IV
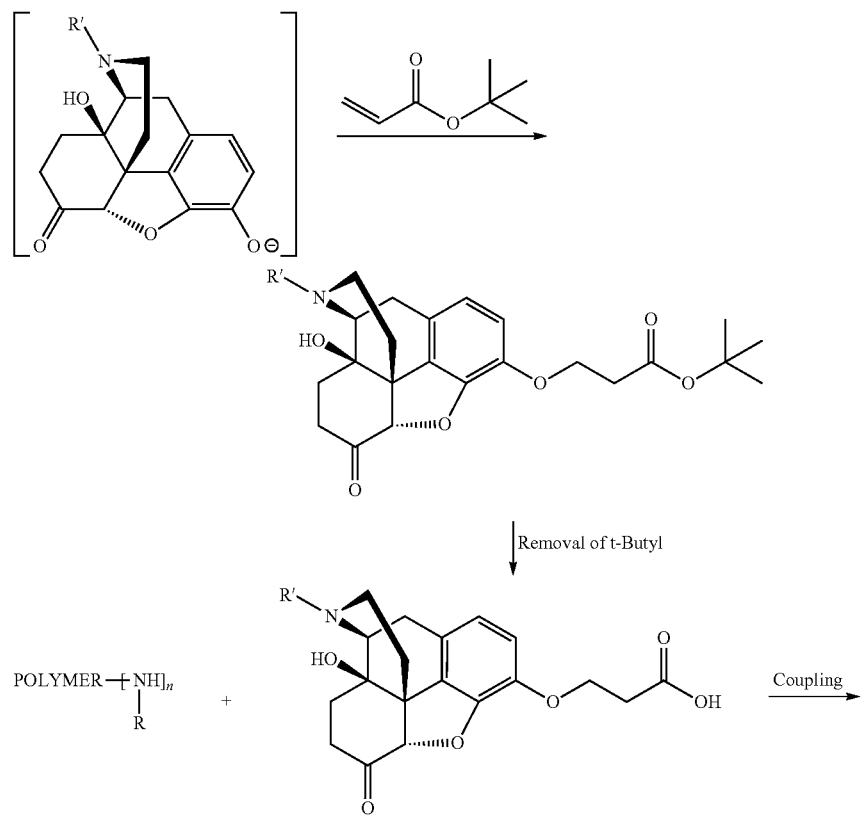

-continued
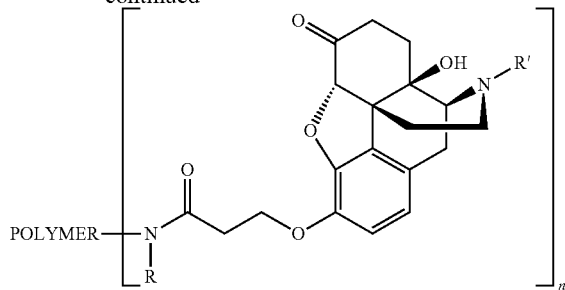
A representative synthesis for an antagonist-polymer conjugate, where the covalent bond is via the phenolic group of the opioid-antagonist using the labile carbonate functionality, and the attachment to the polymer is via an amide bond is shown below in Scheme V.
Scheme V
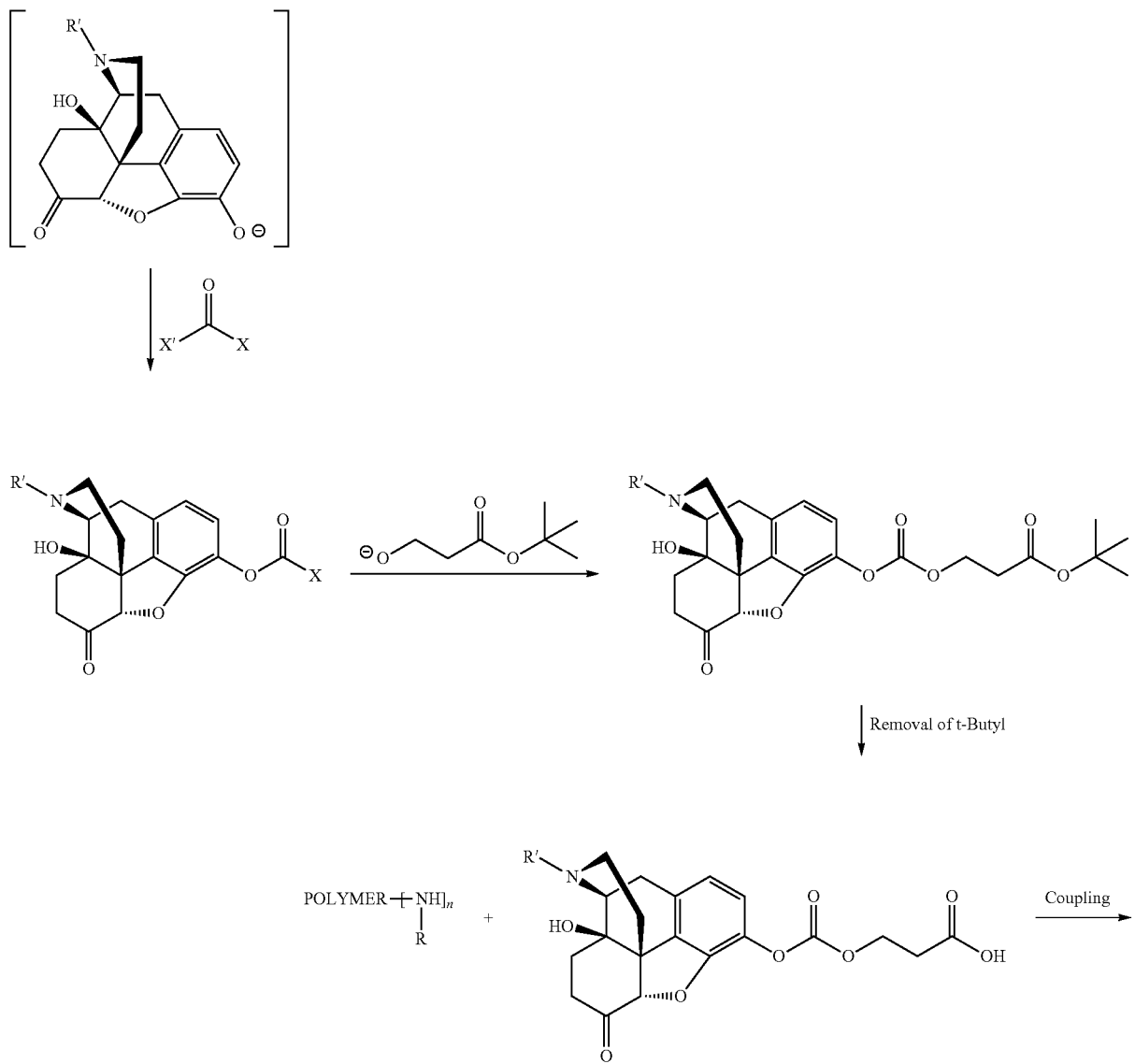

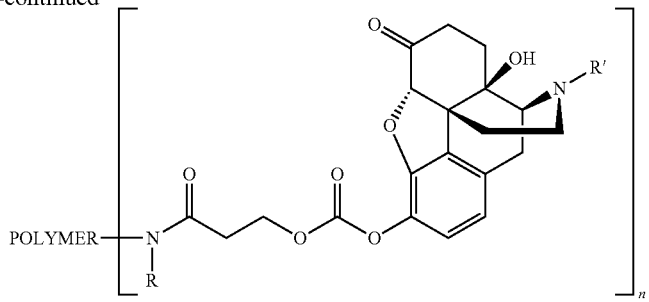

A representative synthesis for an antagonist-polymer conjugate, where the covalent bond is via the ketone group of the opioid-antagonist, and an ester, that is labile under certain conditions, links the antagonist to the polymer is shown below in Scheme VI.

Scheme VI

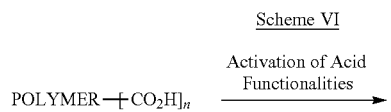

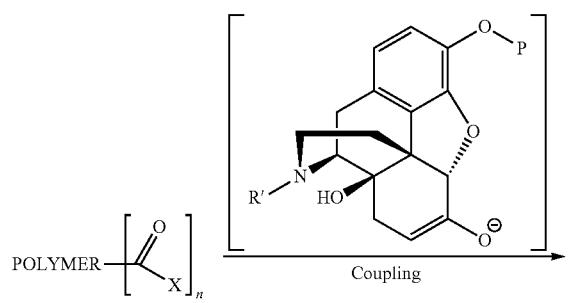

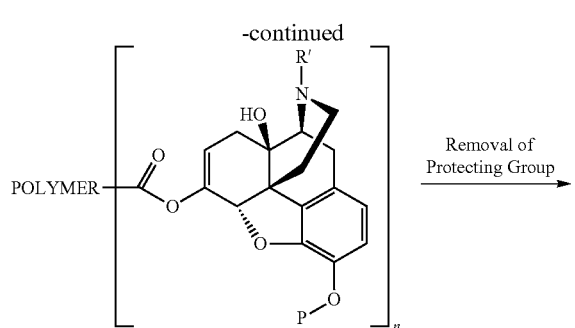

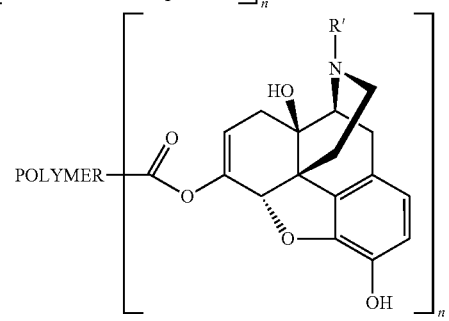

A representative synthesis for an antagonist-polymer conjugate, where the covalent bond is via the ketone group of the opioid-antagonist, and a carbonate, that is labile under certain conditions, links the antagonist to the polymer is shown below in Scheme VII.

Scheme VII

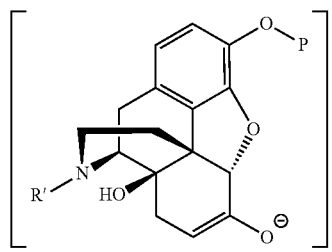

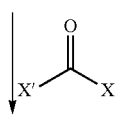

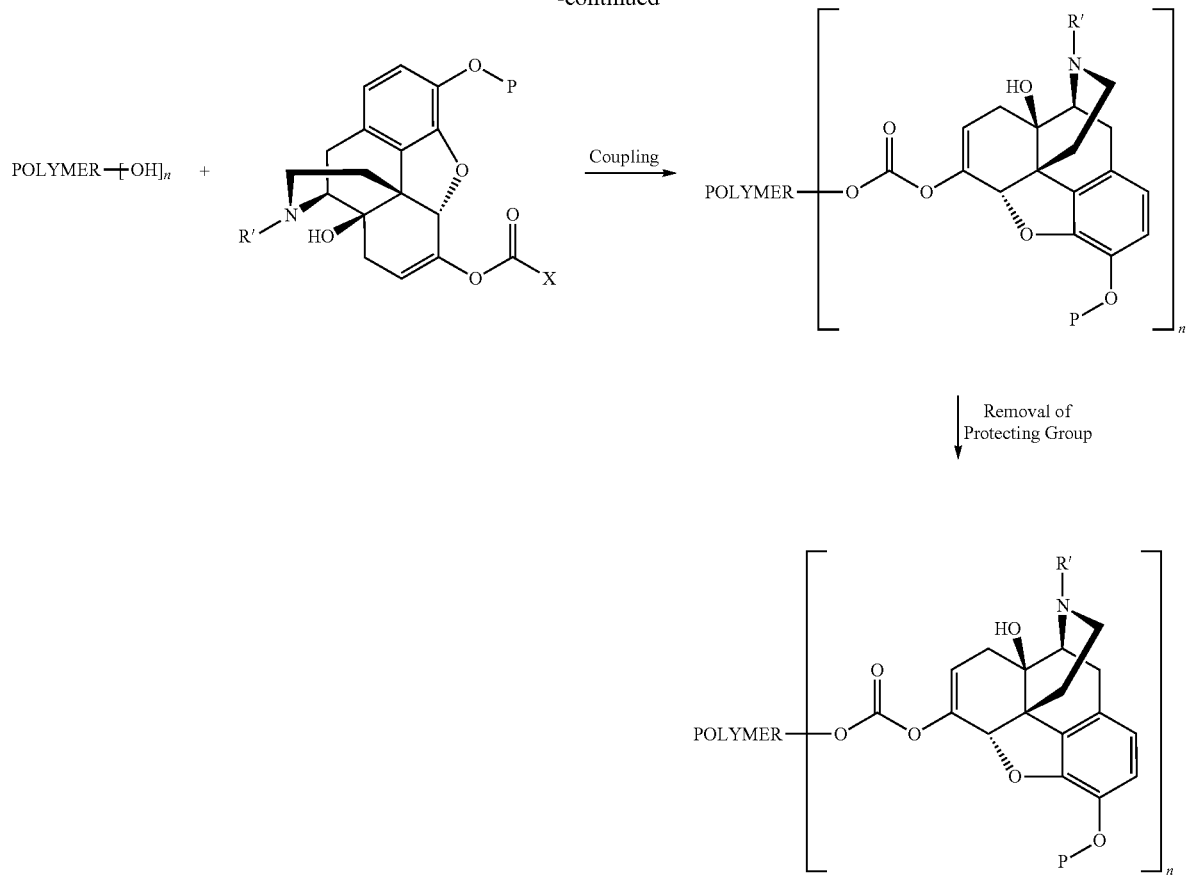
A representative synthesis for an antagonist-polymer conjugate, where the covalent bond is via the ketone group of the opioid-antagonist, and a carbamate, that is labile under certain conditions, links the antagonist to the polymer is shown below in Scheme VIII.
Scheme VIII
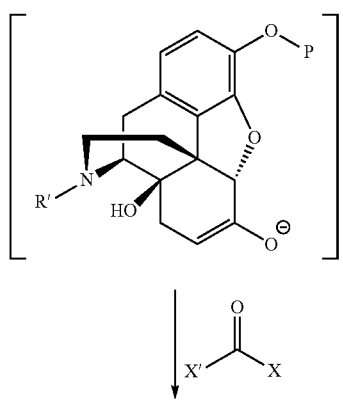

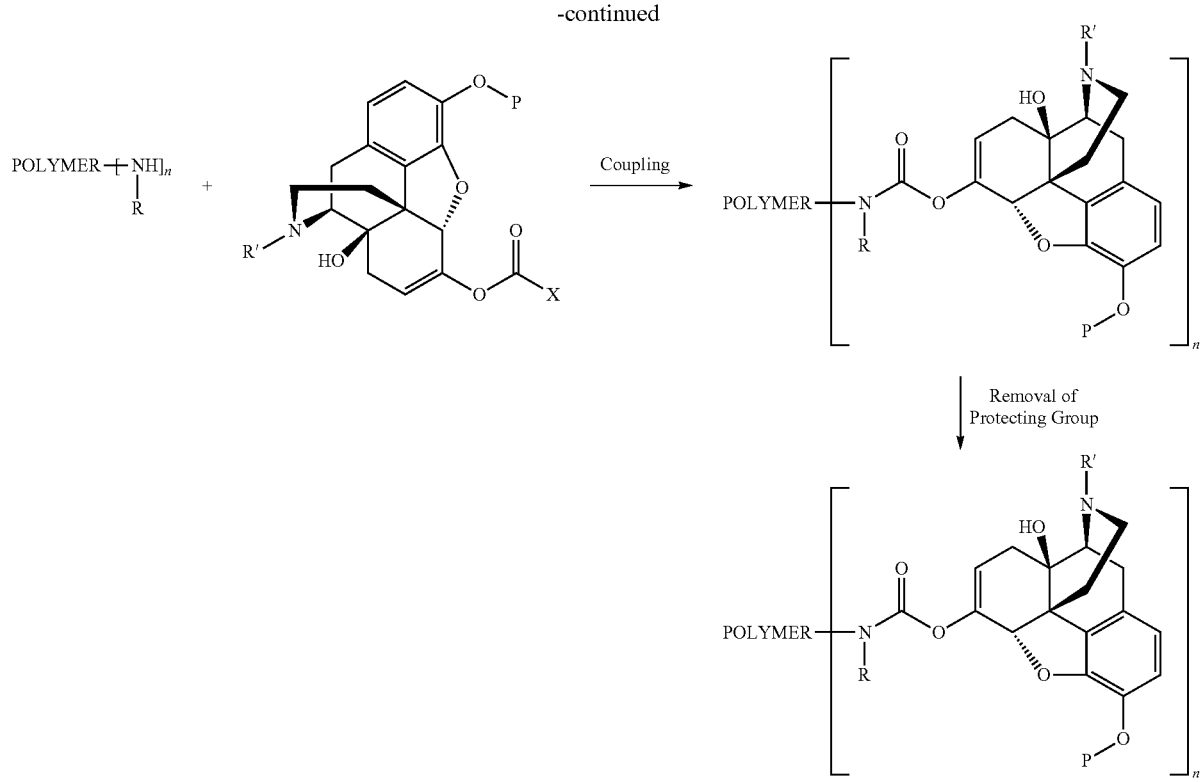
A representative synthesis for an antagonist-polymer conjugate, where the covalent bond is via the ketone group of the opioid-antagonist, and an ether functionality links the antagonist to the polymer is shown below in Scheme IX.
Scheme IX
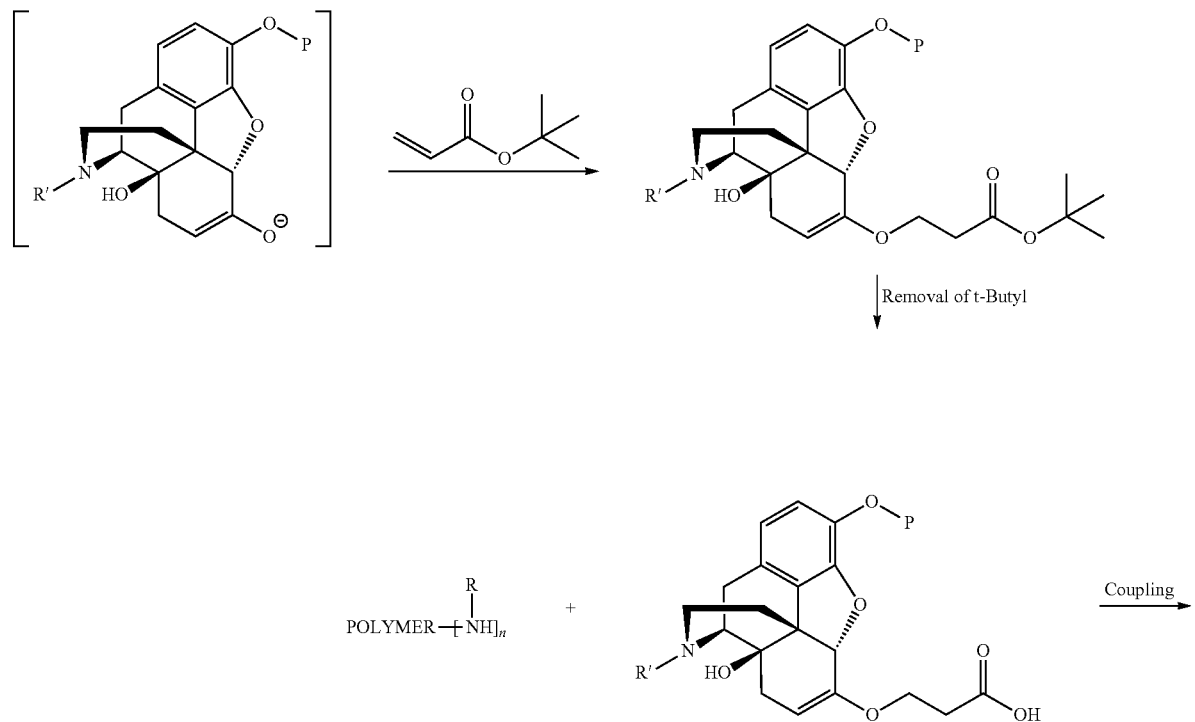

-continued
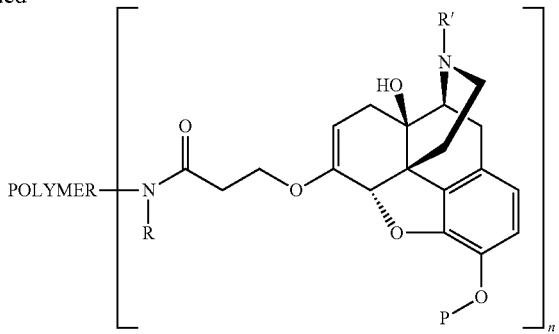
| Removal of Protecting Group
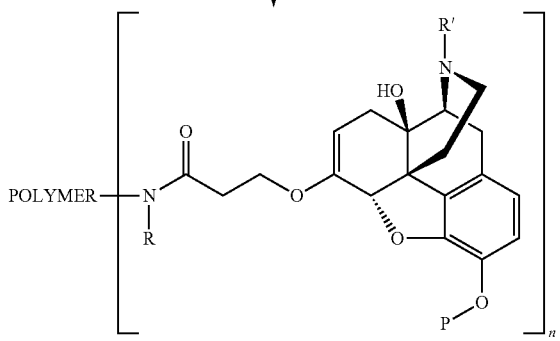
A representative synthesis for an antagonist-polymer conjugate, where the covalent bond is via the ketone group of the opioid-antagonist, and a carbonate, that is labile under certain conditions, links the antagonist to the polymer is shown below in Scheme X.
Scheme X
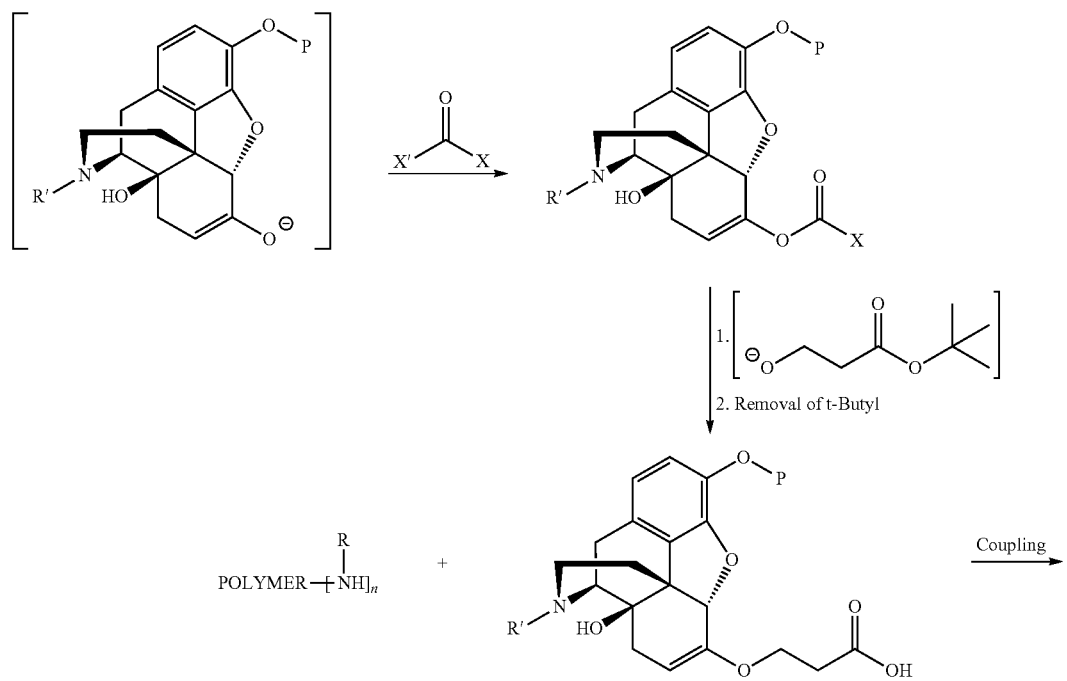

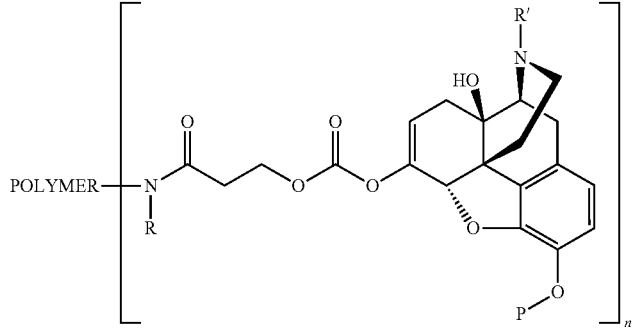
Exemplary antagonist-polymer conjugates, where the covalent bond is via a ketone group, a phenolic group, or a tertiary hydroxyl group of the opioid-antagonist, and the labile functionality is an ester that links the antagonist to the polymer are shown below.
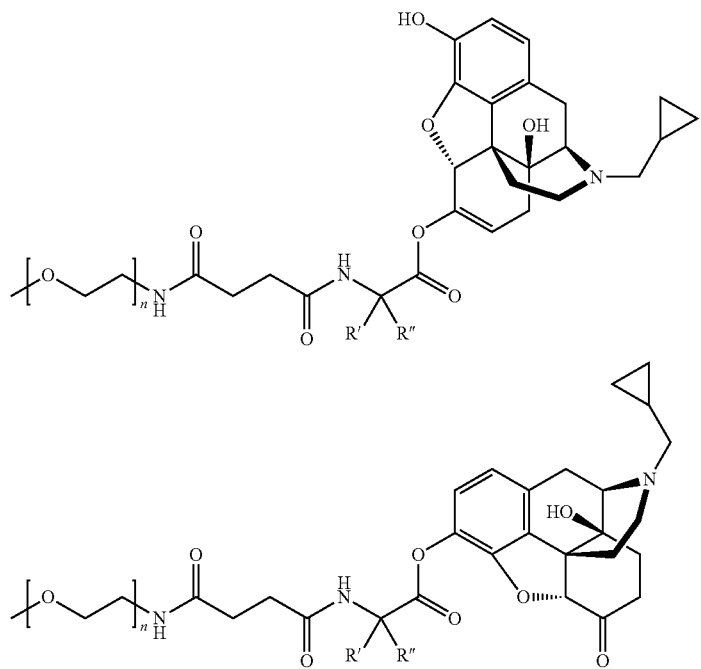

-continued
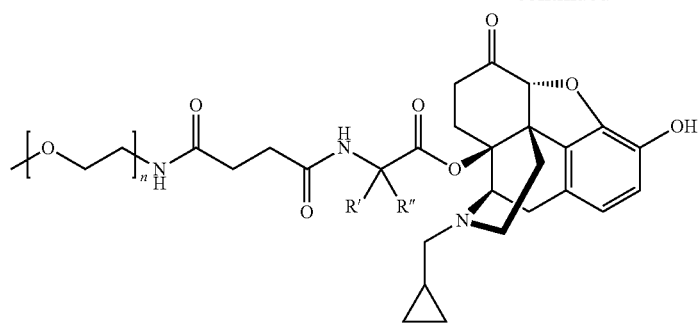
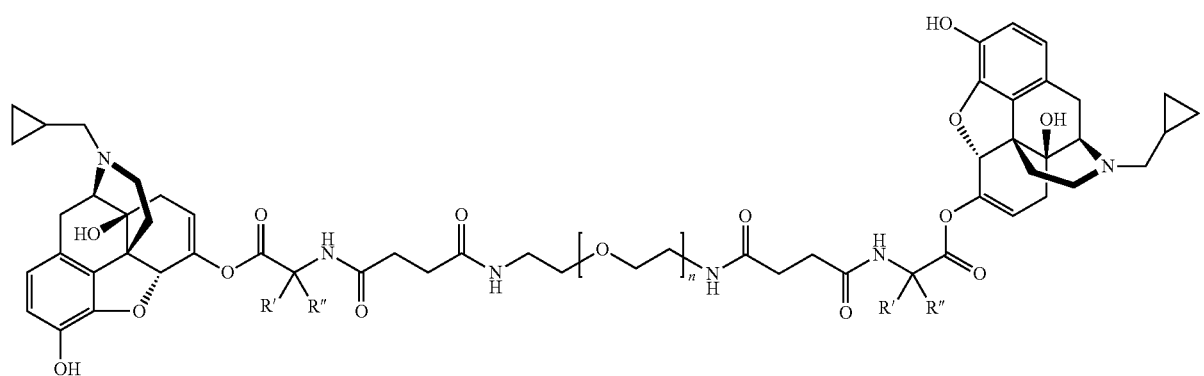
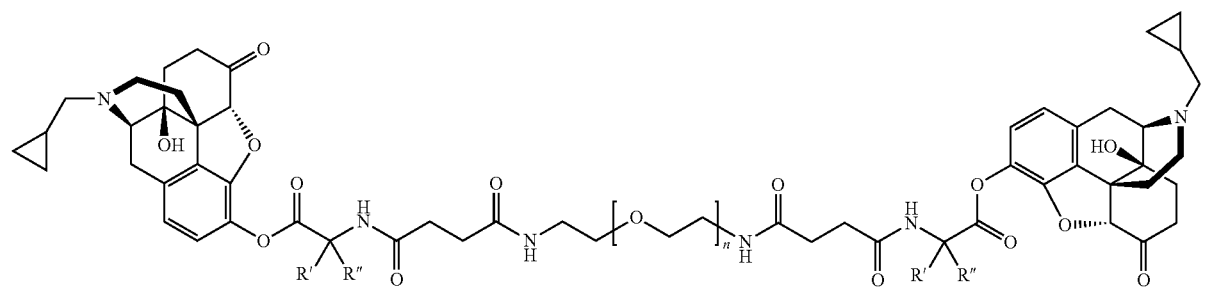
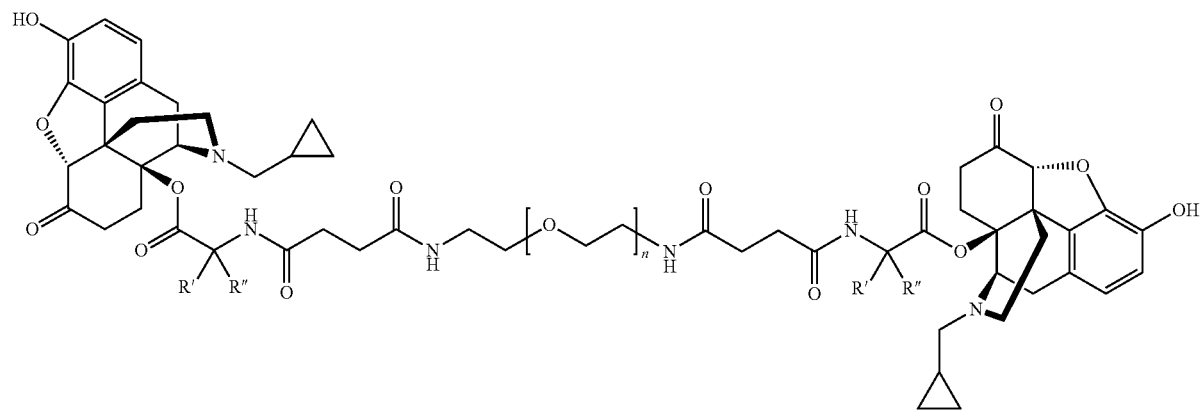

45
46
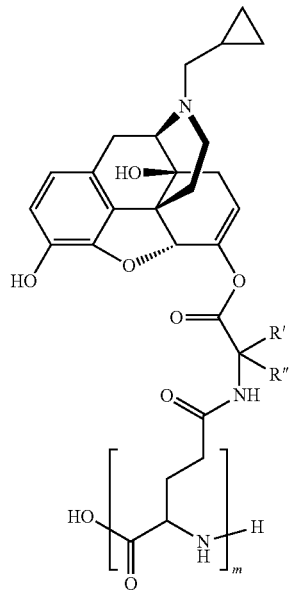
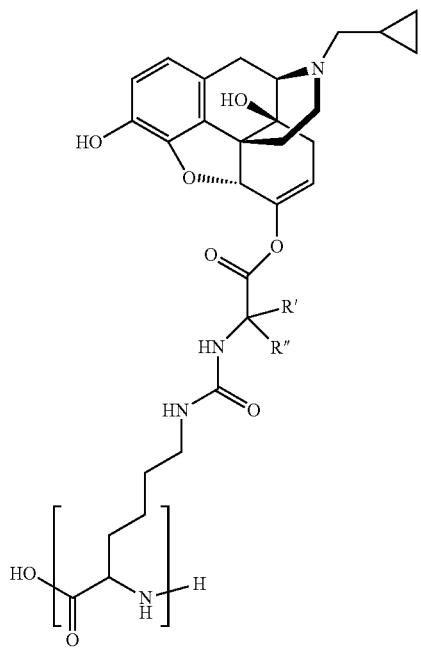
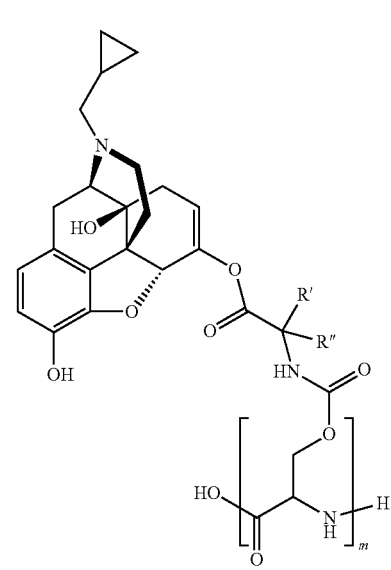
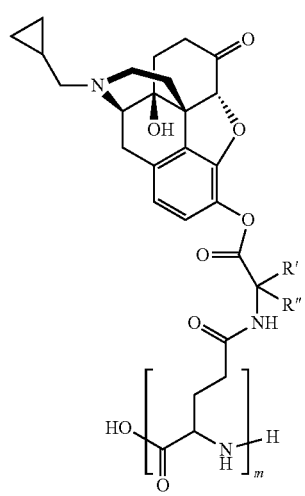
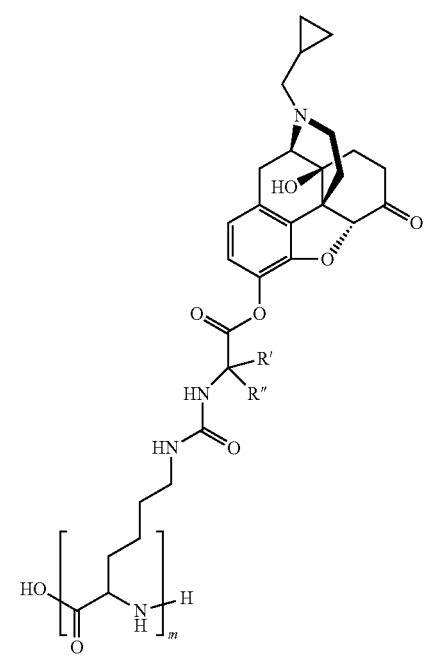
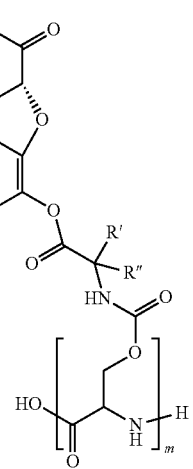

-continued
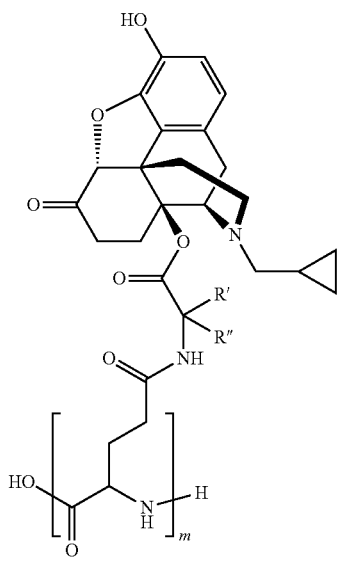 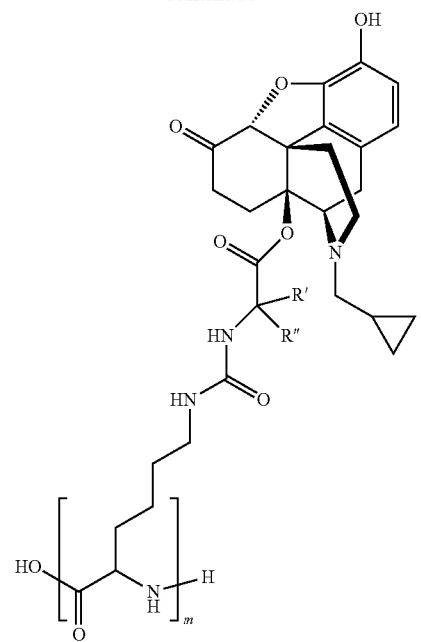 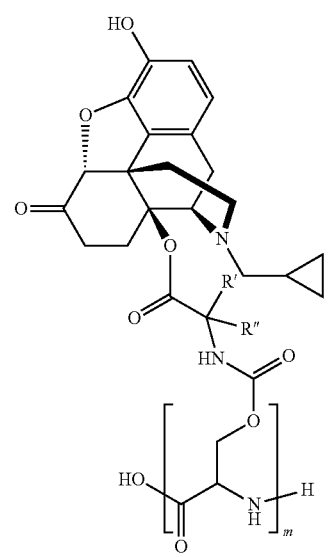
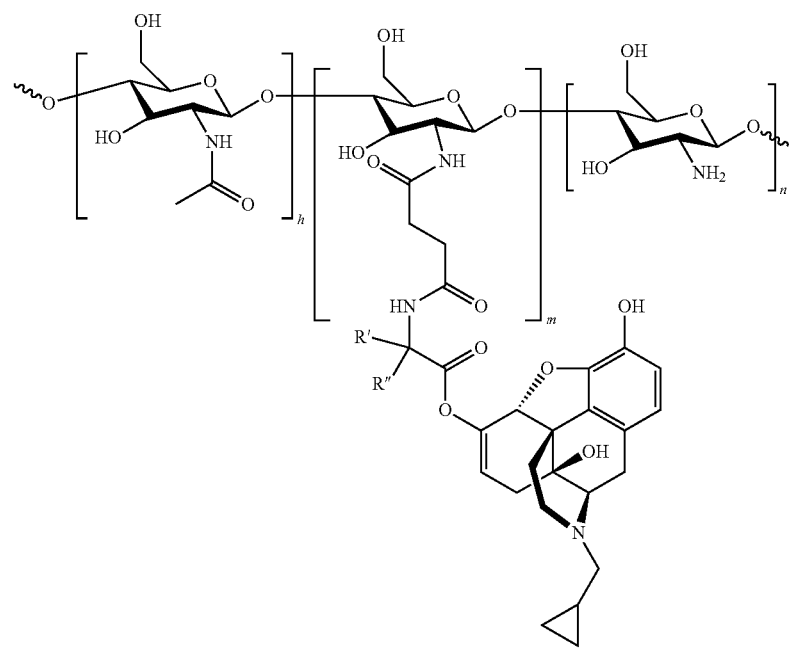

-continued
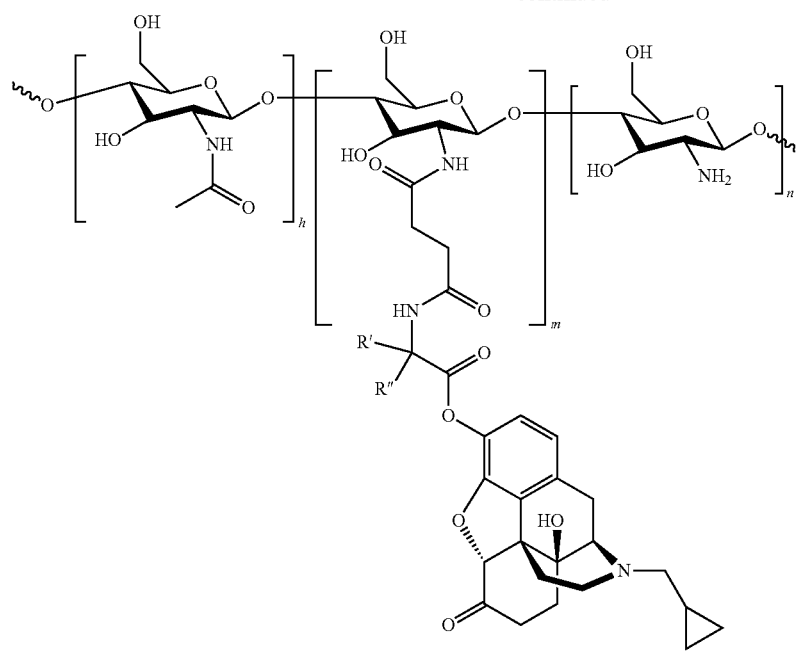
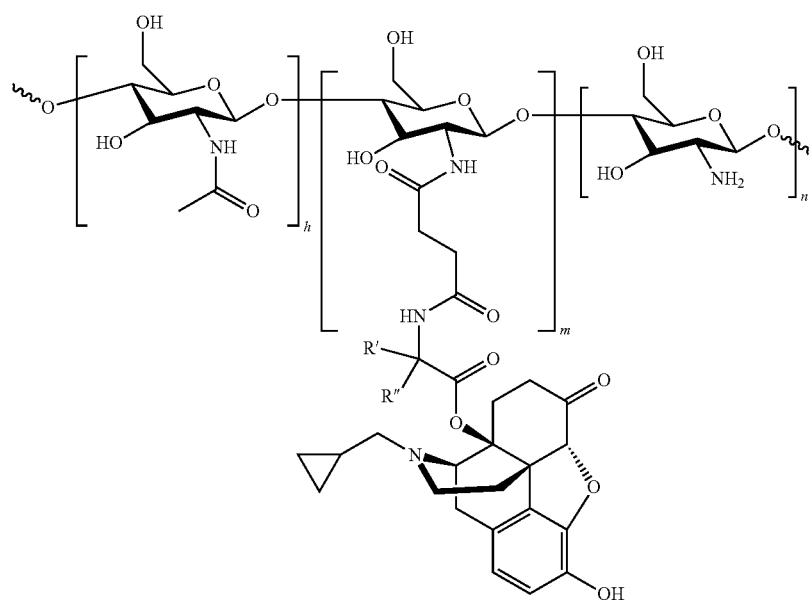

-continued
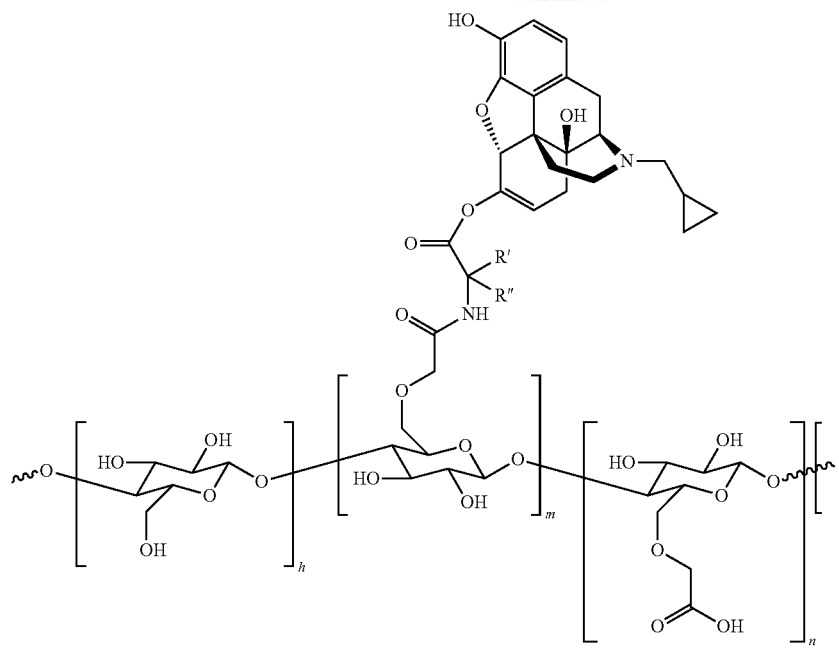
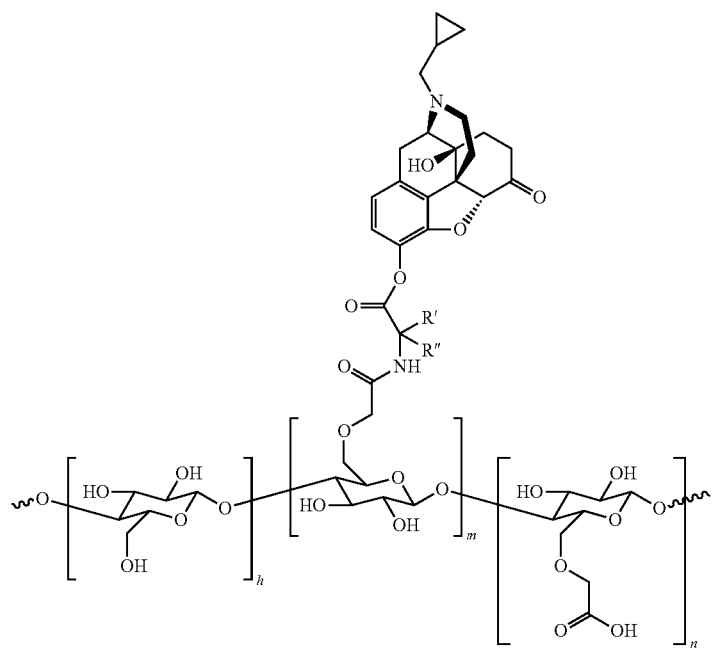

-continued

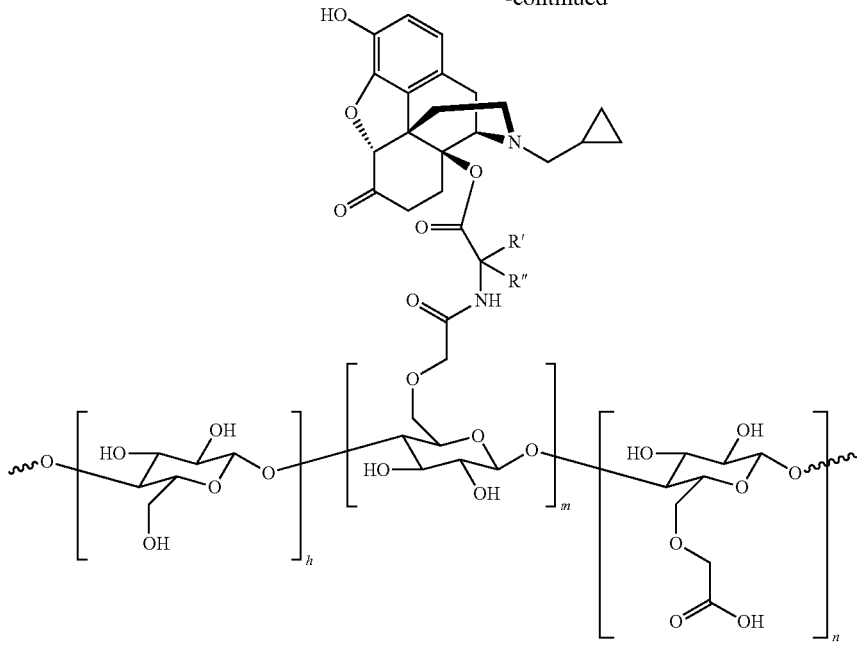

where R' and R" can be hydrogen or lower alkyl, and m can be an integer between 1 and 10,000, preferably between 1 and 1000, and the values for n defining the length of the polyethylene glycol polymer, can be an integer between 10 and 10,000, preferably between 10 and 1000.

Exemplary antagonist-polymer conjugates, where the covalent bond is via a ketone group, a phenolic group, or a tertiary hydroxyl group of the opioid-antagonist, and the labile functionality is an ester that links the antagonist to the polymer are shown below. The opioid agonist is released via an intramolecular cyclization-release mechanism, where R', R", are as defined above and the values for n defining the length of the polyethylene glycol polymer, can be an integer between 10 and 10,000, preferably between 10 and 1000.

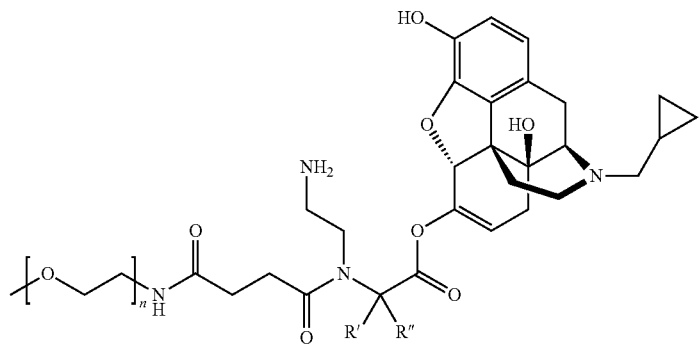

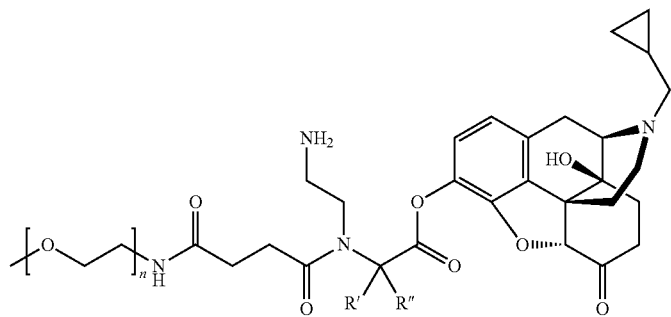

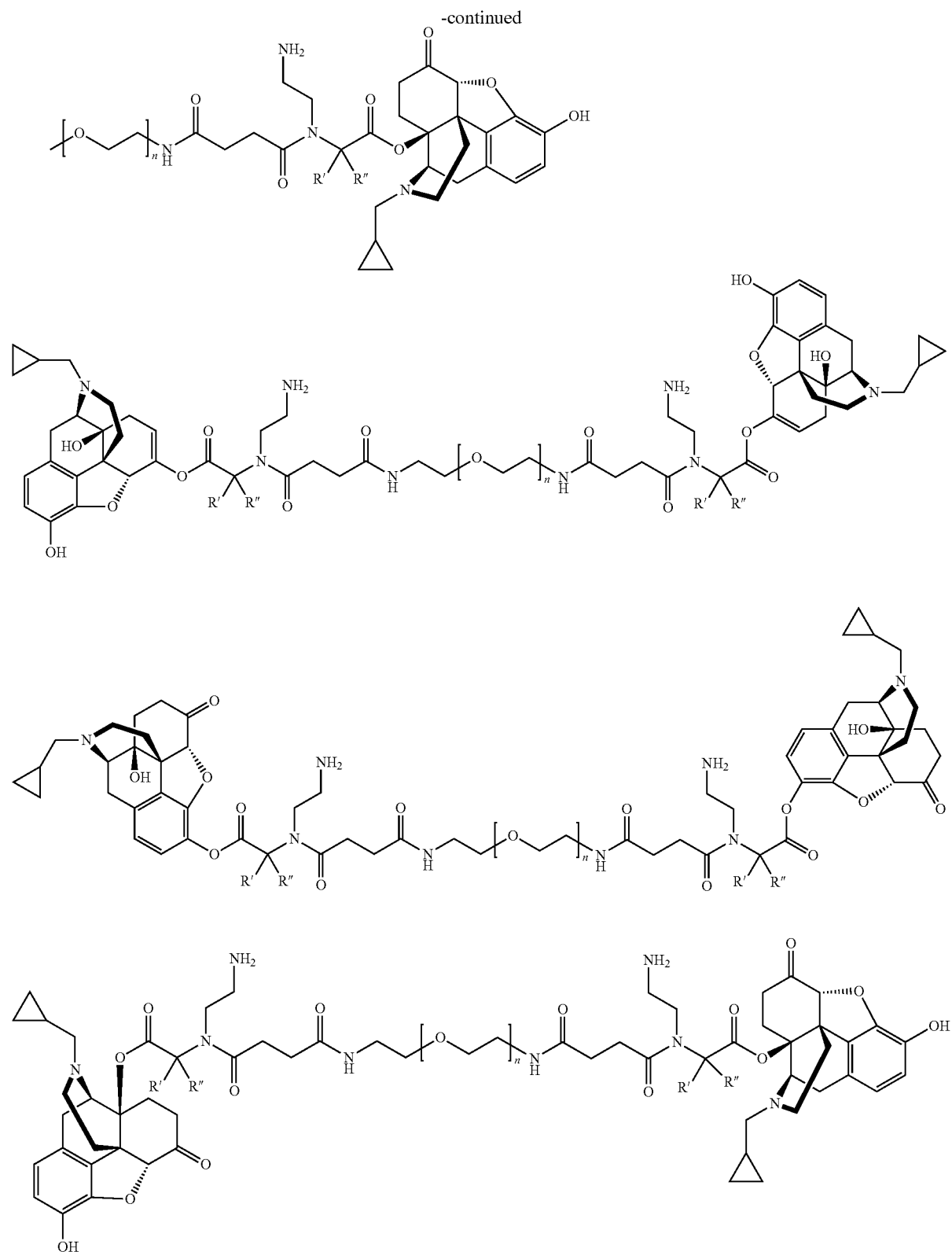
Exemplary antagonist-polymer conjugates, where the covalent bond is via a ketone group, a phenolic group, or a tertiary hydroxyl group of the opioid-antagonist, and the labile functionality is a carbamate that links the antagonist to the polymer are shown below:

57
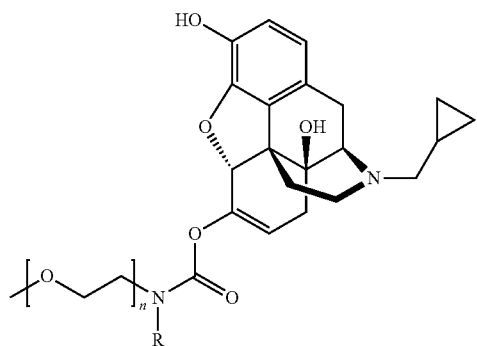
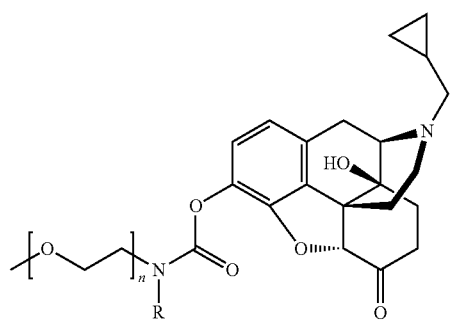
58
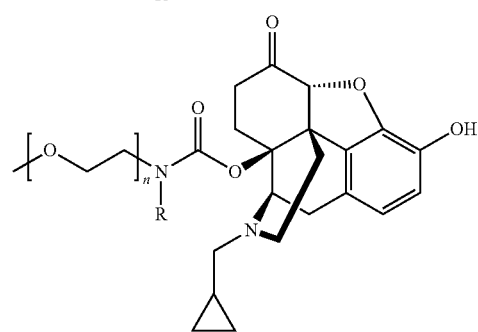
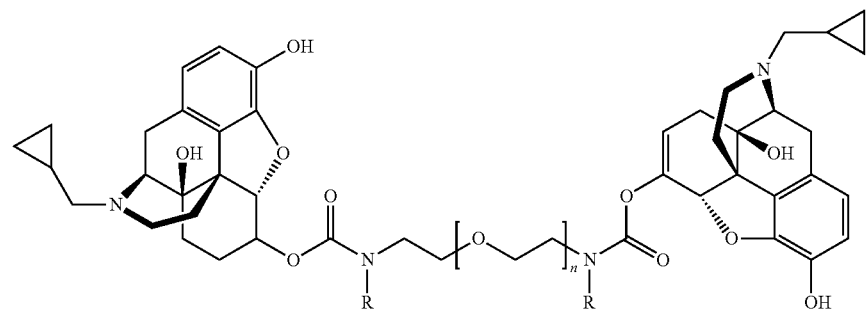
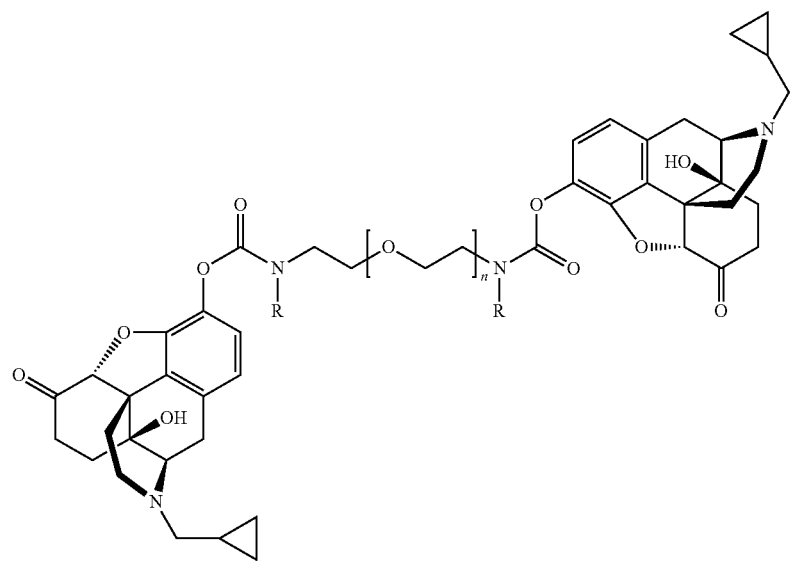

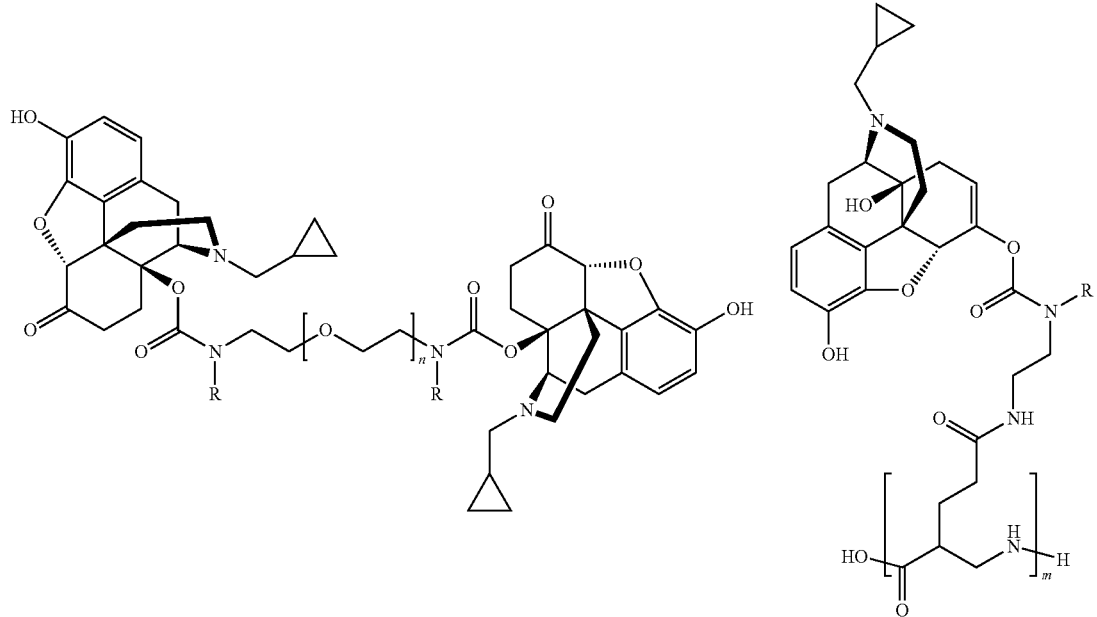
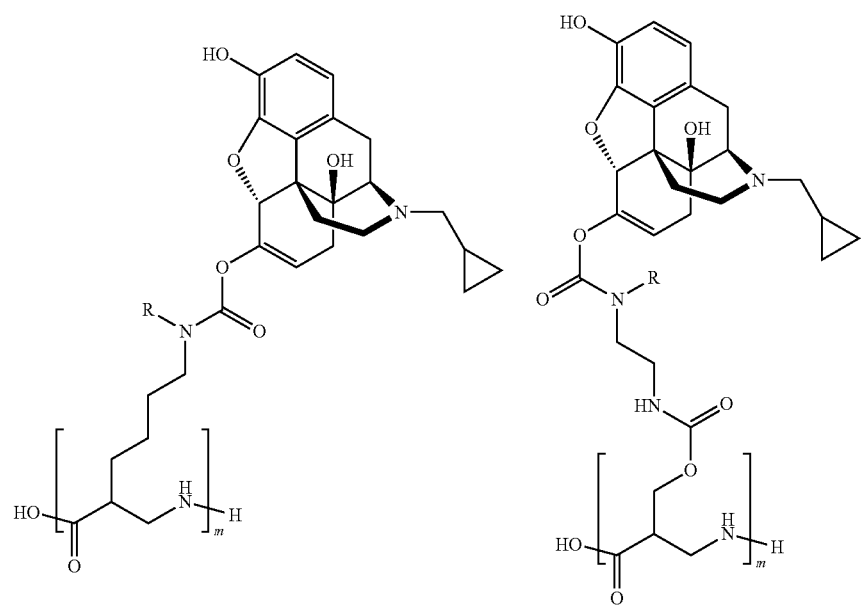

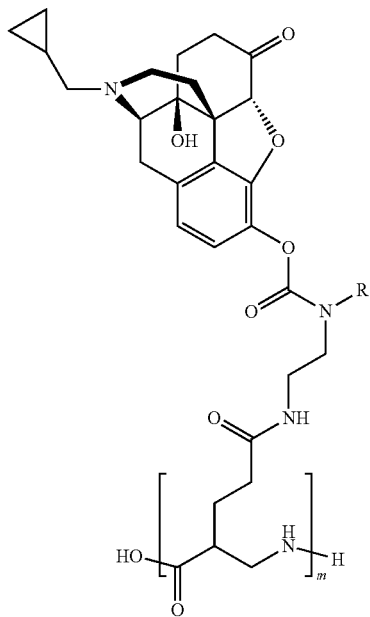
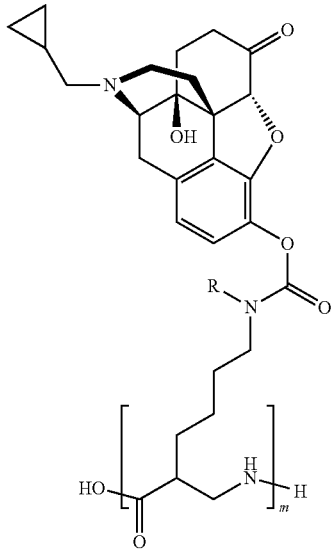
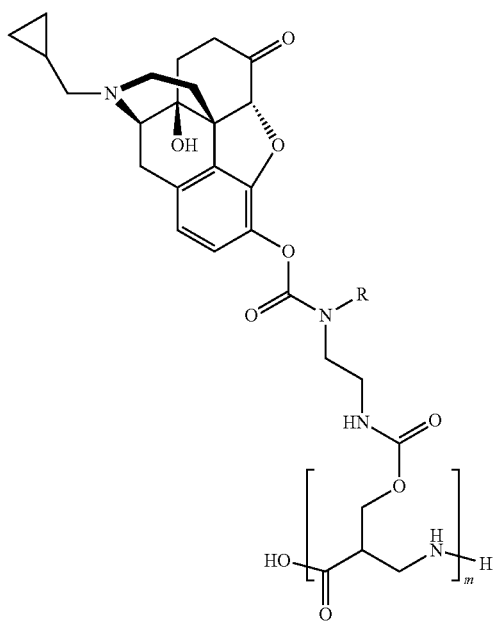
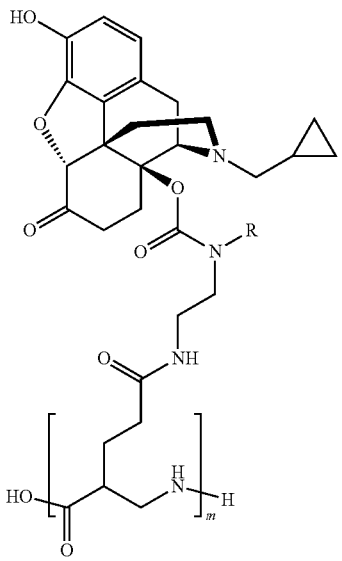

-continued
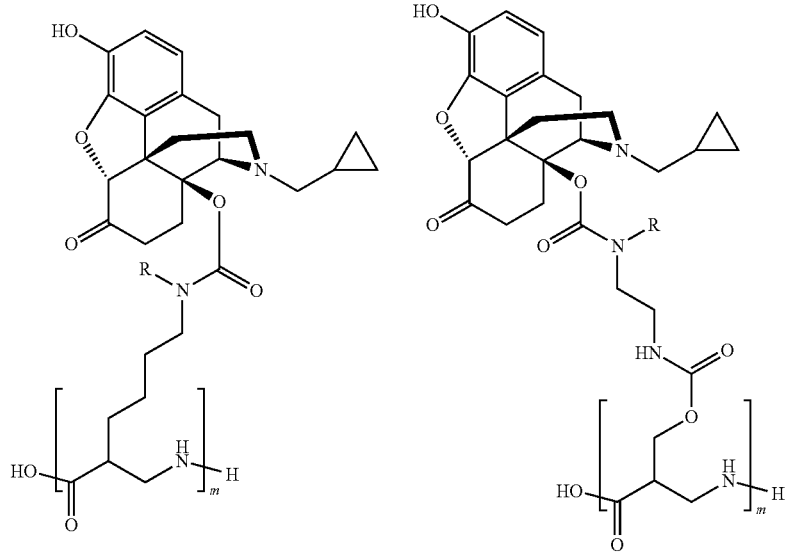
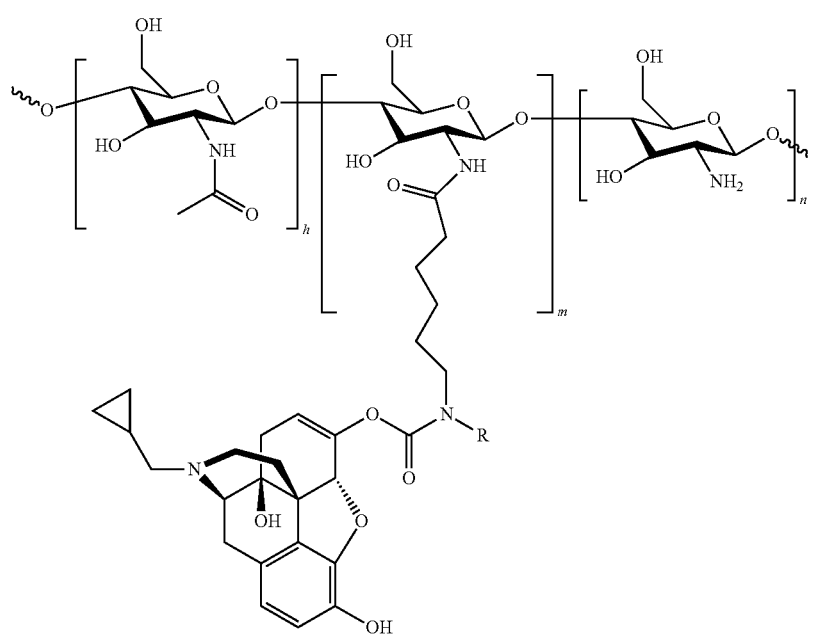

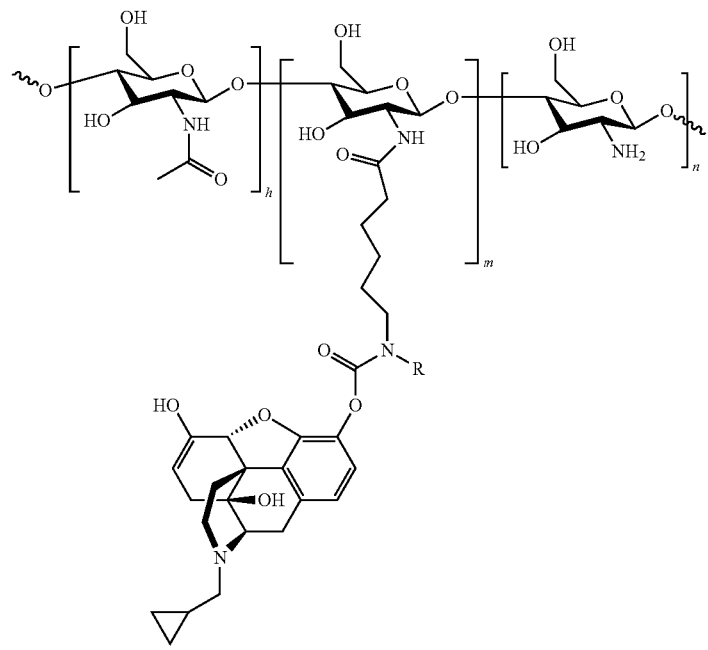
-continued
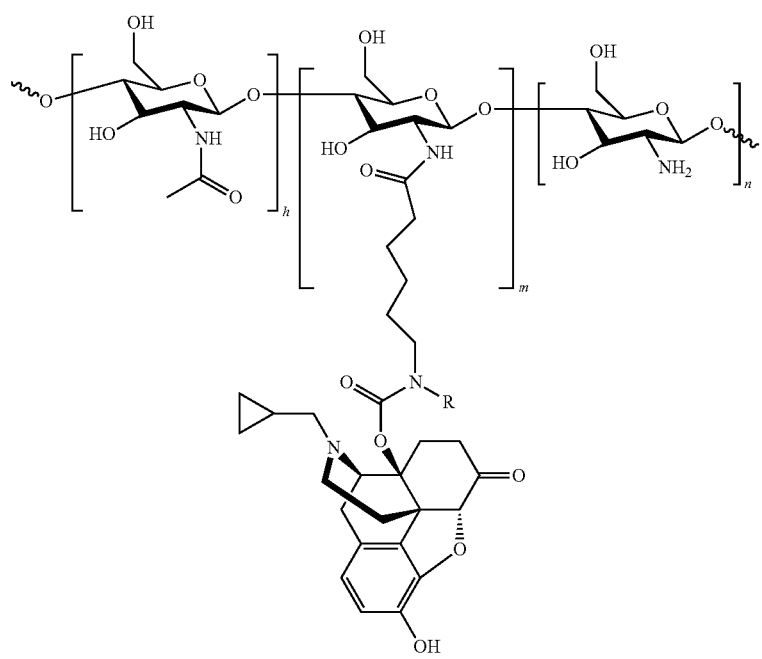

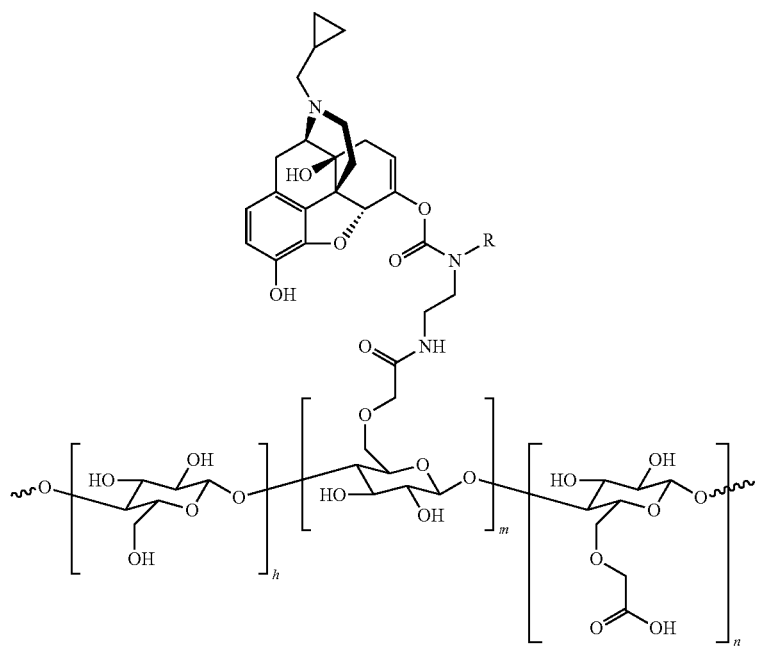
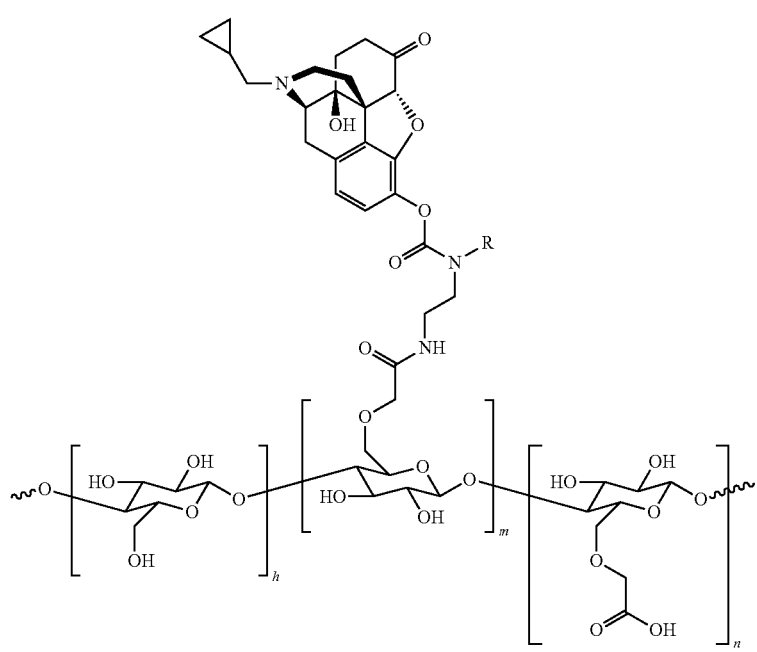

-continued

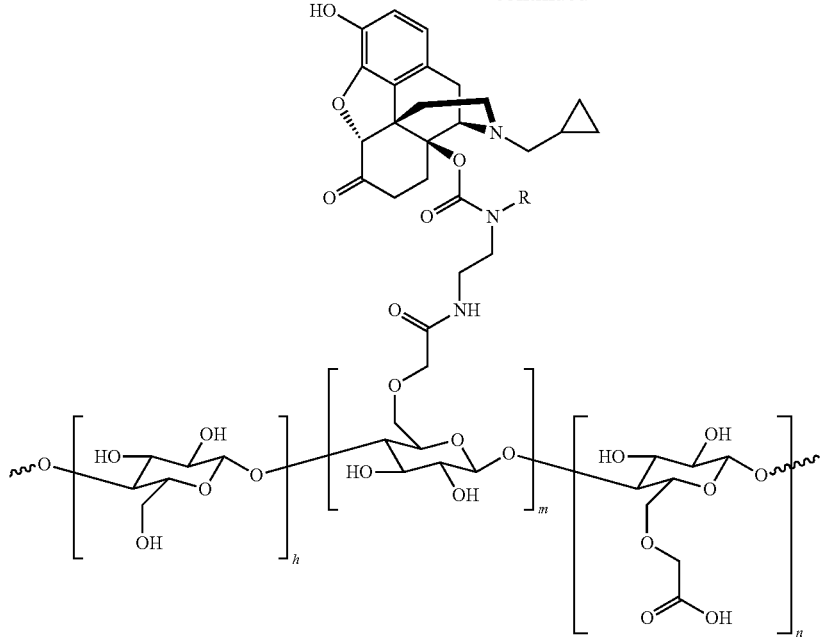

where R', R", m, and the values for n defining the length of the polyethylene glycol polymer are as defined above.

Exemplary antagonist-polymer conjugates, where the covalent bond is via a ketone group, a phenolic group, or a tertiary hydroxyl group of the opioid-antagonist, and the labile functionality is a carbamate that links the antagonist to the polymer are shown below. The opioid agonist is released via an intramolecular cyclization-release mechanism, where n is defined as above.

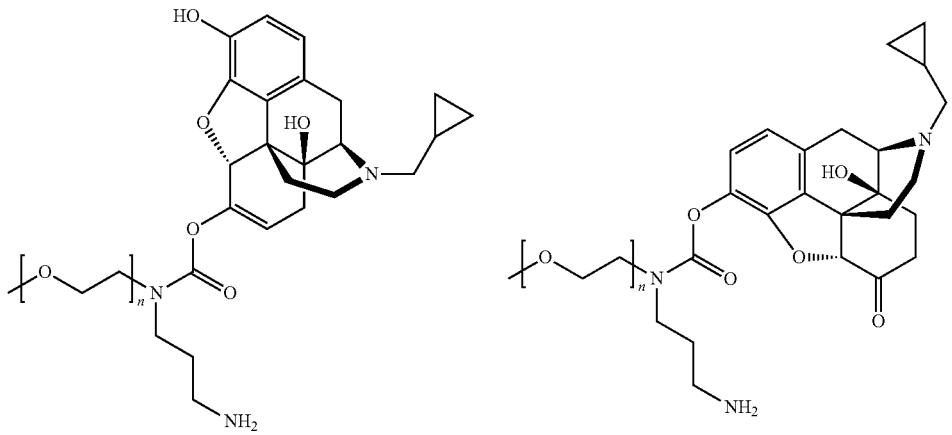

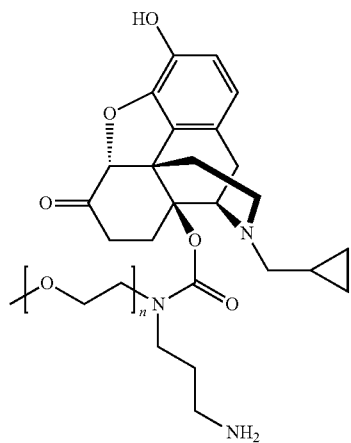
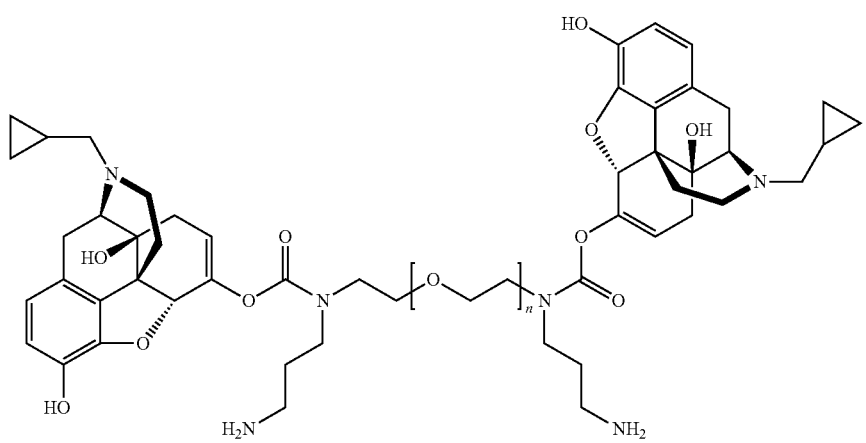
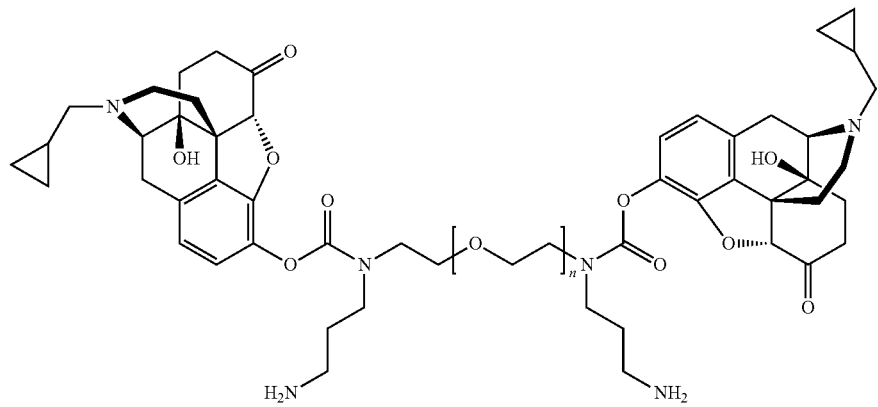

-continued

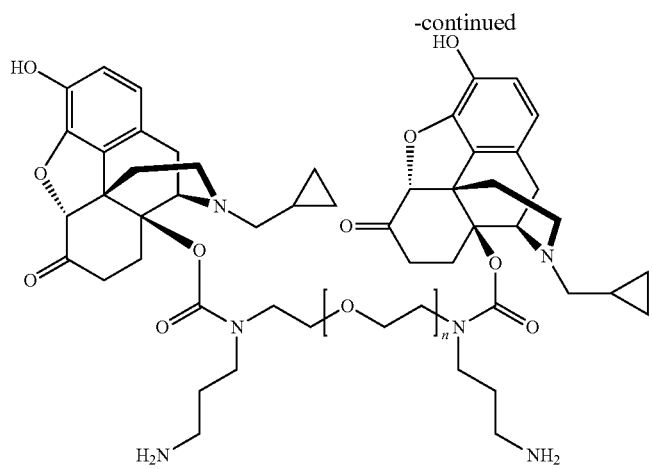

20

Exemplary antagonist-polymer conjugates, where the covalent bond is via a ketone group, a phenolic group, or a tertiary hydroxyl group of the opioid-antagonist, and the labile functionality is a carbonate that links the antagonist to the polymer are shown below, where the values for n defining the length of the polyethylene glycol polymer are as defined above.

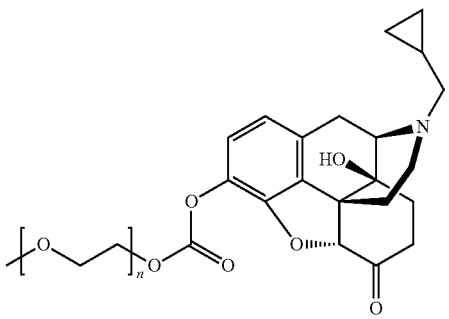

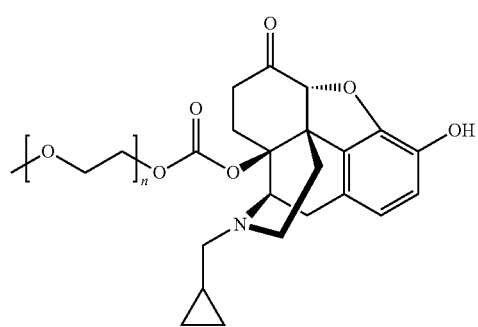

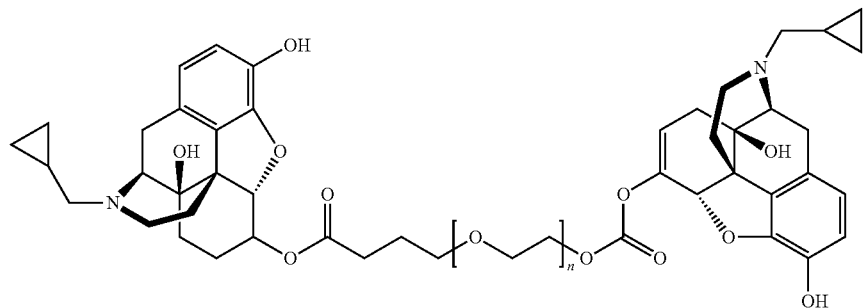

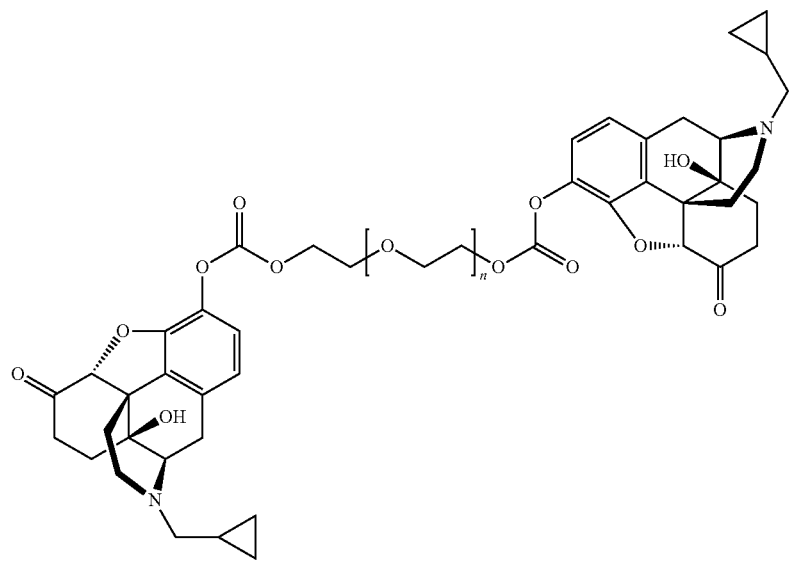
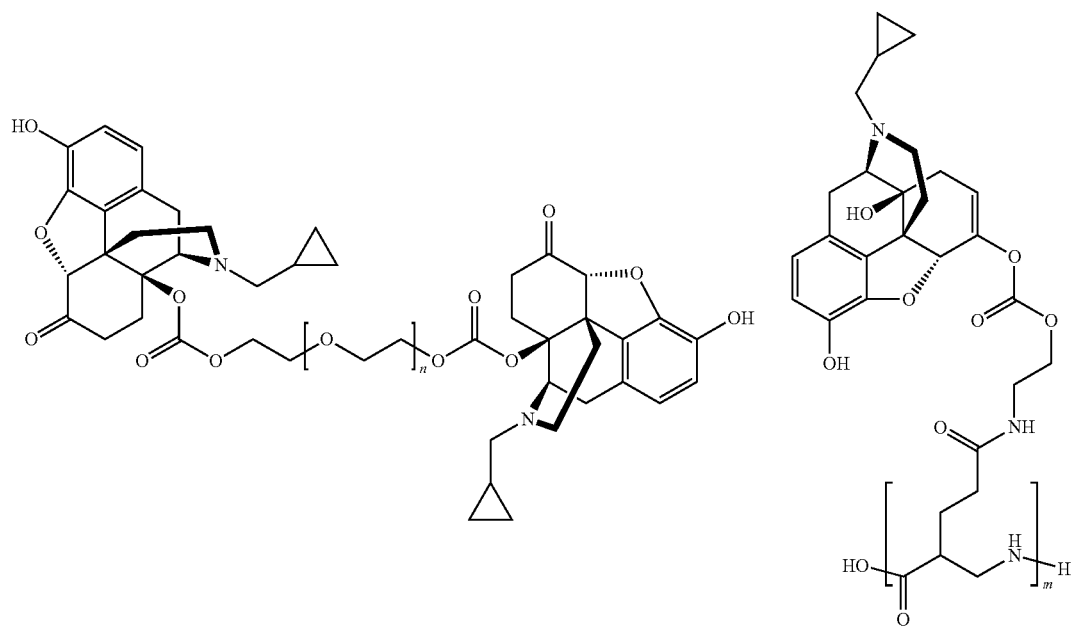

-continued
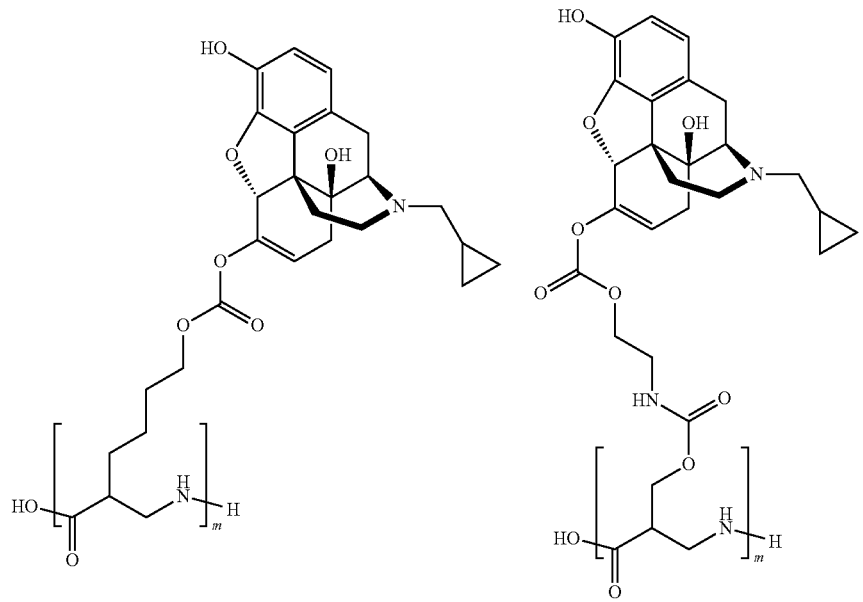
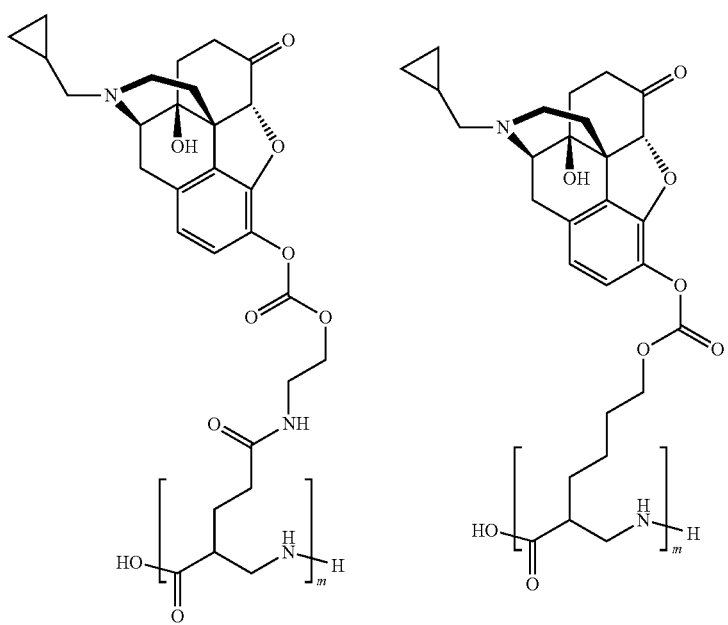

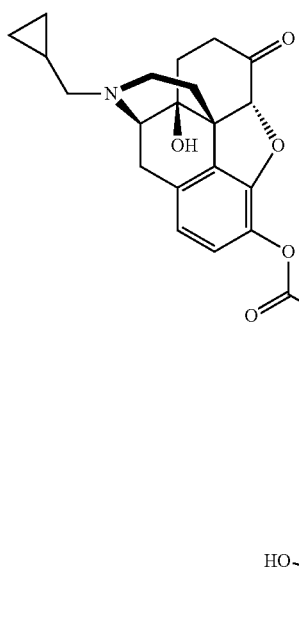
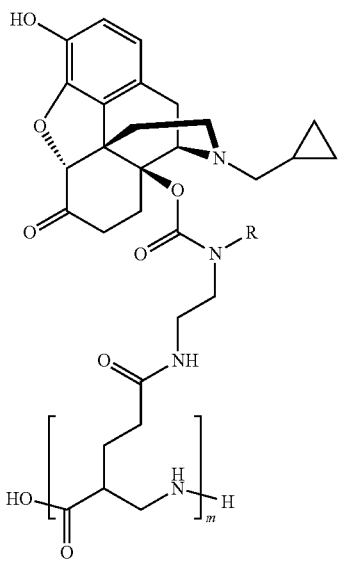
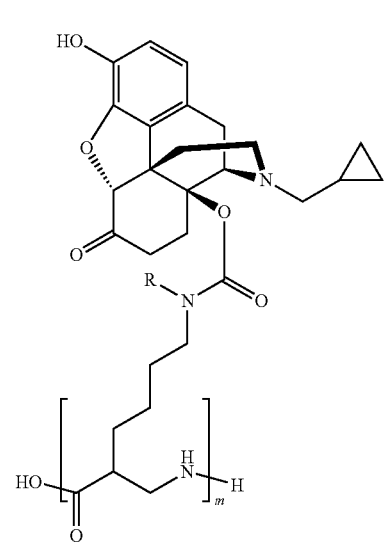
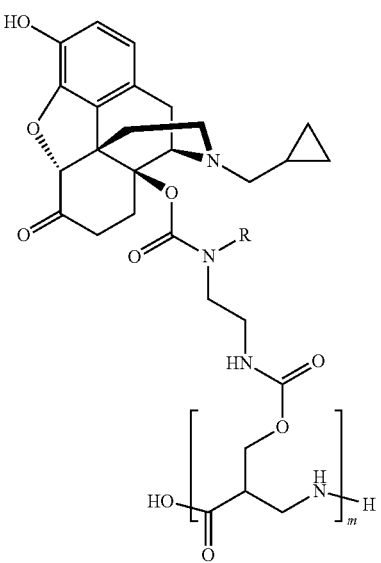

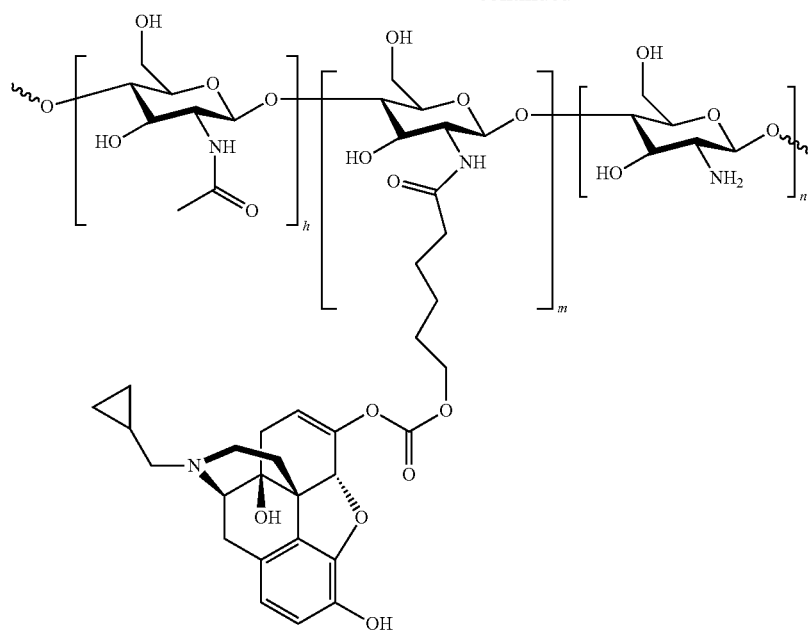
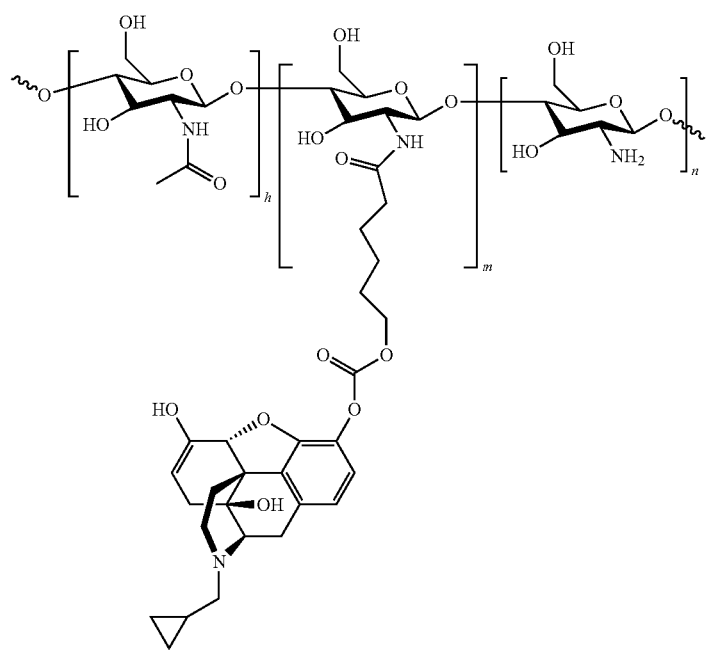

-continued
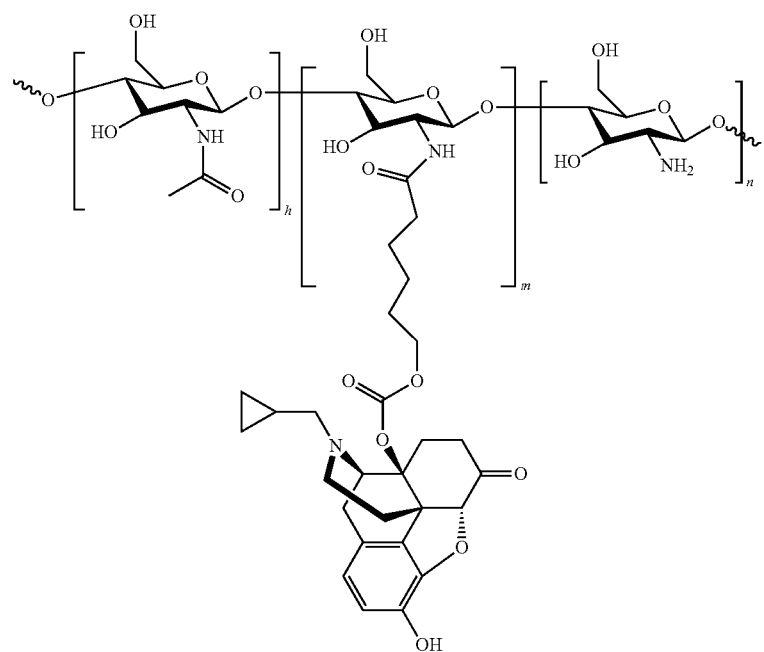
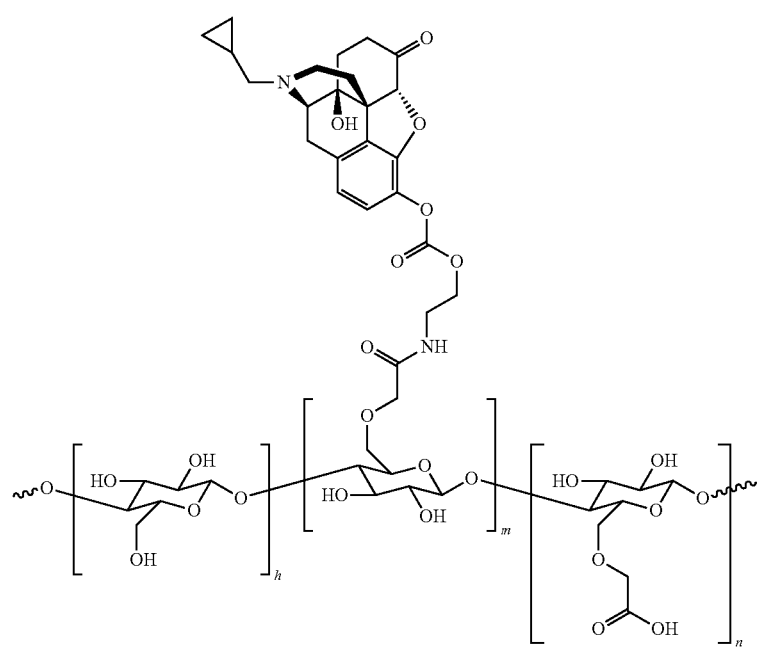

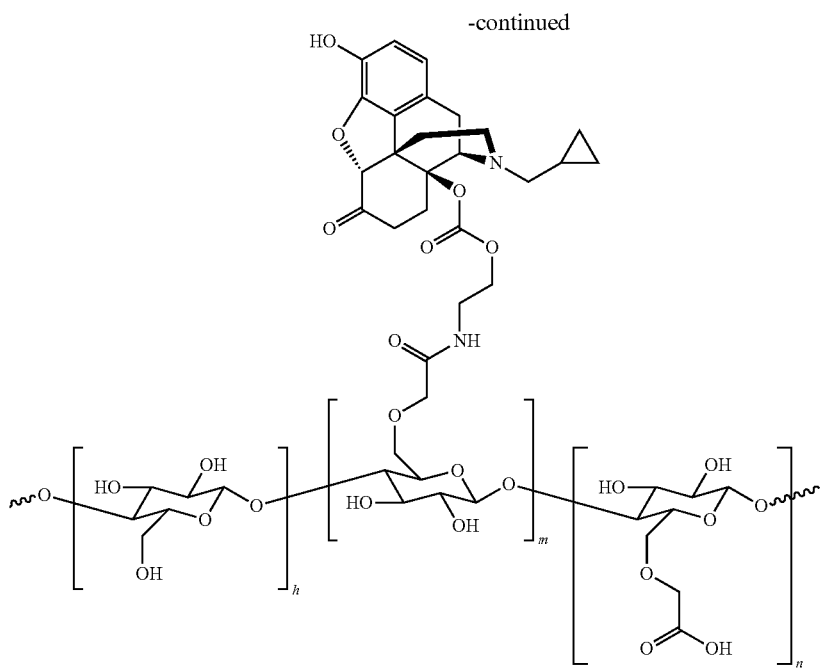

VII. Release of the Opioid Antagonist from the Opioid Antagonist-Polymer Conjugate As was described in detail above, the covalent bond between the polymer and the antagonist in the opioid antagonist-polymer conjugate is preferably physiologically stable enough so that the opioid antagonist is not significantly released from the polymer following oral administration to a patient. Rather, the covalent bond between the polymer and the antagonist in the opioid antagonist-polymer conjugate is preferably broken over a well-defined period of time within the dose form. The resulting accumulation of the released bioavailable antagonist in the dose form over time will attenuate, and eventually ablate, the effects of the co-formulated agonist, thereby reducing both abuse and diversion. Thus, the covalent bond between the polymer and the antagonist is subjected to conditions in the formulation such that it has a half-life of antagonist release that is about 0.5 y to about 5 y, more preferably about 1 y to about 3 y, or most preferably about 1.5 y to about 2.5 y. Thus, the half-life can be about 0.5 y, about 0.75 y, about 1.0 y, about 1.5 y, about 1.75 y, about 2 y, about 2.25 y, or about 2.5 y.

In one aspect of the invention, the bond between the polymer and the antagonist can be hydrolyzed under controlled conditions over a predetermined period of time, such as about 1.5 y, about 1.75 y, about 2 y, about 2.25 y, about 2.5 y or about 3 y. The bond can be hydrolyzed by the solvent, the co-solvent, or added nucleophile or catalyst selected to result in a rate of reaction that corresponds to the predetermined period of time. Additionally, buffers can be added to the co-formulation to modulate the reaction rate between the polymeric antagonist and nucleophiles that effect the release of the antagonist.

The half-life of an intermolecular or intramolecular reaction between the antagonist polymer conjugate and an extrinsic or appended nucleophile can also be tuned by modifying (i) the intrinsic nucleophilicity or basicity of the nucleophile and/or the amount of nucleophile relative to the polymer-antagonist conjugate, (ii) the internal pH of the formulation, and (iii) inclusion of Lewis acid catalysts (e.g magnesium salts) and/or suitable buffer systems. Thus, in one aspect of the invention, the opioid antagonist can be released from the polymer-antagonist conjugate via the action of a nucleophile, as illustrated below, where D is the antagonist:

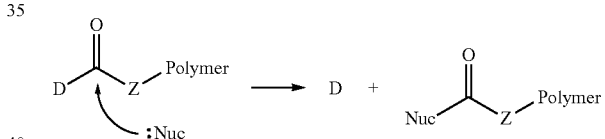

In another aspect of the invention, the opioid antagonist can be released from the polymer-antagonist conjugate via an elimination reaction, as illustrated below:

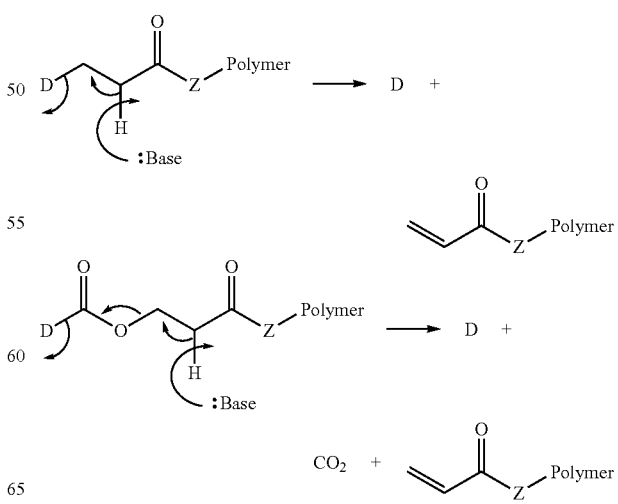

In one aspect of the invention, a buffer mediates the rate of the elimination reaction. In another aspect of the invention, a Lewis acid/base can be added to act as a catalyst for the elimination reaction. The buffer and/or catalyst is selected such that rate of elimination corresponds to a predetermined period of time, such as about 0.5 y, 1.5 y, about 1.75 y, about 2 y, about 2.25 y, about 2.5 y or about 3 y.

VIII. Formulations

Also embraced within this invention is a class of pharmaceutical compositions comprising one or more compounds identified using the method described above in association with one or more non-toxic, pharmaceutically acceptable carriers and/or diluents and/or adjuvants (collectively referred to herein as "carrier" materials) and, if desired, other active ingredients. The compounds of the present invention can be administered by any suitable route, preferably in the form of a pharmaceutical composition adapted to such a route, and in a dose effective for the treatment intended. The compounds and composition can, for example, be administered orally, transdermally, subcutaneously, rectally, or topically.

For oral administration, the pharmaceutical composition can be in the form of, for example, a tablet, capsule, a soft gelatin (softgel) capsule, a hard gelatin capsule, suspension or liquid. The pharmaceutical composition is preferably made in the form of a dosage unit containing a particular amount of the active ingredient. Examples of such dosage units are tablets or softgel capsules. The active ingredient can also be administered by injection as a composition wherein, for example, saline, dextrose or water can be used as a suitable carrier.

Soft gelatin capsules can be prepared in which capsules contain a mixture of the agonist, the opioid antagonist-polymer conjugate, and oleaginous and/or non-aqueous, and/or water miscible solvents such as polyethylene glycol and the like. Hydrophilic solvents compatible with softgel capsules can include PEG400, PEG800, ethanol, glycerin, PPG, polysorbates, povidone (PVP), Lubrasol®, Labrafac® and the like containing up to about 1-12% water. The softgel capsules can optionally contain a buffer, a co-solvent, or a nucleophile. Hard gelatin capsules can contain mixtures of the agonist, the polymer-antagonist conjugate in combination with a solid, pulverulent carrier, such as, for example, lactose, saccharose, sorbitol, mannitol, potato starch, corn starch, amylopectin, cellulose derivatives, or gelatin.

The amount of therapeutically active compound that is administered and the dosage regimen for treating a disease condition with the compounds and/or compositions of this invention depends on a variety of factors, including the age, weight, sex and medical condition of the subject, the severity of the pain, the route and frequency of administration, and the particular compound employed, and thus may vary widely. The pharmaceutical compositions may contain the opioid agonist in the range of about 0.1 to 2000 mg, preferably in the range of about 0.5 to 500 mg and most preferably between about 1 and 100 mg. A daily dose of about 0.001 mg/kg to 100 mg/kg body weight, may be appropriate. The daily dose can be administered in one to four doses per day. The concentration of the opioid antagonist-polymer conjugate is selected such that at a pre-selected expiry date of the composition, the molar ratio of the agonist to delivered antagonist is in the range of about 0.5:1 to about 10:1, preferably about 0.5:1 to about 2:1.

For therapeutic purposes, the compounds of this invention are ordinarily combined with one or more excipients appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved or suitably emulsified in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Unit Dosage Forms

A dose unit form, softgel capsule, or composition of the disclosure can be designed to provide an analgesic effect to a subject for a defined period of time. The amount of opioid antagonist within a compound, softgel, or dose unit that becomes bioavailable over time can be determined based on in vitro or in vivo calculations and experiments.

An opioid agonist described herein and a compound of formula I $(D-X-Z)_m-P$ can each independently be present in a unit dosage form of the invention in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, from about 950 mg to about 1000 mg, from about 1000 mg to about 1050 mg, from about 1050 mg to about 1100 mg, from about 1100 mg to about 1150 mg, from about 1150 mg to about 1200 mg, from about 1200 mg to about 1250 mg, from about 1250 mg to about 1300 mg, from about 1300 mg to about 1350 mg, from about 1350 mg to about 1400 mg, from about 1400 mg to about 1450 mg, from about 1450 mg to about 1500 mg, from about 1500 mg to about 1550 mg, from about 1550 mg to about 1600 mg, from about 1600 mg to about 1650 mg, from about 1650 mg to about 1700 mg, from about 1700 mg to about 1750 mg, from about 1750 mg to about 1850 mg, from about 1850 mg to about 1900 mg, from about 1900 mg to about 1950 mg, from about 1950 mg to about 2000 mg, from about 2000 mg to about 2050 mg, from about 2050 mg to about 2100 mg, from about 2100 mg to about 2150 mg, from about 2150 mg to about 2200 mg, from about 2200 mg to about 2250 mg, from about 2250 mg to about 2300 mg, from about 2300 mg to about 2350 mg, from about 2350 mg to about 2400 mg, from about 2400 mg to about 2450 mg, or from about 2450 mg to about 2500 mg.

The mass of a compound described herein can be present in a composition in an amount of about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, or about 2500 mg.

The following are non-limiting examples of molar ratios of an opioid agonist described herein and a compound of formula I $(D-X-Z)_m-P$, such as a compound A. The molar ratio can be: about 20:about 1; about 19.9:about 1; about 19.8:about 1; about 19.7:about 1; about 19.6:about 1; about 19.5:about 1; about 19.4:about 1; about 19.3:about 1; about 19.2:about 1; about 19.1:about 1; about 19:about 1; about 18.9:about 1; about 18.8:about 1; about 18.7:about 1; about 18.6:about 1; about 18.5:about 1; about 18.4:about 1; about 18.3:about 1; about 18.2:about 1; about 18.1:about 1; about 18:about 1; about 17.9:about 1; about 17.8:about 1; about 17.7:about 1; about 17.6:about 1; about 17.5:about 1; about 17.4:about 1; about 17.3:about 1; about 17.2:about 1; about 17.1:about 1; about 17:about 1; about 16.9:about 1; about 16.8:about 1; about 16.7:about 1; about 16.6:about 1; about 16.5:about 1; about 16.4:about 1; about 16.3:about 1; about 16.2:about 1; about 16.1:about 1; about 16:about 1; about 15.9 about 1; about 15.8 about 1; about 15.7:about 1; about 15.6:about 1; about 15.5:about 1; about 15.4:about 1; about 15.3:about 1; about 15.2:about 1; about 15.1:about 1; about 15:about 1; about 14.9:about 1; about 14.8:about 1; about 14.7:about 1; about 14.6:about 1; about 14.5:about 1; about 14.4:about 1; about 14.3:about 1; about 14.2:about 1; about 14.1:about 1; about 14:about 1; about 13.9:about 1; about 13.8:about 1; about 13.7:about 1; about 13.6:about 1; about 13.5:about 1; about 13.4 about 1; about 13.3:about 1; about 13.2:about 1; about 13.1:about 1; about 13:about 1; about 12.9:about 1; about 12.8:about 1; about 12.7:about 1; about 12.6:about 1; about 12.5:about 1; about 12.4:about 1; about 12.3:about 1; about 12.2:about 1; about 12.1:about 1; about 12:about 1; about 11.9:about 1; about 11.8:about 1; about 11.7:about 1; about 11.6:about 1; about 11.5:about 1; about 11.4:about 1; about 11.3:about 1; about 11.2:about 1; about 11.1:about 1; about 11:about 1; about 10.9:about 1; about 10.8:about 1; about 10.7:about 1; about 10.6:about 1; about 10.5:about 1; about 10.4:about 1; about 10.3:about 1; about 10.2:about 1; about 10.1:about 1; about 10:about 1; about 9.9:about 1; about 9.8:about 1; about 9.7:about 1; about 9.6:about 1; about 9.5:about 1; about 9.4:about 1; about 9.3:about 1; about 9.2:about 1; about 9.1:about 1; about 9:about 1; about 8.9:about 1; about 8.8:about 1; about 8.7:about 1; about 8.6 about 1; about 8.5:about 1; about 8.4:about 1; about 8.3:about 1; about 8.2:about 1; about 8.1: about 1; about 8:about 1; about 7.9:about 1; about 7.8:about 1; about 7.7:about 1; about 7.6:about 1; about 7.5:about 1; about 7.4:about 1; about 7.3:about 1; about 7.2:about 1; about 7.1:about 1; about 7:about 1; about 6.9:about 1; about 6.8:about 1; about 6.7:about 1; about 6.6:about 1; about 6.5:about 1; about 6.4:about 1; about 6.3:about 1; about 6.2:about 1; about 6.1:about 1; about 6:about 1; about 5.9:about 1; about 5.8:about 1; about 5.7:about 1; about 5.6:about 1; about 5.5:about 1; about 5.4:about 1; about 5.3:about 1; about 5.2:about 1; about 5.1:about 1; about 5:about 1; about 4.9:about 1; about 4.8:about 1; about 4.7:about 1; about 4.6:about 1; about 4.5:about 1; about 4.4:about 1; about 4.3:about 1; about 4.2:about 1; about 4.1:about 1; about 4:about 1; about 3.9:about 1; about 3.8:about 1; about 3.7:about 1; about 3.6:about 1; about 3.5:about 1; about 3.4:about 1; about 3.3:about 1; about 3.2:about 1; about 3.1:about 1; about 3:about 1; about 2.9:about 1; about 2.8:about 1; about 2.7:about 1; about 2.6:about 1; about 2.5:about 1; about 2.4:about 1; about 2.3:about 1; about 2.2:about 1; about 2.1:about 1; about 2:about 1; about 1.9:about 1; about 1.8:about 1; about 1.7:about 1; about 1.6:about 1; about 1.5:about 1; about 1.4:about 1; about 1.3:about 1; about 1.2:about 1; about 1.1:about 1; or about 1:about 1.

Pharmacokinetics and Pharmacodynamics

The self-expiring (auto-expiring) dose unit, composition, or softgel of the invention can release a therapeutically-effective amount of an opioid for a first period of time; and an amount of an opioid antagonist for a defined second period of time.

A unit dosage, softgel, or composition of the disclosure can provide an opioid agonist and a compound of Formula I described herein to provide a therapeutically-effective (i.e., analgesic) plasma concentration of an opioid agonist for a first period of time. A first period of time can be from the day of manufacture (day 0) up to 3 months, up to 4 months, up to 5 months, up to 6 months, up to 7 months, up to 8 months, up to 9 months, up to 10 months, up to 11 months, up to 12 months, up to 13 months, up to 14 months, up to 15 months, up to 16 months, up to 17 months, up to 18 months, up to 19 months, up to 20 months, up to 21 months, up to 22 months, up to 23 months, up to 24 months, up to 25 months, up to 26 months, up to 27 months, up to 28 months, up to 29 months, up to 30 months, up to 31 months, up to 32 months, up to 33 months, up to 34 months, up to 35 months, or up to 36 months.

A unit dosage, softgel, or composition of the disclosure can provide an effective plasma concentration of an opioid antagonist for a second period of time after manufacture. A second period of time can start from about 3 months to about 4 months, from about 3 months to about 5 months, from about 3 months to about 6 months, from about 3 months to about 7 months, from about 3 months to about 8 months, from about 3 months to about 9 months, from about 3 months to about 10 months, from about 3 months to about 11 months, from about 3 months to about 12 months, from about 3 months to about 13 months, from about 3 months to about 14 months, from about 3 months to about 15 months, from about 3 months to about 16 months, from about 3 months to about 17 months, from about 3 months to about 18 months, from about 3 months to about 19 months, from about 3 months to about 20 months, from about 3 months to about 21 months, from about 3 months to about 22 months, from about 3 months to about 23 months, from about 3 months to about 24 months, from about 3 months to about 25 months, from about 3 months to about 26 months, from about 3 months to about 27 months, from about 3 months to about 28 months, from about 3 months to about 29 months, from about 3 months to about 30 months, from about 3 months to about 31 months, from about 3 months to about 32 months, from about 3 months to about 33 months, from about 3 months to about 34 months, from about 3 months to about 35 months, or from about 3 months to about 36 months.

In some cases, a second period of time can start from about 6 months to about 7 months, from about 6 months to about 8 months, from about 6 months to about 9 months, from about 6 months to about 10 months, from about 6 months to about 11 months, from about 6 months to about 12 months, from about 6 months to about 13 months, from about 6 months to about 14 months, from about 6 months to about 15 months, from about 6 months to about 16 months, from about 6 months to about 17 months, from about 6 months to about 18 months, from about 6 months to about 19 months, from about 6 months to about 20 months, from about 6 months to about 21 months, from about 6 months to about 22 months, from about 6 months to about 23 months, from about 6 months to about 24 months, from about 6 months to about 25 months, from about 6 months to about 26 months, from about 6 months to about 27 months, from about 6 months to about 28 months, from about 6 months to about 29 months, from about 6 months to about 30 months, from about 6 months to about 31 months, from about 6 months to about 32 months, from about 6 months to about 33 months, from about 6 months to about 34 months, from about 6 months to about 35 months, or from about 6 months to about 36 months.

In other cases, a second period of time can start from about 12 months to about 13 months, from about 12 months to about 14 months, from about 12 months to about 15 months, from about 12 months to about 16 months, from about 12 months to about 17 months, from about 12 months to about 18 months, from about 12 months to about 19 months, from about 12 months to about 20 months, from about 12 months to about 21 months, from about 12 months to about 22 months, from about 12 months to about 23 months, from about 12 months to about 24 months, from about 12 months to about 25 months, from about 12 months to about 26 months, from about 12 months to about 27 months, from about 12 months to about 28 months, from about 12 months to about 29 months, from about 12 months to about 30 months, from about 12 months to about 31 months, from about 12 months to about 32 months, from about 12 months to about 33 months, from about 12 months to about 34 months, from about 12 months to about 35 months, or from about 12 months to about 36 months.

In yet other cases, a second period of time can be from about 18 months to about 19 months, from about 18 months to about 20 months, from about 18 months to about 21 months, from about 18 months to about 22 months, from about 18 months to about 23 months, from about 18 months to about 24 months, from about 18 months to about 25 months, from about 18 months to about 26 months, from about 18 months to about 27 months, from about 18 months to about 28 months, from about 18 months to about 29 months, from about 18 months to about 30 months, from about 18 months to about 31 months, from about 18 months to about 32 months, from about 18 months to about 33 months, from about 18 months to about 34 months, from about 18 months to about 35 months, or from about 18 months to about 36 months.

In addition, a second period of time can be from about 24 months to about 25 months, from about 24 months to about 26 months, from about 24 months to about 27 months, from about 24 months to about 28 months, from about 24 months to about 29 months, from about 24 months to about 30 months, from about 24 months to about 31 months, from about 24 months to about 32 months, from about 24 months to about 33 months, from about 24 months to about 34 months, from about 24 months to about 35 months, or from about 24 months to about 36 months.

A concentration can be the amount of the opioid agonist or an opioid antagonist in a given volume of plasma. A composition, softgel, or dose unit of the invention can provide a peak plasma concentration ($C_{max}$) of an opioid agonist or of an opioid antagonist described herein after administration. A $C_{max}$ can be provided by one or more dose units of the invention, alone or in combination. A mean $C_{max}$ can be of about 500 pg/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 21 ng/mL, about 22 ng/mL, about 23 ng/mL, about 24 ng/mL, about 25 ng/mL, about 26 ng/mL, about 27 ng/mL, about 28 ng/mL, about 29 ng/mL, about 30 ng/mL, about 31 ng/mL, about 32 ng/mL, about 33 ng/mL, about 34 ng/mL, about 35 ng/mL, about 36 ng/mL, about 37 ng/mL, about 38 ng/mL, about 39 ng/mL, about 40 ng/mL, about 41 ng/mL, about 42 ng/mL, about 43 ng/mL, about 44 ng/mL, about 45 ng/mL, about 46 ng/mL, about 47 ng/mL, about 48 ng/mL, about 49 ng/mL, about 50 ng/mL, about 51 ng/mL, about 52 ng/mL, about 53 ng/mL, about 54 ng/mL, about 55 ng/mL, about 56 ng/mL, about 57 ng/mL, about 58 ng/mL, about 59 ng/mL, about 60 ng/mL, about 61 ng/mL, about 62 ng/mL, about 63 ng/mL, about 64 ng/mL, about 65 ng/mL, about 66 ng/mL, about 67 ng/mL, about 68 ng/mL, about 69 ng/mL, about 70 ng/mL, about 71 ng/mL, about 72 ng/mL, about 73 ng/mL, about 74 ng/mL, about 75 ng/mL, about 76 ng/mL, about 77 ng/mL, about 78 ng/mL, about 79 ng/mL, about 80 ng/mL, about 81 ng/mL, about 82 ng/mL, about 83 ng/mL, about 84 ng/mL, about 85 ng/mL, about 86 ng/mL, about 87 ng/mL, about 88 ng/mL, about 89 ng/m, about 90 ng/mL, about 91 ng/mL, about 92 ng/mL, about 93 ng/mL, about 94 ng/mL, about 95 ng/mL, about 96 ng/mL, about 97 ng/mL, about 98 ng/mL, about 99 ng/mL, about 100 ng/mL, about 101 ng/mL, about 102 ng/mL, about 103 ng/mL, about 104 ng/mL, about 105 ng/mL, about 106 ng/mL, about 107 ng/mL, about 108 ng/mL, about 109 ng/mL, about 110 ng/mL, about 111 ng/mL, about 112 ng/mL, about 113 ng/mL, about 114 ng/mL, about 115 ng/mL, about 116 ng/mL, about 117 ng/mL, about 118 ng/mL, about 119 ng/mL, about 120 ng/mL, about 121 ng/mL, about 122 ng/mL, about 123 ng/mL, about 124 ng/mL, about 125 ng/mL, about 126 ng/mL, about 127 ng/mL, about 128 ng/mL, about 129 ng/mL, about 130 ng/mL, about 131 ng/mL, about 132 ng/mL, about 133 ng/mL, about 134 ng/mL, about 135 ng/mL, about 136 ng/mL, about 137 ng/mL, about 138 ng/mL, about 139 ng/mL, about 140 ng/mL, about 141 ng/mL, about 142 ng/mL, about 143 ng/mL, about 144 ng/mL, about 145 ng/mL, about 146 ng/mL, about 147 ng/mL, about 148 ng/mL, about 149 ng/mL, about 150 ng/mL, about 151 ng/mL, about 152 ng/mL, about 153 ng/mL, about 154 ng/mL, about 155 ng/mL, about 156 ng/mL, about 157 ng/mL, about 158 ng/mL, about 159 ng/mL, about 160 ng/mL, about 161 ng/mL, about 162 ng/mL, about 163 ng/mL, about 164 ng/mL, about 165 ng/mL, about 166 ng/mL, about 167 ng/mL, about 168 ng/mL, about 169 ng/mL, about 170 ng/mL, about 171 ng/mL, about 172 ng/mL, about 173 ng/mL, about 174 ng/mL, about 175 ng/mL, about 176 ng/mL, about 177 ng/mL, about 178 ng/mL, about 179 ng/mL, about 180 ng/mL, about 181 ng/mL, about 182 ng/mL, about 183 ng/mL, about 184 ng/mL, about 185 ng/mL, about 186 ng/mL, about 187 ng/mL, about 188 ng/mL, about 189 ng/mL, about 190 ng/mL, about 191 ng/mL, about 192 ng/mL, about 193 ng/mL, about 194 ng/mL, about 195 ng/mL, about 196 ng/mL, about 197 ng/mL, about 198 ng/mL, about 199 ng/mL, or about 200 ng/mL, a suitable range of the mean values provided herein.

A mean $C_{max}$ can be of about 50 pg/mL to about 250 pg/mL, from about 250 pg/mL to about 500 pg/mL, from about 500 pg/mL to about 750 pg/mL, from about 750 pg/mL to about 1000 pg/mL, from about 1000 pg/mL to about 1250 pg/mL, from about 1250 pg/mL to about 1500 pg/mL, from about 1500 pg/mL to about 1750 pg/mL, from about 1750 pg/mL to about 2000 pg/mL, from about 2000 pg/mL to about 2250 pg/mL, from about 2250 pg/mL to about 2500 pg/mL, from about 2500 pg/mL to about 2750 pg/mL, from about 2750 pg/mL to about 3000 pg/mL, from about 3000 pg/mL to about 3250 pg/mL, from about 3250 pg/mL to about 3500 pg/mL, from about 3500 pg/mL to about 3750 pg/mL, from about 4000 pg/mL to about 4250 pg/mL, from about 4250 pg/mL to about 4500 pg/mL, from about 4500 pg/mL to about 4750 pg/mL, or from about 4750 pg/mL to about 5000 pg/mL.

A composition, softgel, or dose unit of the invention can provide a plasma concentration of a compound described herein that is defined by a plasma Area Under the Curve (AUC). An AUC can provide a plasma compound concentration-time curve, thereby identifying the exposure of a subject to a self-expiring pill that has "expired" or not. The $AUC_{0-24}$ of a compound described herein can range from about 1 pg/mL*h to about 10,000 ng/mL*h, from about 10 pg/mL*h to about 1,000 ng/mL*h, from about 0.1 ng/mL*h to about 1,000 ng/mL*h, 0.5 ng/mL*h to about 500 ng/mL*h, or from about 0.1 ng/mL*h to about 100 ng/mL*h.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental errors and deviations should, of course, be allowed for.

Example 1: Synthesis of Product 1

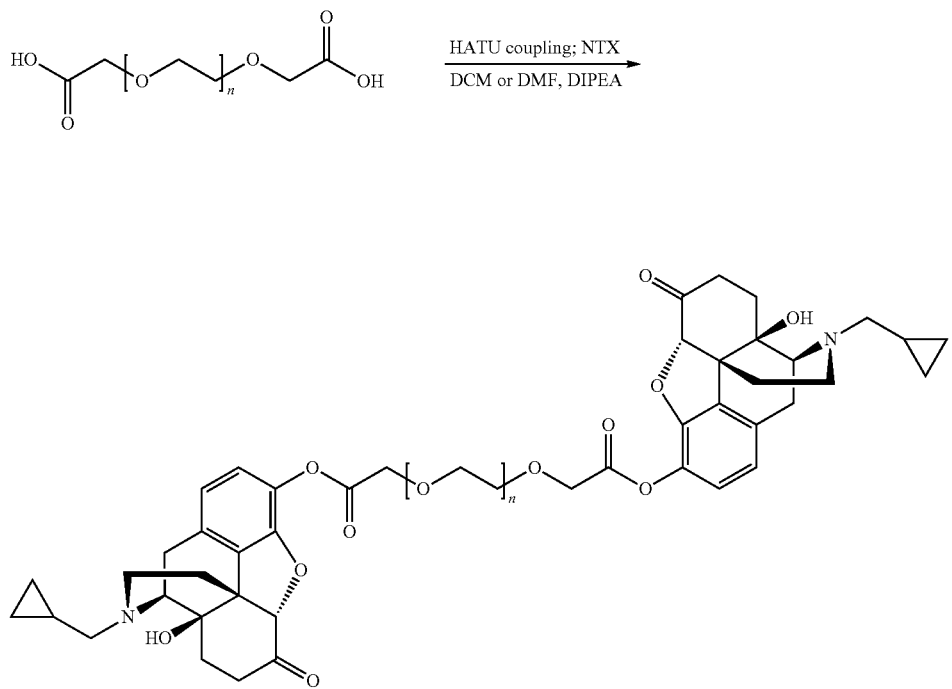

1

To a solution of PEG-5000 dicarboxylic acid (10 mmol) in DMF (20 mL) was added naltrexone (22 mmol), DIPEA (40 mmol) and N-hydroxyazabenzotriazole (HATU) (22 mmol). The reaction mixture was stirred at RT overnight. The reaction mixture was diluted with EtOAc (60 mL) and the organic layer was washed successively with water (50 mL), saturated aqueous NaHCO$_3$ (50 mL) and brine (50 mL). The organic layer was separated, dried over Na$_2$SO$_4$, and concentrated to give crude product 1. Purification by flash column chromatography provides isolated product 1.

Example 2: Synthesis of Product 2

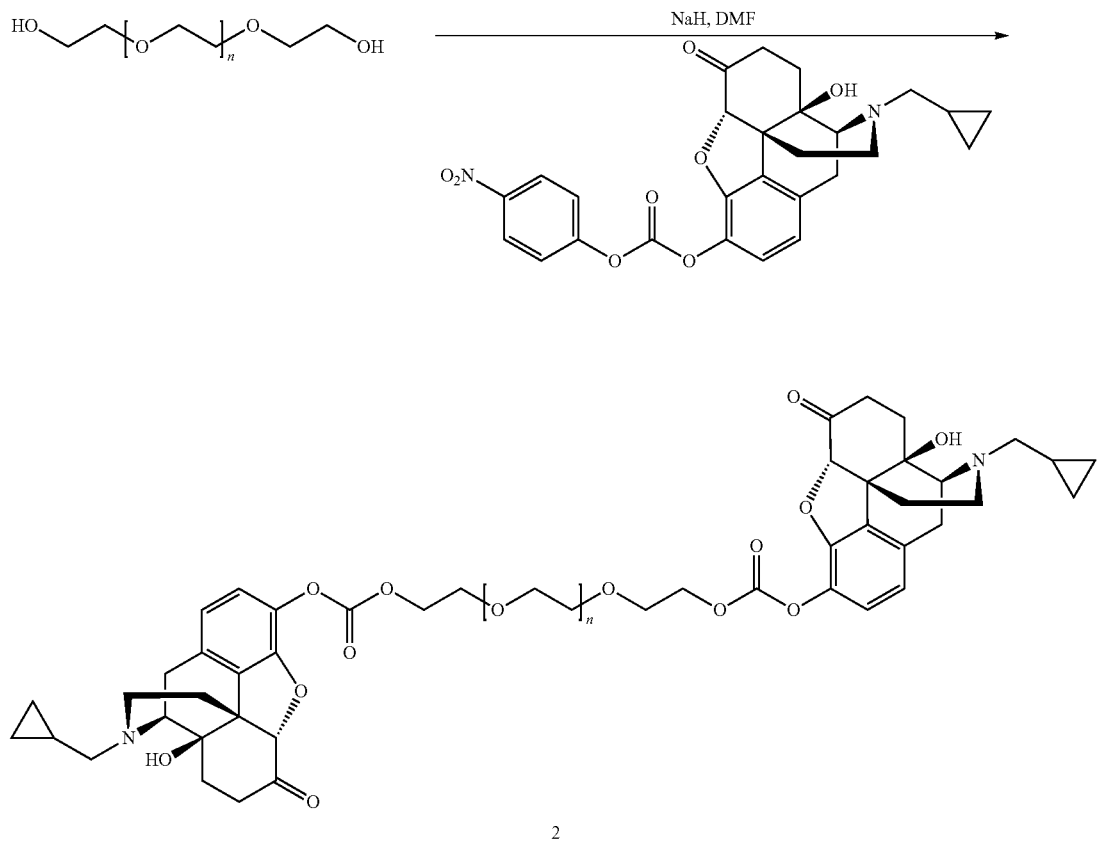

Naltrexone (74 mmol) and DIEA (8 mmol) is suspended in dichloromethane (50 mL). p-Nitrophenylchloroformate (8 mmol) in dichloromethane (50 mL) is then added dropwise over a period of 5 minutes. The reaction mixture is then sonicated for 2 hours to afford a stock solution of the activated naltrexone that is used in the next step.

To a solution of PEG-5000 (10 mmol) in DMF (20 mL) was added sodium hydride (22 mmol) and allowed to stir until hydrogen gas evolution stops. Next, activated naltrexone p-nitrophenylcarbonate (22 mmol) is added dropwise. The reaction mixture was stirred at RT overnight. The reaction mixture was diluted with EtOAc (60 mL) and the organic layer was washed successively with water (50 mL), saturated aqueous NaHCO$_3$ (50 mL) and brine (50 mL). The organic layer was separated, dried over Na$_2$SO$_4$, and concentrated to give crude product 2. Purification by flash column chromatography provides isolated product 2.

Example 3: Synthesis of Product 3

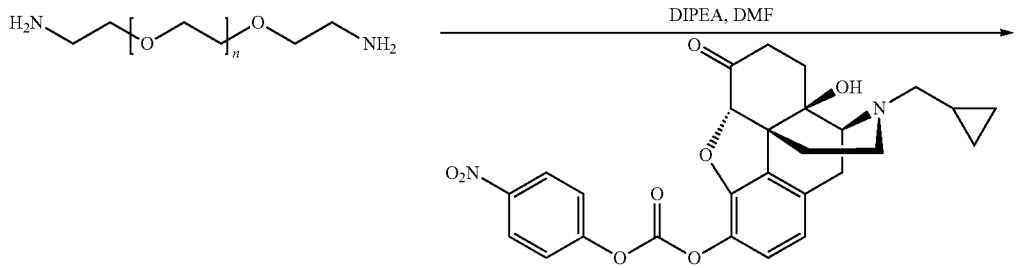

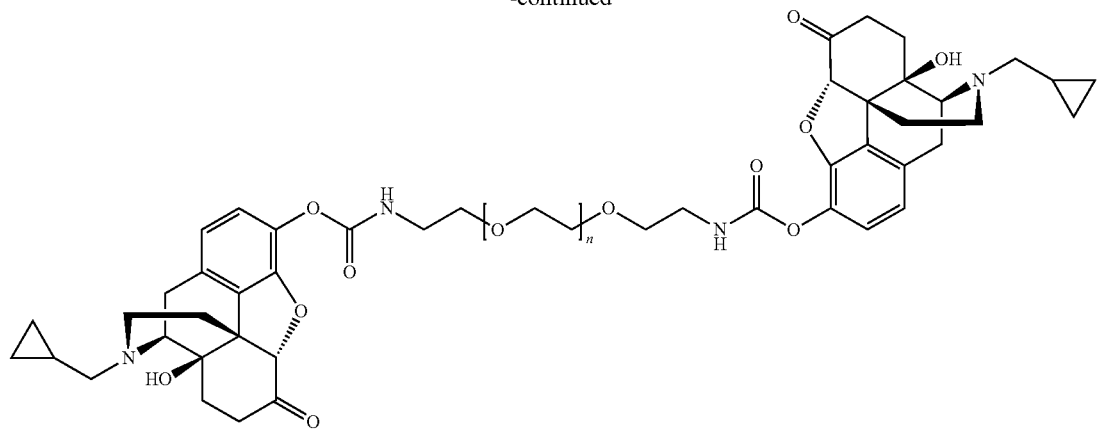

3

PEG-5000 diamine (10 mmol) and diisopropylethylamine (30 mmol) are dissolved in DMF (5 mL) and then activated naltrexone (21 mmol) is added dropwise. The solution is stirred for 5 hours. The solvent is evaporated under vacuum. The reaction mixture was dissolved into EtOAc (60 mL) and the organic layer was washed successively with water (50 mL), saturated aqueous $NaHCO_3$ (50 mL) and brine (50 mL). The organic layer was separated, dried over $Na_2SO_4$, and concentrated to give crude product 3. Purification by flash column chromatography provides isolated product 3.

Example 4: Synthesis of Product 4

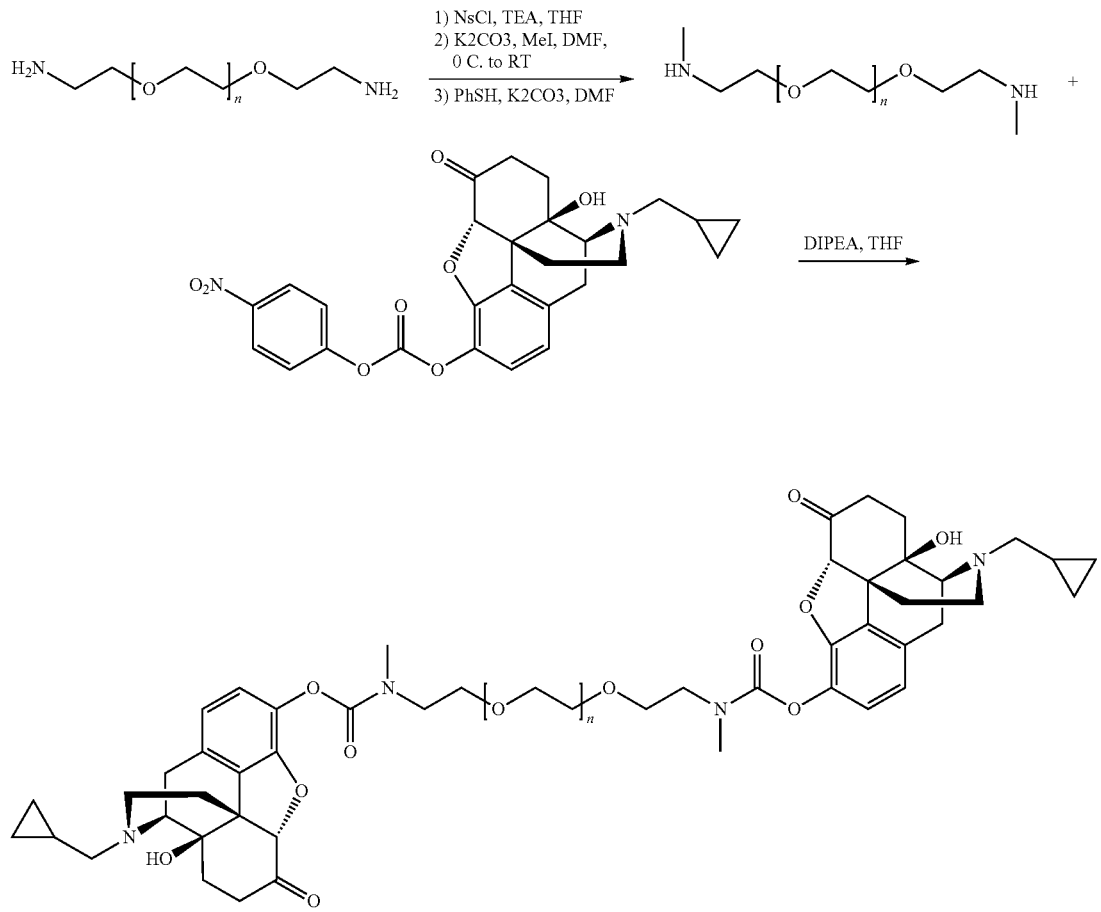

4

To an ice chilled solution (0° C.) of PEG-5000 diamine (10 mmol) in THF (20 mL) was added nosyl chloride (22 mmol) and TEA (40 mmol). The reaction mixture was stirred at RT for 15 h. The reaction mixture was diluted with EtOAc (60 mL) and the organic layer was washed successively with water (50 mL), saturated aqueous NaHCO$_3$ (50 mL) and brine (50 mL). The organic layer was separated, dried over Na$_2$SO$_4$, and concentrated to give crude PEG-5000 di-nosylamine. Purification by flash column chromatography provides isolated PEG-5000 di-nosylamine.

To a solution of PEG-5000 di-nosylamine (10 mmol) in DMF (25 mL) at room temperature was added K$_2$CO$_3$ (40 mmol) in one portion. The mixture was cooled in an ice water bath to 0° C. MeI (39 mmol) was added in small portions via syringe over 10 min. The resulting mixture was allowed to warm to room temperature over 30 min and stirring was continued for 3 h. The reaction mixture was diluted with EtOAc (100 mL) and the organic layer was washed successively with water (100 mL), saturated aqueous NaHCO$_3$ (100 mL) and brine (100 mL). The organic layer was separated, dried over Na$_2$SO$_4$, and concentrated to give crude PEG-5000 di-methylnosylamine. Purification by flash column chromatography provides isolated PEG-5000 di-methylnosylamine.

To a solution containing PEG-5000 di-methylnosylamine (5 mmol) in DMF (15 mL) was cooled in an ice bath to 0° C. The to mixture was added thiophenol (10 mmol). The mixture was allowed to warm to room temperature and was stirred for 6 h. Water (15 mL) was added. The reaction mixture was extracted with EtOAc (3×20 mL). The combined EtOAc extracts were washed successively with water (100 mL), saturated aqueous NaHCO$_3$ (100 mL) and brine (100 mL). The organic layer was separated, dried over Na$_2$SO$_4$, and concentrated to give crude PEG-5000 di-methylamine. Purification by flash column chromatography provides isolated PEG-5000 di-methylamine.

PEG-5000 di-methylamine (5 mmol) and diisopropylethylamine (15 mmol) are dissolved in DMF (5 mL) and then activated naltrexone (11 mmol) is added. The solution is stirred for 5 hours. The solvent is evaporated under vacuum, The reaction mixture was dissolved into EtOAc (30 mL) and the organic layer was washed successively with water (25 mL), saturated aqueous NaHCO$_3$ (25 mL) and brine (25 mL). The organic layer was separated, dried over Na$_2$SO$_4$, and concentrated to give crude product 4. Purification by flash column chromatography provides isolated product 4.

Example 5: Synthesis of Product 5

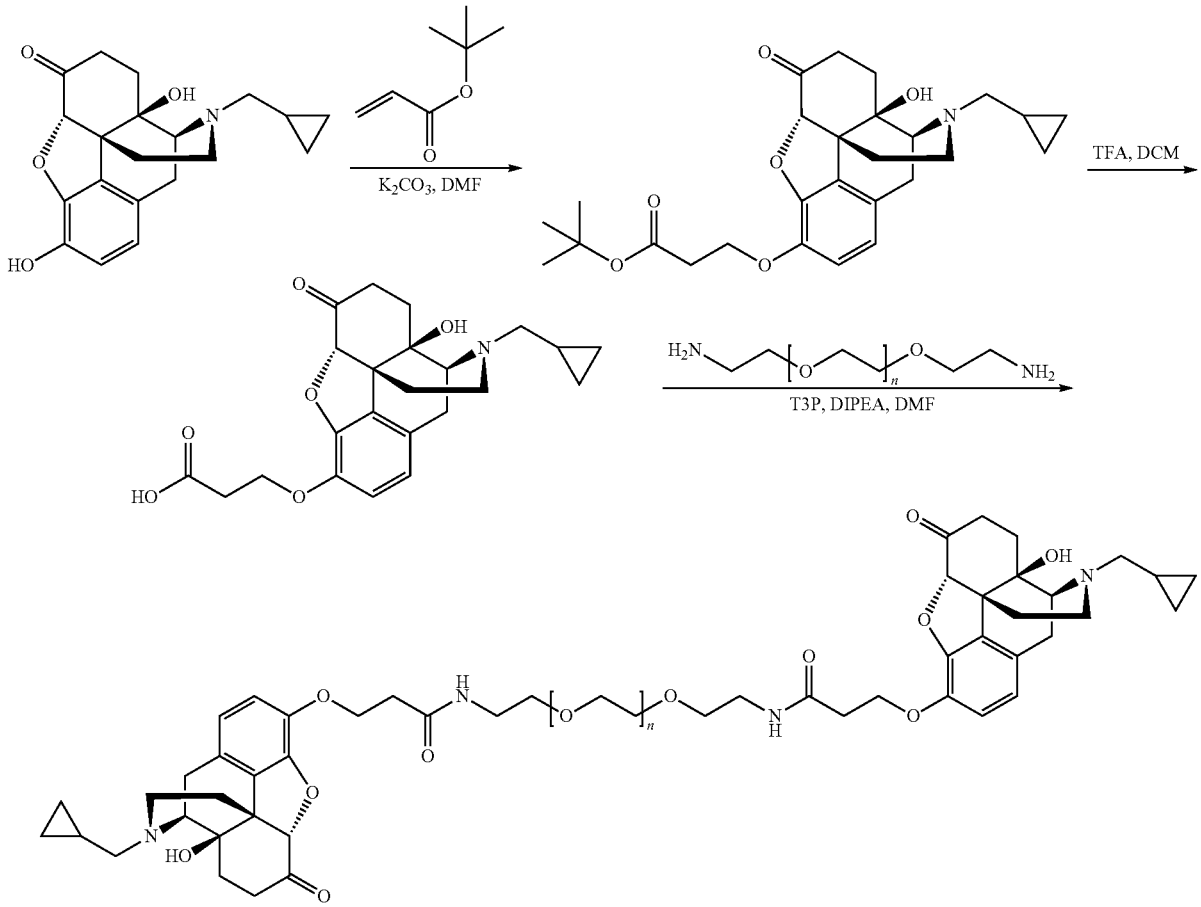

5

To a solution of Naltrexone (10 mmol) and K$_2$CO$_3$ (30 mmol) are dissolved in DMF (5 mL) and tert-butyl acrylate (12 mmol) is added dropwise. The solution is stirred for 5 hours at 60° C. The reaction is cooled to room temperature and then the solvent is evaporated under vacuum. The reaction mixture was dissolved into EtOAc (60 mL) and the organic layer was washed successively with water (50 mL), saturated aqueous NaHCO₃ (50 mL) and brine (50 mL). The organic layer was separated, dried over Na₂SO₄, and concentrated to give crude naltrexone phenolic ester. The material was purified by silica gel chromatography.

To a solution of naltrexone phenolic ester (10 mmol) in DCM (10 mL) was added TFA (1 mL) and the reaction mixture was allowed to stir for 1 h. Next the reaction was condensed under vacuum and then dissolved into EtOAc (25 mL) and the organic layer was washed successively with water (50 mL), saturated aqueous NaHCO₃ (50 mL) and brine (50 mL). The organic layer was separated, dried over Na₂SO₄, and concentrated to give crude phenolic acid which was used directly in the next step without purification.

To a solution of PEG-5000 diamine (10 mmol) in DMF (20 mL) was added phenolic acid (22 mmol), DIPEA (60 mmol) and N-hydroxyazabenzotriazole (HATU) (22 mmol). The reaction mixture was stirred at RT overnight. The reaction mixture was diluted with EtOAc (100 mL) and the organic layer was washed successively with water (100 mL), saturated aqueous NaHCO₃ (100 mL) and brine (100 mL). The organic layer was separated, dried over Na₂SO₄, and concentrated to give crude product 5. Purification by flash column chromatography provides isolated product 5.

Example 6: Synthesis of Product 6

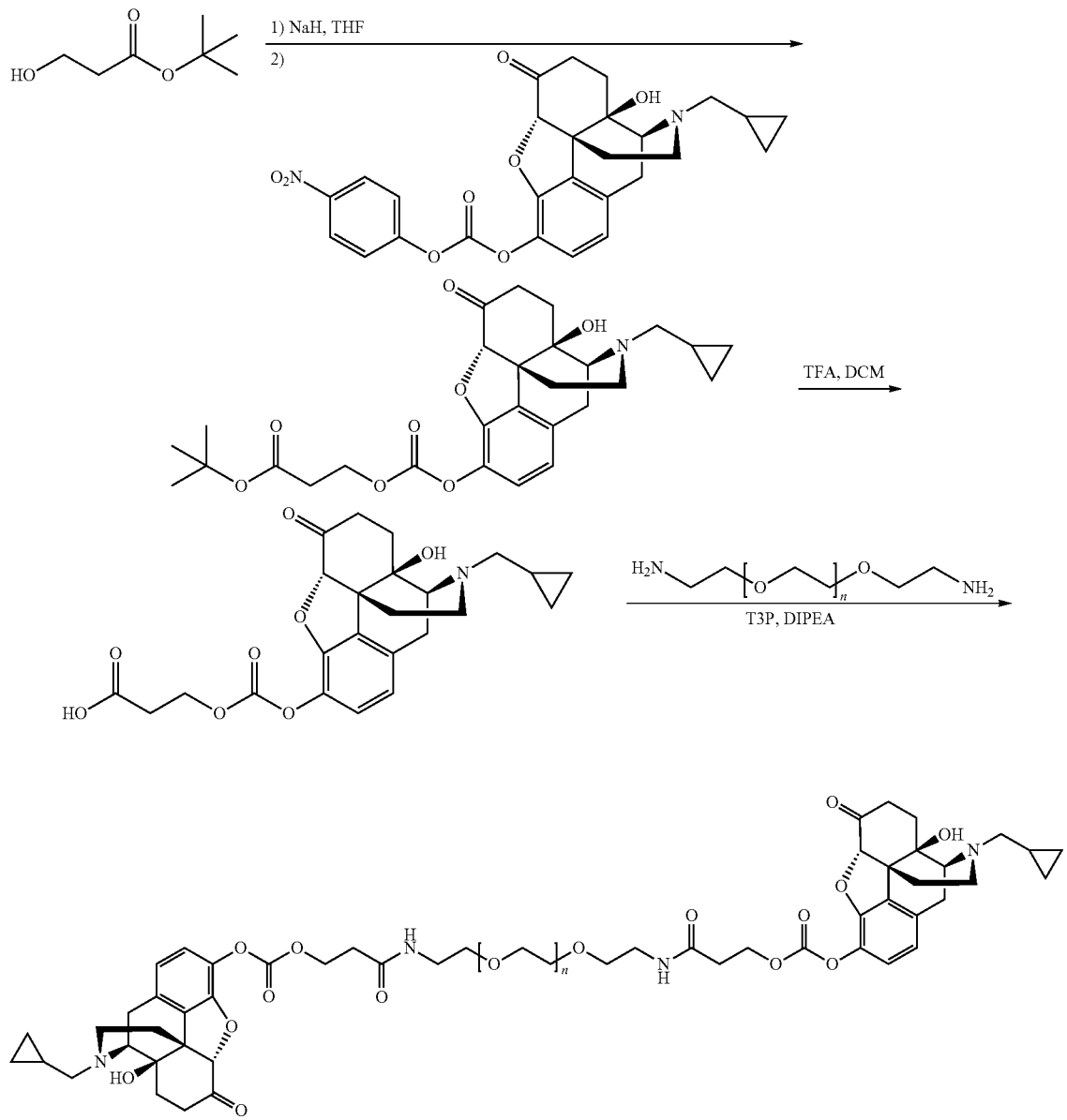

Activation of NTX (Phenol)

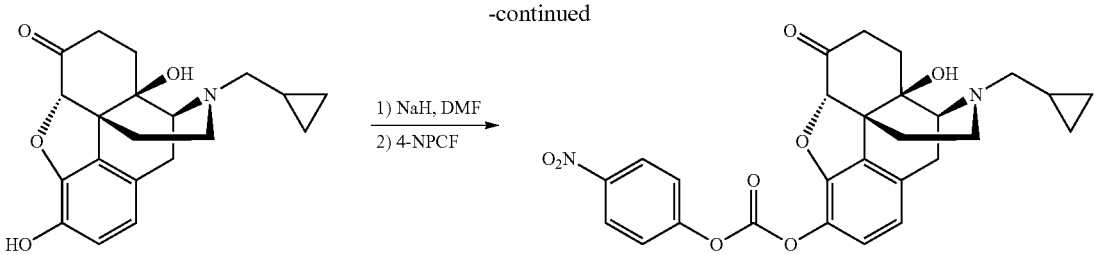

To a solution of tert-Butyl 3-hydroxypropionate (10 mmol) in THF (5 mL) was added NaH (12 mmol). The solution is stirred until evolution of hydrogen gas ceases. Next, activated naltrexone (12 mmol) is added in one portion. The solution is stirred for 5 h at room temperature. The solvent is evaporated under vacuum, The reaction mixture was dissolved into EtOAc (60 mL) and the organic layer was washed successively with water (50 mL), saturated aqueous NaHCO₃ (50 mL) and brine (50 mL). The organic layer was separated, dried over Na₂SO₄, and concentrated to give crude naltrexone carbonate ester which was purified by flash column chromatography.

To a solution of naltrexone carbonate ester (10 mmol) in DCM (10 mL) was added TFA (1 mL) and the reaction mixture was allowed to stir for 1 h. Next the reaction was condensed under vacuum and then dissolved into EtOAc (25 mL) and the organic layer was washed successively with water (50 mL), saturated aqueous NaHCO₃ (50 mL) and brine (50 mL). The organic layer was separated, dried over Na₂SO₄, and concentrated to give crude naltrexone carbonate acid which was used directly in the next step without purification.

To a solution of PEG-5000 diamine (10 mmol) in DMF (20 mL) was added naltrexone carbonate acid (22 mmol), DIPEA (60 mmol) and N-hydroxyazabenzotriazole (HATU) (22 mmol). The reaction mixture was stirred at RT overnight. The reaction mixture was diluted with EtOAc (100 mL) and the organic layer was washed successively with water (100 mL), saturated aqueous NaHCO₃ (100 mL) and brine (100 mL). The organic layer was separated, dried over Na₂SO₄, and concentrated to give crude product 6. Purification by flash column chromatography provides isolated product 6.

Example 7: Synthesis of Product 7

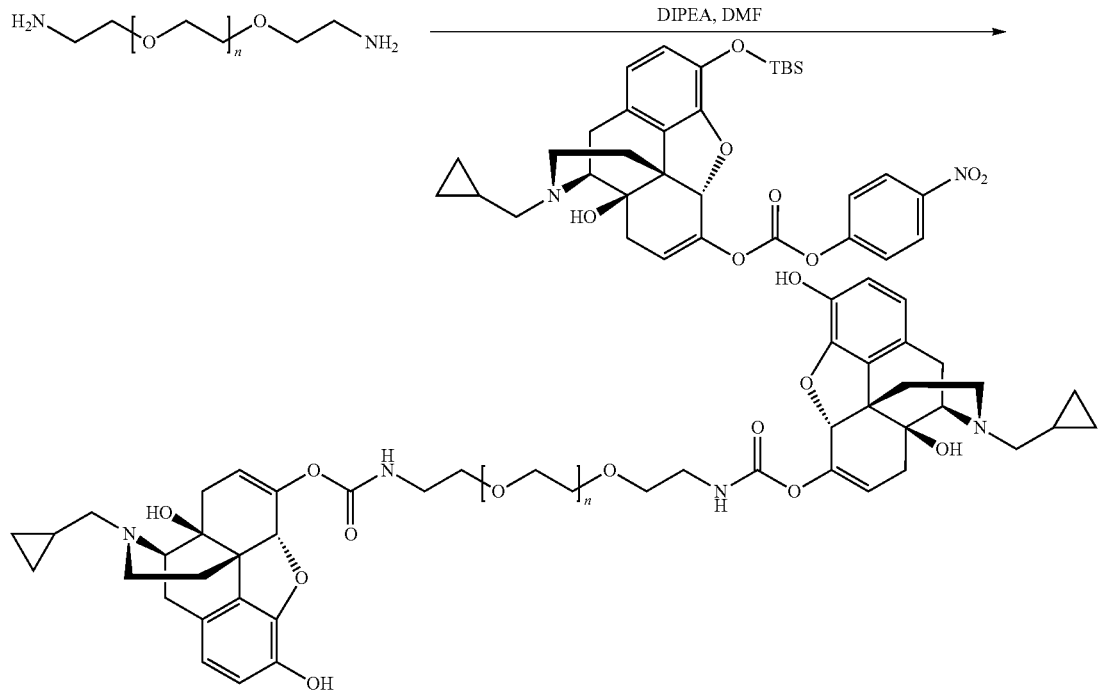

To a cooled (~5° C.) solution of Naltrexone free base (11.8 g, 36.0 mmol) in DMF (110 mL) is added imidazole (3.68 g, 54 mmol) and TBDMS-Cl (5.43 g, 36.0 mmol). Ten min after complete addition the bath is removed and the mixture stirred at ambient temperature for 16 h. Most of the DMF is removed in vacuo and the residue taken into EtOAc (600 mL), washed with water (2×500 mL) and brine (300 mL) and dried over MgSO₄. After evaporation of the solvent in vacuo, the crude material (white solid, 15 g) is purified by column chromatography ($SiO_2$ 330 g, 100% hexane, followed by gradient 0-80% EtOAc in hexane). Pure TBS protected naltrexone is isolated as a white solid.

To a cooled (−78° C.) solution of TBS protected naltrexone (5.31 g, 11.7 mmol) in anhydrous THF (200 mL) is added, under $N_2$, dropwise a 0.5 M solution of KHMDS in toluene over 25 min. The yellow solution is stirred at this temperature for 30 min. Then, the solution is added through a metal cannula to a cooled solution (−78° C.) of 4-nitrophenyl chloroformate (2.35 g, 11.7 mmol) in anhydrous THF (50 mL) over 5 min to give the activated TBS protected naltrexone.

PEG-5000 amine and activated TBS protected naltrexone, are coupled as described in Example 3. Subsequently, the TBS phenolic protecting group is removed via dissolving in THF (200 mL) and adding TBAF (1.0M in THF, 13 mmol). The mixture was allowed to stir for 6 h and then condensed under vacuum. The reaction mixture was diluted with EtOAc (200 mL) and the organic layer was washed successively with water (200 mL), saturated aqueous $NaHCO_3$ (200 mL) and brine (200 mL). The organic layer was separated, dried over $Na_2SO_4$, and concentrated to give crude product 9 which was purified by flash column chromatography.

Example 8: Synthesis of Compound A

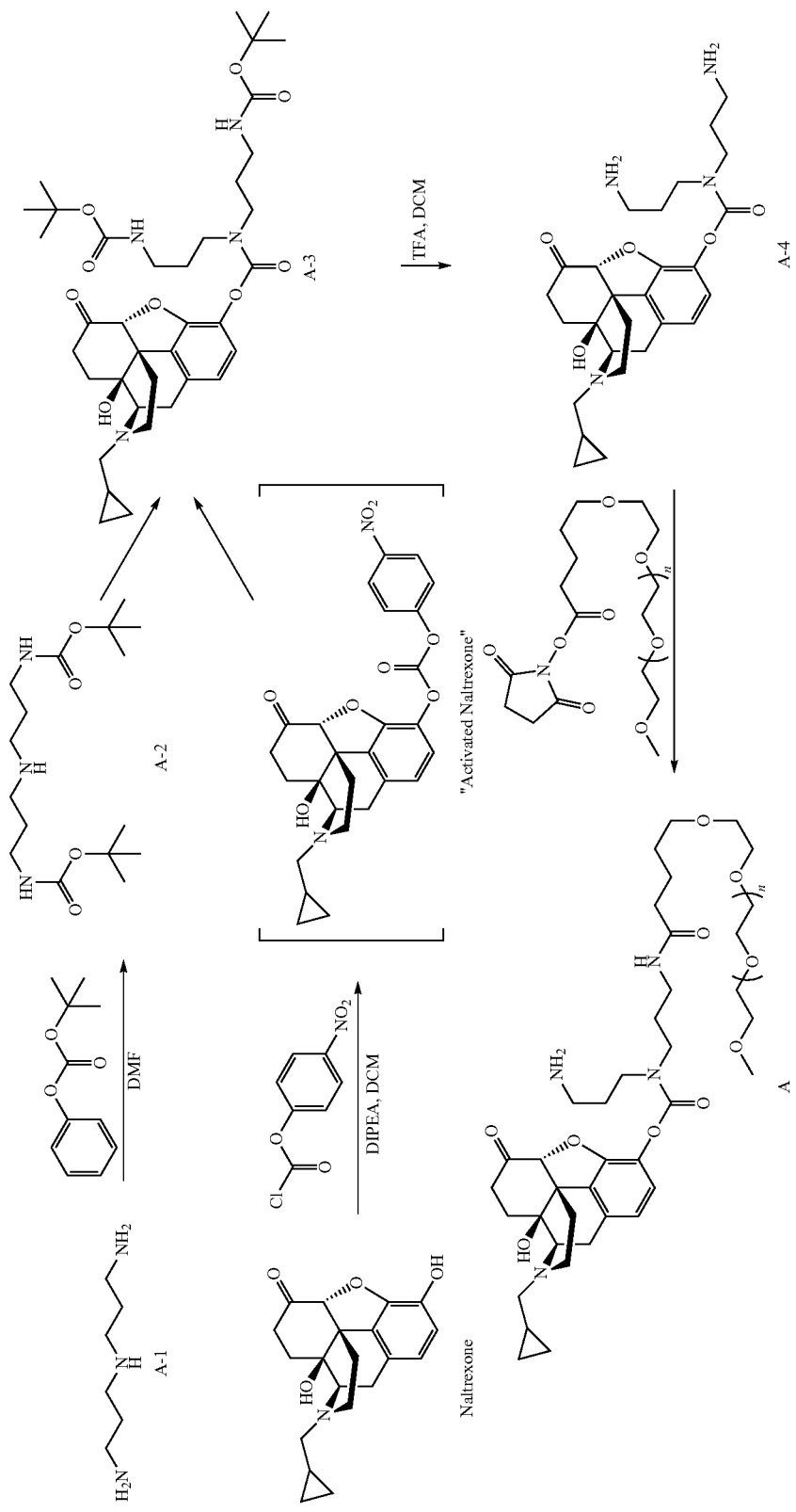

Synthesis of compound A-2: Compound A-2 was prepared according to Christensen, J. B., et al, Synthesis 2002(15): 2195-2202.

Synthesis of A-5 (Activated Naltrexone): A-5 was prepared according to a protocol similar to that described in PCT Int. Appl., 2008101187, 21 Aug. 2008.

Synthesis of A-3: to a solution of A-5 (342.6 mg, 0.677 mmol) in DCM (5 mL) was added DIPEA (176 µL, 1.01 mmol), HOAt (84 mg, 0.615 mmol) and finally A-2 (203 mg, 0.615 mmol). The reaction was allowed to stir at room temperature for 18 h. The reaction was diluted with EtOAc (20 mL) and extracted with water (20 mL), saturated $Na_2CO_3$ (3×20 mL), 1N HCl (2×20 mL) and brine (20 mL). The organic layer was dried over $MgSO_4$, filtered and concentrated to provide compound A-3 (420 mg (crude), 0.677 mmol). LC-MS [M+H] 698.6 ($C_{37}H_{54}N_4O_9$+H, calc: 698.39). Compound A-3 was used without further purification.

Synthesis of A-4: to a solution of A-3 (420 mg, 0.677 mmol) in DCM (5 mL) was added TFA (2.5 mL). The reaction was allowed to stir for 1 h at room temperature. The reaction was then condensed, taken up in water (5 mL) and purified by preparative HPLC to provide the TFA salt of compound A-4 (368 mg (3×TFA salt, 0.438 mmol). LC-MS [M+H] 499.3 ($C_{27}H_{38}N_4O_5$+H, calc: 498.28).

Synthesis of A: to a solution of A-4 (324 mg, 0.38 mmol) and mPEG-SVA (800 mg, 0.40 mmol, MW: 2000, Laysan Bio) in DMF (5 mL) was added DIPEA (205 µL, 1.14 mmol). The reaction was stirred for exactly 12 min at room temperature and then quenched with TFA (2 mL) to afford an approximate statistical mixture of starting material, mono-PEGylated and bis-PEGylated products were obtained. The desired product A was obtained via preparative HPLC to provide the TFA salt of compound A (582 mg, 0.216 mmol).

Example 9: Synthesis of Compound B

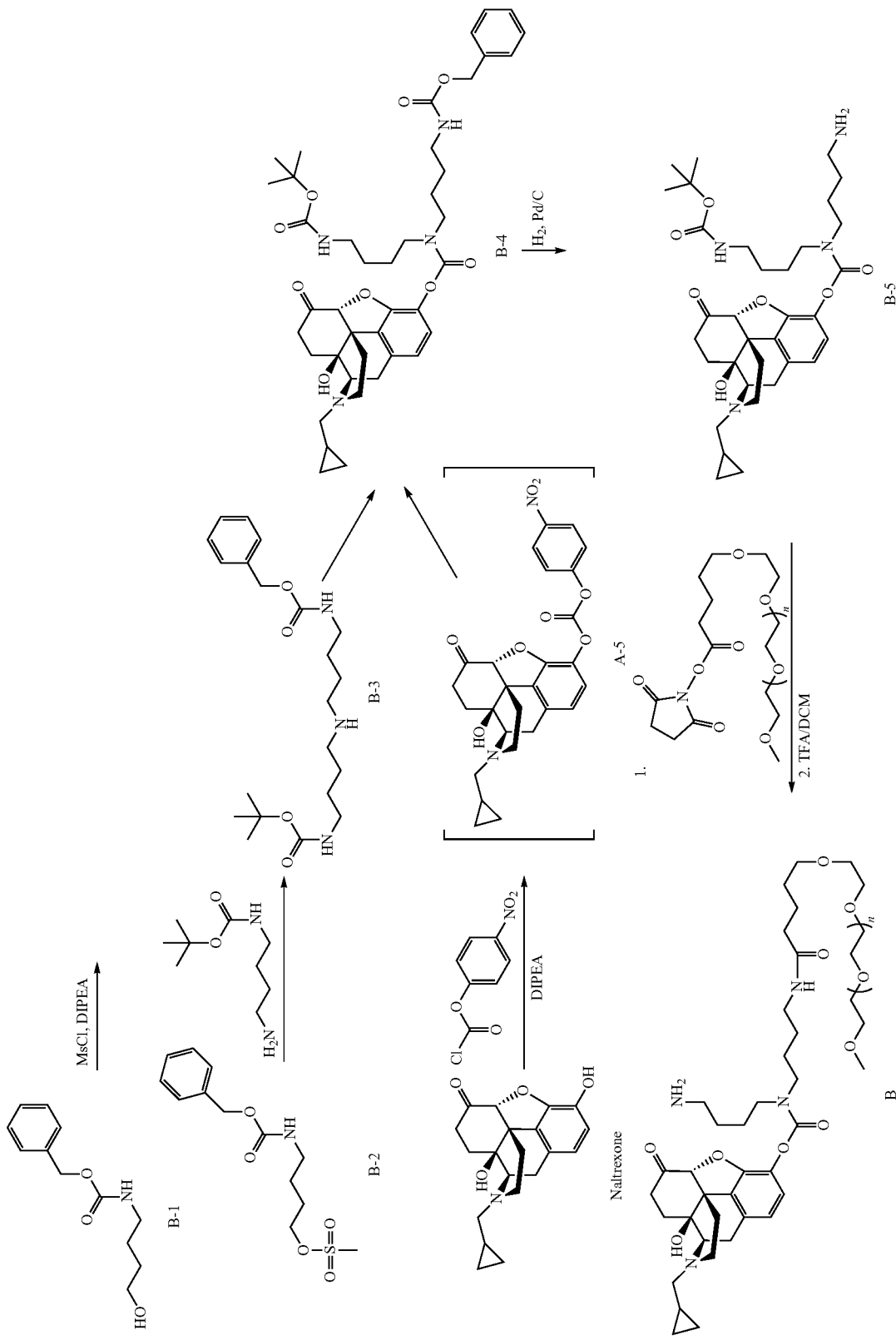

Synthesis of compound B-2: compound B-2 was prepared from B-1 according to Miller, Andrew David et al, PCT Int. Appl., 9745442, 4 Dec. 1997.

Synthesis of compound B-3: to a solution of B-2 (6.38 g, 21.2 mmol) in EtOH (100 mL) was added 1-amino-4-[(tert-butoxycarbonyl)amino]butane (4.0 g, 21.2 mmol) and DIPEA (11.1 mL, 63.6 mmol). The reaction was heated to 50° C. for 2 days. The reaction was then cooled to room temperature, condensed and purified by silica gel chromatography (MeOH/DCM) to afford compound B-3 (4.92 g, 12.5 mmol). LC-MS [M+H] 394.1 ($C_{21}H_{35}N_3O_4$+H, calc: 393.52).

Synthesis of compound B-4: to a solution of A-5 (3.80 g, 7.5 mmol) in DCM (60 mL) was added DIPEA (1.3 mL, 7.5 mmol), HOAt (1.12 g, 8.25 mmol) and finally B-3 (3.25 g, 8.25 mmol). The reaction was allowed to stir at 40° C. for 18 h. The reaction was diluted with EtOAc (200 mL) and extracted with water (200 mL), saturated $Na_2CO_3$ (3×200 mL), 1N HCl (2×200 mL) and brine (200 mL). The organic layer was dried over $MgSO_4$, filtered, concentrated and purified by silica gel chromatography (MeOH/DCM) to afford compound B-4 (2.89 g, 12.5 mmol). LC-MS [M+H] 761.4 ($C_{42}H_{56}N_4O_9$+H, calc: 760.40).

Synthesis of B-5: to a solution of B-4 (1.25 g, 1.642 mmol) in 5:1 EtOH/HOAc (25 mL/5 mL) was added $Pd(OH)_2$ (10% on carbon, 0.125 g). Next, hydrogen gas was introduced via balloon. The reaction was allowed to stir for 1 h at room temperature. The reaction was then condensed to afford compound B-5 as the HOAc salt (1.11 g (2×HOAc salt, 0.438 mmol). LC-MS [M+H] 627.2 ($C_{34}H_{50}N_4O_7$+H, calc: 626.37).

Synthesis of B: to a solution of B-5 (1.07 g, 1.71 mmol) and mPEG-SVA (3.6 g, 1.8 mmol, MW: 2000, Laysan Bio) in DMF (20 mL) was added DIPEA (892 µL, 5.13 mmol). The reaction was stirred for 1 h at room temperature. Next, the reaction mixture was condensed and dissolved in DCM (15 mL). To the reaction mixture was added TFA (5 mL) and the reaction was allowed to stir for 1 h at room temperature. The desired product B was obtained via preparative HPLC (ACN/Water) to provide the TFA salt of compound B (1.83 g (2×TFA salt), 0.677 mmol).

Example 10: Synthesis of Compound C

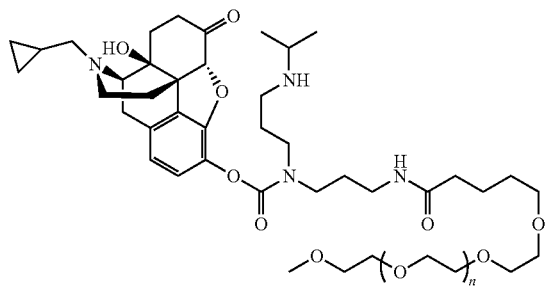

Compound C was prepared according to the procedure for compound B, except for the substitution of B-1 with benzyl N-(3-hydroxypropyl)-N-(propan-2-yl)carbamate and the substitution of 1-amino-4-[(tert-butoxycarbonyl)amino]butane with tert-butyl 3-aminopropyl(isopropyl)carbamate.

Example 11: Synthesis of Compound D

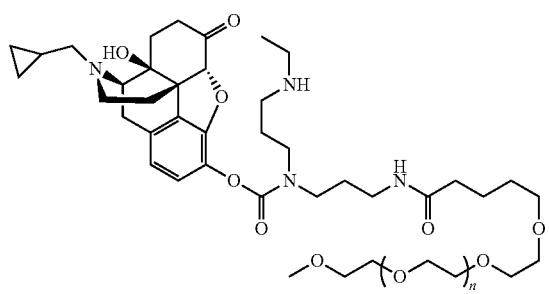

Compound D was prepared according to the procedure for compound B, except for the substitution of B-1 with benzyl N-(3-hydroxypropyl)-N-(propan-2-yl)carbamate and the substitution of 1-amino-4-[(tert-butoxycarbonyl)amino]butane with tert-butyl 3-aminopropyl(ethyl)carbamate.

Example 12: In Vitro Conversion Data for Compound a, Compound B, Compound C, and Compound D This example describes in vitro conversion data for Compound A, Compound B, Compound C, and Compound D. Compounds A, B, C, and D were prepared as previously described. In vitro conversion data for Compound A, Compound B, Compound C, and Compound D were determined by incubating the compounds in aqueous buffered solutions at the defined values for pH and temperature shown in TABLE 1, followed by LC/MS analysis.

TABLE 1

| Compound A NTX release profile | | | Compound B NTX release profile | | | Compound C NTX release profile | | | Compound D NTX release profile | | |
|---|---|---|---|---|---|---|---|---|---|---|---|
| Ph | Temp °C. | Half-life (days) | Ph | Temp °C. | Half-life (days) | Ph | Temp °C. | Half-life (days) | Ph | Temp °C. | Half-life (days) |
| 8.5[a] | 40 | 0.41 | 8.5[a] | 40 | >>60 | 8.5[a] | 40 | 15 | 8.5[a] | 40 | 1.0 |
| 7.4[b] | 37 | 2.3 | | | | | | | 7.4[b] | 37 | 6.4 |

Example 13: In Vitro Screening of PEG-NTX Polymer Conjugates

This example describes in vitro screening experiments of PEG-NTX polymer conjugates with the molecular structures shown in TABLE 2:

Molecular structures of Compound E, Compound F, and Compound A:

TABLE 2

| Compound | Molecular Structure |
|---|---|
| Compound E | 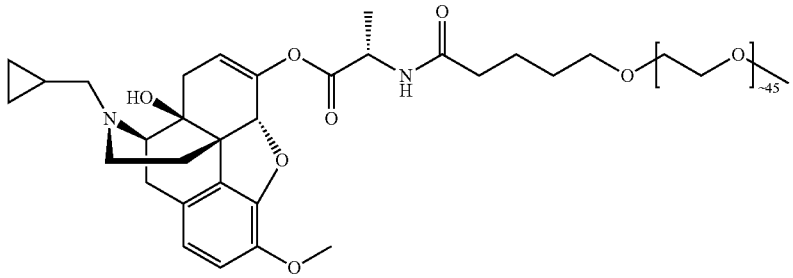 |
| Compound F | 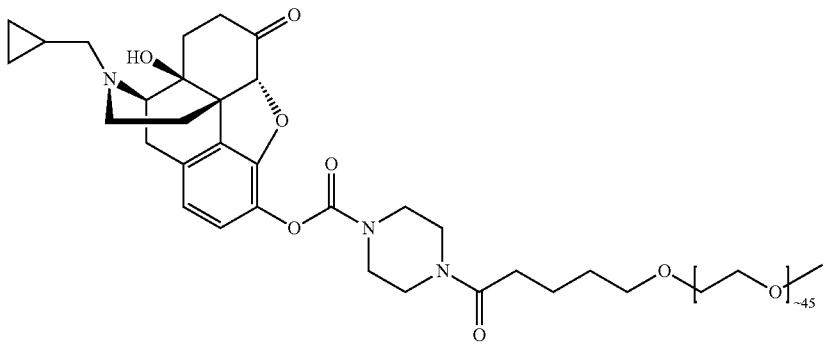 |
| Compound A | 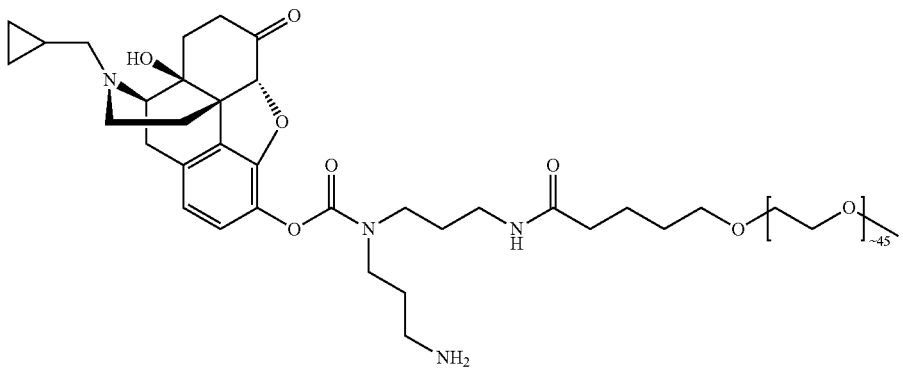 |

Several chemotypically distinct compounds, namely Compound E, Compound F, and Compound A, were evaluated in a series of in vitro studies. The in vitro assays and respective rationales for the experiments conducted with select PEG-naltrexone conjugates are shown on TABLE 3.

TABLE 3

| In Vitro Assay | Rationale |
|---|---|
| Chemical stability in representative buffered PEG400 gelcap solutions | To assess and optimize the half-life of naltrexone release from PEG-naltrexone conjugate in representative buffered gelcap formulations |
| Chemical stability in simulated gastric fluid (SGF) | To assess risk of undesired release of NTX from the NTX-polymer conjugate in the stomach |

TABLE 3-continued

| In Vitro Assay | Rationale |
| --- | --- |
| Chemical stability in simulated intestinal fluid (SIF) | To assess risk of undesired release of NTX from the NTX-polymer conjugate in the small intestine |
| Solid-State chemical stability | To assess risk of undesired release of NTX from the NTX-polymer conjugate in the solid-state following prolonged storage under ambient humidity at room temperature |
| Chemical stability in human whole blood & human liver microsome preparations | To assess the rate and extent of naltrexone release from the NTX-polymer conjugate in the systemic circulation in man |

Methods & Data Analyses:

Chemical stability in PEG400 gelcap solutions: The study compounds were incubated in 1:1 (v/v) PEG400/Aqueous 10 mM citrate buffer systems at a final concentration of 20 mg/mL. The pH was controlled by the addition of aqueous solutions of 10 mmol citric acid/trisodium citrate buffers systems. Prior to the incubations, the pH of the buffer solutions was confirmed using multi-panel pH indicator strips (MColorpHast™ 0-14 manufactured by EMD Millipore Corp). A volume of 0.666 mL of the solutions was accurately dispensed into screw-top, clear glass vials with fitted w/Teflon lined caps, under ambient atmosphere, then parafilmed before being placed in monitored incubation ovens pre-equilibrated for 24 hours to the desired temperature. $T_0$ and subsequent time-point samples were generated by pulling 50 μL aliquots from each incubate, then diluting with 950 μL of 0.1 M aqueous HCl solution. Samples were analyzed using reverse-phase HPLC on a Beckman System Gold® instrument fitted with a $C_{18}$ 4.6×55 mm waters Xterra® column. A 2-component mobile phase system w/0.1% TFA/water and 0.1% TFA/acetonitrile was employed. Five point standard curves for NTX and MNTX were generated covering a concentration range from 2.5 mg/mL down to 0.0025 mg/mL using the same HPLC instrument and methods used for the study compounds. The percent NTX released was determined using the following equation: Observed NTX peak area/100% NTX peak area×100 (the 100% NTX peak area was determined experimentally by incubating a known mass of Compound A as described below in TABLE 6). Half-lives were calculated by the following formula:

$$N(t) = N_0 (½)^{t/½}$$

Wherein: N(t)=the quantity that still remains after time t; $N_0$=the initial quantity of the substance; $t_{1/2}$=the half-life.

Chemical stability in simulated intestinal fluid and simulated gastric fluid (SIF & SGF): SIF buffer was prepared by combining 29.98 mg dihydrogen sodium phosphate, 1.25 mL water, 385 μL 0.2 N NaOH, 2.5 mL water, 50 mg pancreatin, and 865 μL water. SGF buffer was prepared by combining 10 mg NaCl, 16 mg pepsin, 35 μL 30% HCl in 4.965 mL water. The final pH values for the SIF and SGF preparations were confirmed to be 6.8 and <2.0, respectively using multi-panel pH indicator strips (MColorpHast™ 0-14 manufactured by EMD Millipore Corp). 50 μL of a 20 mmol stock solution of test compound was added to buffer at $T_0$. After defined time-points, 50 μL aliquots were taken and quenched with 100 μL of 0.1% formic acid in acetonitrile. The quenched aliquots were centrifuged (14K rpm) at 4° C. for 10 min. 100 μL of resulting supernatant was diluted with 700 μL of 1% aqueous formic acid, then analyzed on an Agilent 1100 HPLC system using a reverse phase $C_{18}$ 4.6×55 mm waters Xterra® column with a 2-component mobile phase system w/0.1% TFA/water and 0.1% TFA/acetonitrile. The resulting NTX or MNTX peaks were integrated and the % NTX or MNTX released from the test compounds was calculated using the following equation: Observed NTX peak area/100% NTX peak area×100 (the 100% peak area was determined experimentally by incubating a known mass of study compound as described below in TABLE 5.

Solid-State chemical stability: 0.5 g on Compound A was purified using preparative reverse phase HPLC on a Rainin dynamax SD-200 employing a 21.2 mm×250 mm" Varian Polaris 5 C18 column and a UV-vis detector (230 nm). Compound A was eluted from the column using a two component mobile phase system consisting of 0.1% TFA/water and 0.1% TFA/acetonitrile. Fractions containing isolated Compound A were collected, combined, frozen and lyophilized resulting in the isolation of the bis-TFA salt of Compound A (Compound A.2TFA) as an off-white waxy solid. A small sample (~5 mg) of solid Compound A.2TFA was placed under ambient atmosphere in a screw-top borosilicate glass vial and sealed then allowed to sit on a bench-top in the laboratory for 70 days. A small aliquot (~1 mg) was dissolved in 0.1N HCl and analyzed using reverse-phase HPLC on a Beckman System Gold® instrument fitted with a $C_{18}$ 4.6×55 mm waters Xterra® column employing a 2-component mobile phase system w/0.1% TFA/water and 0.1% TFA/acetonitrile.

Chemical stability in human whole blood & human liver microsomes (HLM): Human liver microsomes from Corning, UltraPool HLM 150, Cat #452117, Lot #38289, and Human Whole Blood (Male) from Bioreclamation IVT Cat #HMWBEDTA2-M, Lot #BRH950696 were used. For the HLM assay, the HLM containing solution was stored at −80° C. before thawing in a 37° C. water bath. After thawing, the HLM solution was kept on ice prior to dilution into the assay buffer. The concentration of human liver microsome solution was 1 mg/mL and also contained a 1 mM concentration of NADPH. Human blood was stored at 4° C. and warmed to 37° C. before the experiment. In each of the assays, Compound A was incubated at a concentration of 0.1 mg/mL. After 0, 15, 30, and 60 min samples were collected and quenched with 0.1% formic acid in acetonitrile, vortexed, centrifuged (4,000 RPM×15 mins) and the resulting supernatants were analyzed by HPLC/UV-vis using a Xbridge (Waters) column $C_{18}$, 50×2.1 mm, 3.5 micron employing a 2-component mobile phase system w/0.1% TFA/water and 0.1% TFA/acetonitrile. All incubations and analyses were conducted in duplicate. Verapamil (HLM) and eucatropine (whole blood) were used reference standards (positive controls) at a final concentration of 1 μM. An NTX standard curve using concentrations of 1, 10, 100, 1000 μg/mL was generated and used to extrapolate the amount of NTX released from Compound A during the studies. The % NTX released from the test compounds was calculated using the following equation: Observed NTX peak area/100% NTX peak area×100 (the 100% peak area was determined experimentally by incubating a known mass of Compound A as described in TABLE 6 below).

The resulting data obtained for Compound E, Compound F, and Compound A in these in vitro studies are summarized in TABLE 5.

study with Compound A (1.0 mg/mL) in an aqueous Trizma®-HCl buffer system (pH 8.5) at 37° C. was conducted. NTX release was monitored by HPLC and was determined to be complete after 24 hours of incubation. During the course of this study, the initial 1.0 mg/mL Compound A solution yielded a final concentration of 146.6 µg/mL NTX. The theoretical mass of releasable NTX from

TABLE 5

|  | Compound E | | Compound F | | Compound A | |
|---|---|---|---|---|---|---|
|  | \*Hd | Half-life (days) | \*Hd | Half-life (days) | \*Hd | Half-life (days) |
| In Vitro Assay Chemical stability in representative buffered PEG400 gelcap solutions | 6 | 12 | 8 | ∞ | 6 | 65.5 |
|  |  |  |  |  | 5.5 | 135 |
|  | 5.5 | 14 | 6 | ∞ | 5 | 256 |
|  |  |  |  |  | 4.5 | 298 |
|  | 5 | 9 | 4 | ∞ | 4 | 545 |
|  | Clean conversion to NTX with no other degradants detected by HPLC | | No detectable NTX released | | Clean conversion to NTX with no undesired degradants detected by HPLC | |
| Chemical stability in simulated gastric fluid (SGF) | 8% MNTX released | | N/A | | No NTX release detected | |
| Chemical stability in simulated intestinal fluid (SIF) | 81% MNTX released | | N/A | | 1.5 ± 0.4% NTX released | |
| Solid-State chemical stability | N/A | | N/A | | Chemically stable after 70 days at RT (No NTX release or other degradants detected) | |
| Chemical stability in human whole blood | N/A | | N/A | | 4.2 ± 0.5% NTX detected after 1 h incubation at 37° C. | |
| Chemical stability in human liver microsome preparation | N/A | | N/A | | 6.6 ± 1.7% NTX detected after 1 h incubation at 37° C. | |

*The differential pH ranges chosen for Compound E, Compound F were based on predicted hydrolytic susceptibilities of the functional groups directly linking NTX. The pH range studied for Compound A was designed to characterize the pH dependence of the cyclization-release reaction.

Example 14: Chemical Stability of Compound A

The informal chemical stability of solid-state Compound A bistrifluoroacetic acid salt (Compound A.2TFA) was evaluated under ambient conditions in the laboratory. Analytical HPLC data demonstrated no detectable release of NTX from Compound A following 70-day storage at room temperature. This robust solid-state chemical stability enables the requisite purification, handling, and storage of Compound A salts without the risk of undesired release of NTX. This ensures that the release of NTX will only commence once Compound A salts are formulated in the final gelcap dose-forms as intended. FIG. 1 is analytical HPLC data for Compound A.2TFA salt immediately following purification (see arrow pointing to Compound A) and after several months of storage under ambient conditions (note arrow pointing to the complete overlay of the 1 and 70-day HPLC traces of Compound A). Also shown in FIG. 1 is a reference trace (see arrow pointing to NTX) of NTX, which illustrates the absence of NTX following the 70-day RT storage period. Note that the small artifact peaks shown in the shaded gray were present in contemporaneous blank control injections.

Example 15: Overall Efficiency of NTX Release from Compound A Under Basic Aqueous Conditions In an effort to characterize the overall efficiency and extent of NTX release from Compound A, an incubation Compound A, 142 µg/mL, was calculated based on the relative molecular weights of Compound A and NTX. Compound A is a poly-disperse PEG2K derivative with an average molecular weight ($MW_{avg}$) of ~2,400 g/mol. The molecular weight of NTX is 341.4 g/mol, therefore Compound A is ~14.22% NTX by weight using the formula: % $NTX=MW_{NTX}MW_{Compound\ A}\times100$. Accordingly, the incubation of a 1.0 mg/mL solution of Compound A should theoretically yield a final NTX concentration of 142 µg/mL following complete release of NTX. The experimentally determined concentration of NTX following incubation of a 1 mg/mL solution of Compound A in an aqueous Trizma-HCl buffer system until the measured NTX peak area no longer increased, was 146.6 µg/mL (see Table 6 below). The parity between the experimentally determined vs. the theoretically predicted NTX release values confirms both the molecular structure of Compound A, and that the cyclization-release reaction proceeds with a very high degree of chemical efficiency. TABLE 6 shows the quantitation of NTX release from Compound A following incubation in Trizma-HCl buffer (pH 8.5) at 37° C.

TABLE 6

| Sample | NTX Peak Area | [NTX] µg/mL |
|---|---|---|
| Reference Standards | 12.8 | 1 |
|  | 120.1 | 10 |

TABLE 6-continued

| Sample | NTX Peak Area | [NTX] μg/mL |
|---|---|---|
| | 1181.3 | 100 |
| | 11424.9 | 1000 |
| Timepoints (h) | | |
| 3 | 498.2 | 43.3 |
| 6 | 807.9 | 70.4 |
| 22 | 1661.5 | 145.9 |
| 24 | 1679.0 | 146.6 |
| Theoretical NTX release | | 142 |

Method: Compound A was dissolved in Tris-HCl buffer solution at pH 8.5 at a concentration of 1 mg/ml. Aliquots pulled at the defined time-points (1, 3, 6, 22, 24 h) were quenched by diluting 10-fold with 1% formic acid in acetonitrile then analyzed by HPLC/UV-vis using a Xbridge (Waters) $C_{18}$, 50×2.1 mm, 3.5 micron column employing a 2-component mobile phase system w/0.1% TFA/water and 0.1% TFA/acetonitrile. Resulting NTX concentrations and % NTX released from Compound A were calculated from a four point standard curve spanning a concentration range of 1, 10, 100, 1000 μg/mL.

Figure 2:
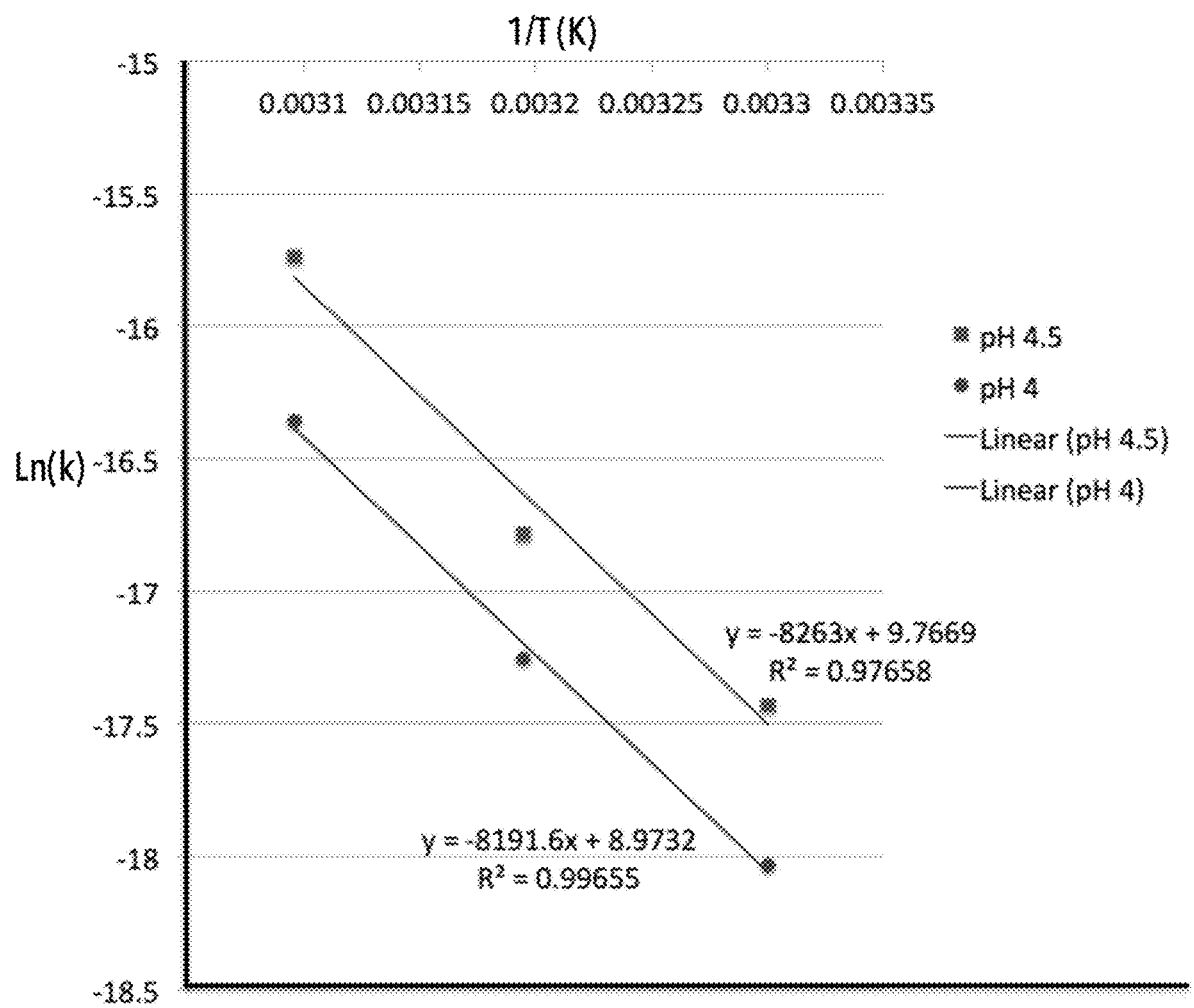
FIG. 2 illustrates the Arrhenius plots of Ln (k) vs. 1/T (K) for pH 4.5 and 4.0 citrate buffered/PEG400 incubations of Compound A conducted at 30, 40, and 50° C.

The half-life of the NTX release from Compound A in a gelcap compatible solvent system can be modulated by adjusting pH (as demonstrated in TABLE 5 (above). Further characterization of the half-life of NTX release from Compound A at pH values of 4.0 and 4.5 at temperatures of 30, 40 and 50° C. was conducted. The resulting data enabled the generation of Arrhenius plots whereby the reaction kinetics and the expected half-life of NTX release at room temperature (~20° C.) for self-expiring (auto-expiring) gelcaps buffered at both pH 4.5 and 4.0 could be extrapolated (see FIG. 2). FIG. 1 shows the Arrhenius plots of Ln (k) vs. 1/T (K) for pH 4.5 and 4.0 citrate buffered/PEG400 incubations of Compound A conducted at 30, 40, and 50° C. TABLE 7 shows the correlations between incubation period (days), pH, temperature, and half-life for NTX release (days).

TABLE 7

| Incubation Period (days) | pH | Temperature (° C.) | Half-life for NTX Release (days) |
|---|---|---|---|
| 30 | 4.5 | 50 | 54.8 |
| | | 40 | 156 |
| | | 30 | 298 |
| 37 | 4.0 | 50 | 102 |
| | | 40 | 250 |
| | | 30 | 545 |
| Extrapolated half-life for NTX release at RT | | | |
| pH 4.5 | | | 813 days |
| pH 4.0 | | | 1,409 days |

Example 16: In Vivo Data: Pharmacokinetics of NTX Following Oral Administration of Equimolar Doses of Compound a, Compound D, and NTX to Rats Study Design:

Equimolar doses (13.2 μmol/rat) of NTX, Compound A, and Compound D were orally administered to male Sprague-Dawley rats (N=5 per group) weighing approximately 250 grams at time of study. Plasma samples were collected at specified time points (0, 0.33, 0.66, 1, 1.5, 2.5, 5, 8, 24 hours). The resulting plasma samples were processed and subsequently analyzed using LC/MS to quantitate NTX concentrations.

Figure 3:
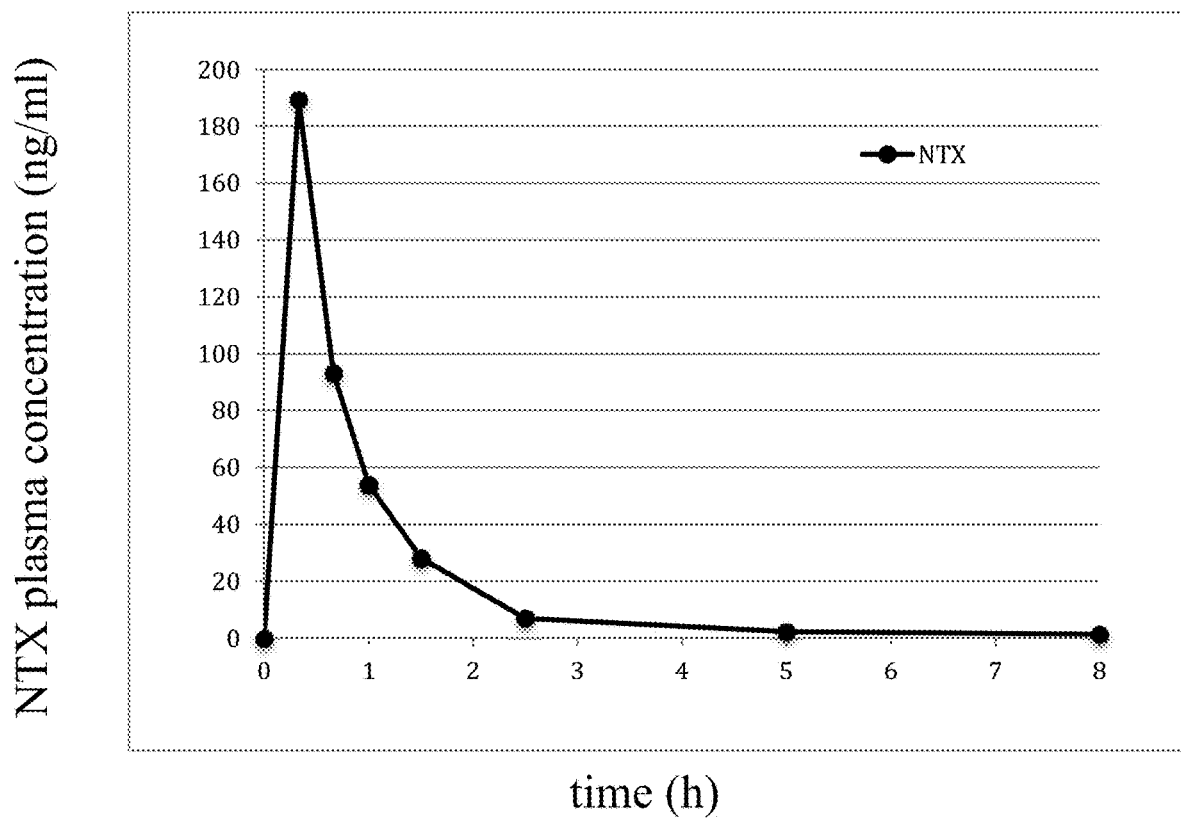
FIG. 3 illustrates the NTX plasma concentrations vs. time profiles following the oral administration of NTX.
Figure 4:
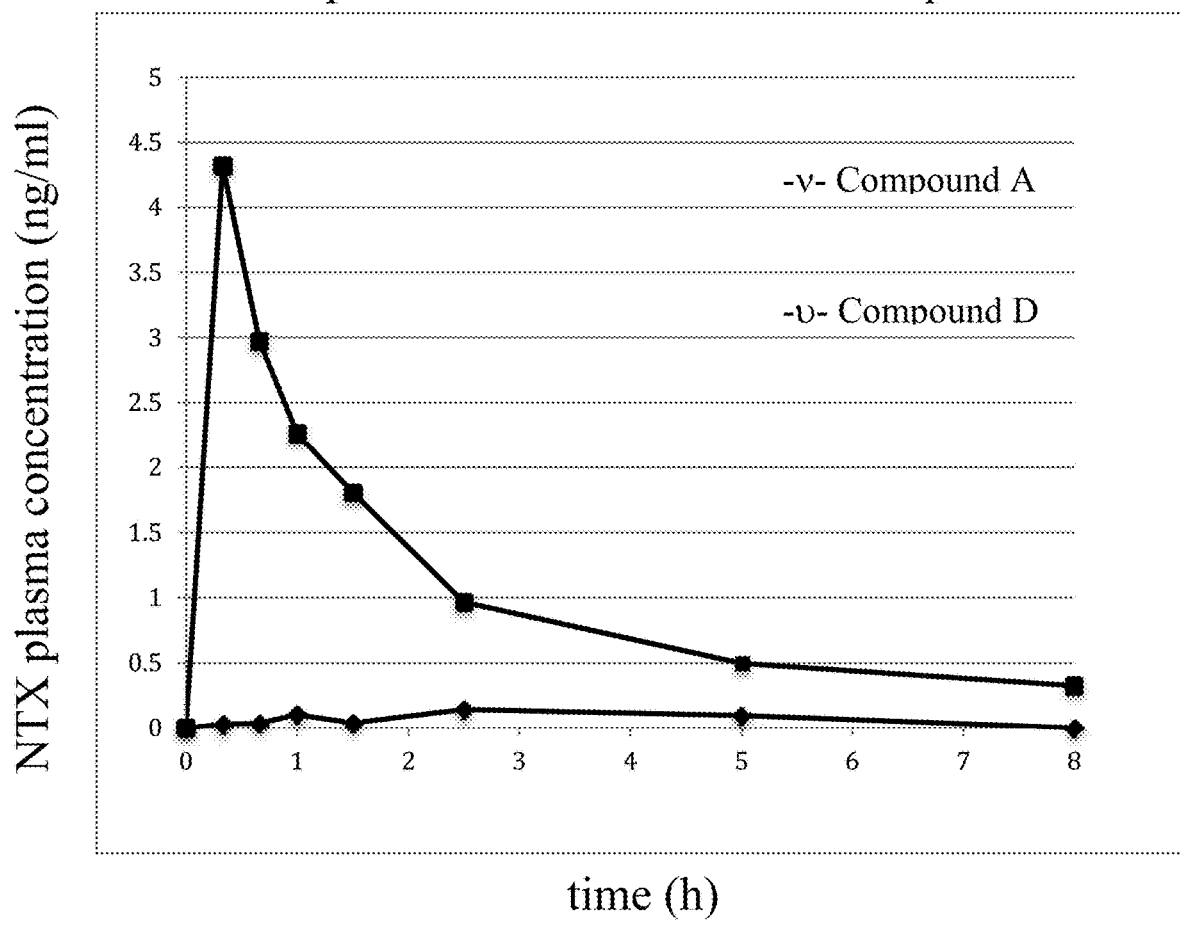
FIG. 4 illustrates the NTX plasma concentrations vs. time profiles following the oral administration of Compound A (filled squares) or Compound D (filled diamonds).

The NTX plasma concentrations vs. time profiles following the oral administration of NTX, Compound A, and Compound D are shown in FIG. 3 and FIG. 4. The data illustrates that Minimal NTX was released following oral administration of Compound A and Compound D to rats.

EMBODIMENTS

The following non-limiting embodiments provide illustrative examples of the invention, do not limit the scope of the invention.

Embodiment 1

A composition, the composition comprising: an opioid agonist; and a compound comprising formula I, (D-X—Z)$_m$—P (I), wherein D is an opioid antagonist; X is a labile functionality capable of being hydrolyzed or fragmented to release D under controlled conditions; Z is a covalent linkage between X and the polymer; P is a polymer; and m is an integer selected to be between 1 and 100,000.

Embodiment 2

The composition of claim 1, wherein the opioid agonist is morphine, hydromorphone, hydrocodone, oxycodone, codeine, levorphanol, meperidine, methadone, oxymorphone, dihydrocodeine, tramadol, pharmaceutically acceptable salts thereof, prodrugs thereof or mixtures thereof.

Embodiment 3

The composition of Embodiment 1, wherein D is naltrexone, naloxone, nalmephene, cyclazocine, levallorphan, buprenorphine, derivatives thereof, or mixtures thereof.

Embodiment 4

The composition of any one of Embodiments 1 and 2, wherein the agonist and the antagonist are present in a ratio of about 1:5 to about 1:0.001.

Embodiment 5

The composition of any one of Embodiments 1 and 2, wherein the agonist and the antagonist are present in a ratio of about 1:1 to about 1:0.001.

Embodiment 6

The composition of any one of Embodiments 1 and 2, wherein the agonist and the antagonist are present in a ratio of about 1:0.5 to about 1:0.05.

Embodiment 7

The composition of any one of Embodiments 1-6, the composition further comprising a reactive agent capable of mediating the release of the opioid antagonist from the compound comprising formula (I).

Embodiment 8

The composition of Embodiment 7, wherein the reactive agent is water, an alcohol, an organic or inorganic base, an organic or inorganic acid, a Lewis acid or base, a nitrogen- or sulfur- or oxygen-based nucleophile, or an amine.

Embodiment 9

The composition of Embodiment 8, wherein the amine is an amino acid or a peptide.

Embodiment 10

The composition of any one of Embodiments 1-9, wherein the amino acid comprises alanine, arginine, asparagine, aspartic acid, cysteine, glycine, glutamine, glutamic acid, histidine, isoleucine, leucine, methionine, phenylalanine, proline, serine, threonine, tryptophan, tyrosine, lysine, valine, a dipeptide thereof, a tripeptide thereof, or a combination thereof.

Embodiment 11

The composition of any one of Embodiments 1-10, wherein the polymer is of low (oligomeric), medium, or high molecular weight and comprises polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polysaccharides, or combinations thereof.

Embodiment 12

The composition of any one of Embodiments 1-10, wherein the polymer comprises polyethylene glycol (PEG), poly(lactide-co-glycolide) (PLGA), polylactide (PLA), polyglycolide (PGA), or a polycaprolactone.

Embodiment 13

A liquid dose form comprising: an effective amount of an opioid agonist; an opioid antagonist-polymer conjugate; a pharmaceutically acceptable liquid carrier; and an optional reactive agent capable of hydrolyzing the opioid antagonist-polymer conjugate of formula (I).

Embodiment 14

A liquid dose form of Embodiment 13, wherein the agonist is morphine, hydromorphone, hydrocodone, oxycodone, codeine, levorphanol, meperidine, methadone, oxymorphone, dihydrocodeine, tramadol, pharmaceutically acceptable salts thereof, prodrugs thereof or mixtures thereof.

Embodiment 15

The liquid dose form of any one of Embodiments 13 and 14, wherein the reactive agent is water, an alcohol, an amine, a thiol, or an amino acid.

Embodiment 16

The liquid dose form of Embodiments 13-14, wherein the reactive agent is a buffer, a Lewis acid or a Lewis base.

Embodiment 17

A liquid-filled dose form comprising a sheath enclosing a liquid fill, the fill comprising: an effective amount of an opioid agonist; an opioid antagonist-polymer conjugate of formula (I); a pharmaceutically acceptable liquid carrier; and an optional reactive agent capable of hydrolyzing the opioid antagonist-polymer conjugate.

Embodiment 18

A liquid-filled dose form of Embodiment 17, wherein the agonist is morphine, hydromorphone, hydrocodone, oxycodone, codeine, levorphanol, meperidine, methadone, oxymorphone, dihydrocodeine, tramadol, pharmaceutically acceptable salts thereof, prodrugs thereof or mixtures thereof.

Embodiment 19

The liquid-filled dose form of any one of Embodiments 17 and 18, wherein the reactive agent is water, an alcohol, an amine, a thiol, or an amino acid.

Embodiment 20

The liquid-filled dose form of Embodiments 17 and 18, wherein the reactive agent is a buffer, a Lewis acid or a Lewis base.

Embodiment 21

A solid dose form comprising: an effective amount of an opioid agonist; an opioid antagonist-polymer conjugate of formula (I); an optional reactive agent capable of hydrolyzing the opioid antagonist-polymer conjugate; and one or more acceptable pharmaceutical excipients used for solid dose forms.

Embodiment 22

A solid dose form of Embodiment 21, wherein the agonist is morphine, hydromorphone, hydrocodone, oxycodone, codeine, levorphanol, meperidine, methadone, oxymorphone, dihydrocodeine, tramadol, pharmaceutically acceptable salts thereof, prodrugs thereof or mixtures thereof.

Embodiment 23

The solid dose form of any one of Embodiments 21 and 22, wherein the reactive agent is water, an alcohol, an amine, a thiol, or an amino acid.

Embodiment 24

The solid dose form of Embodiments 21 and 22, wherein the reactive agent is a buffer, a Lewis acid or a Lewis base.

Embodiment 25

The solid dose form composition of any of embodiments 21-24 whereby the solid dose form provides short-acting analgesia (i.e. rapid release of the opioid agonist) following oral ingestion by a subject.

Embodiment 26

The solid dose form composition of any of embodiments 21-24 whereby the solid dose form provides long-acting analgesia (i.e. extended release of the opioid agonist) following oral ingestion by a subject.

Embodiment 27

A dose unit form for use in treating a condition, wherein the dose unit form comprises: i) an opioid agonist; ii) a opioid antagonist-polymer conjugate, wherein the polymer-opioid antagonist releases or hydrolyzes an amount of an opioid antagonist after a period of time.

Embodiment 28

A dose unit form for use in treating a condition, wherein the dose unit form comprises: i) an opioid agonist; ii) a opioid antagonist-polymer conjugate, wherein the opioid antagonist-polymer conjugate liberates an amount of an opioid antagonist over a period of time.

Embodiment 29

The dose unit form of any one of Embodiments 27 and 28, wherein the opioid antagonist-polymer conjugate is a compound of formula I, $(D-X—Z)_m—P$ (I), wherein D is an opioid antagonist; X is a labile functionality capable of being hydrolyzed or fragmented to release D under controlled conditions; Z is a covalent linkage between X and the polymer; P is a polymer; and m is an integer selected to be between 1 and 100,000.

Embodiment 30

A method for providing analgesia to a subject in need thereof, the method comprising administrating to the subject a dose unit form comprising: i) an opioid agonist; and ii) a opioid antagonist-polymer conjugate; wherein the opioid antagonist-polymer conjugate provides an opioid antagonist at a rate that attenuates the pharmacodynamic effects of the opioid agonist over a period of time.

Embodiment 31

A method for providing analgesia to a subject in need thereof, the method comprising administrating to the subject a dose unit form comprising: i) an opioid agonist; and ii) a polymer-opioid antagonist conjugate; wherein the polymer-opioid antagonist conjugate provides an opioid antagonist at a rate that limits the therapeutic efficacy of the opioid agonist to a first period of time.

Embodiment 32

The method of any one of Embodiments 30 and 31, wherein the therapeutically-effective plasma level of the opioid agonist is from about 10 pg/mL to about 1,000 ng/mL.

Embodiment 33

The method of any one of Embodiments 30 and 31, wherein the therapeutically-effective plasma level of the opioid agonist is from about 0.5 ng/mL to about 500 ng/mL.

Embodiment 34

The method of any one of Embodiments 30 and 31, wherein the therapeutically-effective plasma level of the opioid agonist is from about 0.1 ng/mL to about 100 ng/mL.

Embodiment 35

The method of any one of Embodiments 30-34, wherein the first period of time is up to 3 months.

Embodiment 36

The method of any one of Embodiments 30-34, wherein the first period of time is up to 6 months.

Embodiment 37

The method of any one of Embodiments 30-34, wherein the first period of time is up to 9 months.

Embodiment 38

The method of any one of Embodiments 30-34, wherein the first period of time is up to 12 months.

Embodiment 39

The method of any one of Embodiments 30-38, wherein the opioid agonist is morphine, hydromorphone, hydrocodone, oxycodone, codeine, levorphanol, meperidine, methadone, oxymorphone, dihydrocodeine, tramadol, pharmaceutically acceptable salts thereof, prodrugs thereof or mixtures thereof.

Embodiment 40

The method of any one of Embodiments 30-39, wherein the opioid antagonist is naltrexone, naloxone, nalmephene, cyclazocine, levallorphan, buprenorphine, derivatives thereof, or mixtures thereof.

Embodiment 41

The method of any one of Embodiments 30-40, wherein the agonist and the antagonist are present in a ratio of about 1:5 to about 1:0.001.

Embodiment 42

The method of any one of Embodiments 30-40, wherein the agonist and the antagonist are present in a ratio of about 1:1 to about 1:0.001.

Embodiment 43

The method of any one of Embodiments 30-40, wherein the agonist and the antagonist are present in a ratio of about 1:0.5 to about 1:0.05.

Embodiment 44

A pharmaceutical composition comprising: an effective amount of an opioid agonist; an opioid antagonist-polymer conjugate; a pharmaceutically acceptable liquid carrier; and an optional reactive agent capable of mediating the release of the opioid antagonist from the opioid antagonist-polymer conjugate.

Embodiment 45

A liquid-filled capsule comprising a sheath enclosing a liquid fill, the fill comprising: an effective amount of an opioid agonist; an opioid antagonist-polymer conjugate; a pharmaceutically acceptable liquid carrier; and a reactive agent capable of mediating the release of the opioid antagonist from the opioid antagonist-polymer conjugate.

Embodiment 46

A pharmaceutical composition comprising: an effective amount of an opioid agonist; an opioid antagonist-polymer conjugate; one or more pharmaceutically acceptable excipients a reactive agent capable of mediating the release of the opioid antagonist from the opioid antagonist-polymer conjugate.

Embodiment 47

A composition comprising: an effective amount of an opioid agonist; a polymer-opioid antagonist conjugate capable of releasing an opioid antagonist at a defined rate; pharmaceutically acceptable excipient(s).

Embodiment 48

A oral pharmaceutical composition comprising: an effective amount of an opioid agonist; a polymer-opioid antagonist conjugate capable of releasing an opioid antagonist at a defined rate; and a pharmaceutically acceptable liquid carrier.

The invention claimed is:
1. A method for providing analgesia to a subject in need thereof, the method comprising administrating to the subject a dose unit form comprising:
 i) an opioid agonist; and
 ii) an opioid antagonist-polymer conjugate according to formula (I),

wherein D is independently at each occurrence an opioid antagonist, or pharmaceutically acceptable salts thereof, and mixtures thereof;
X forms a labile functionality between D and Z defined by:

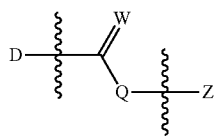

that reacts, by cyclization-release mediated by a tethered nucleophile on Q in an intramolecular reaction with the carbon atom bearing Q and W, within a dose-unit form to release D, wherein:
W is independently at each occurrence O, S, NH, or $NR^1$, and $R^1$ is independently selected at each occurrence from the group consisting of hydrogen, alkyl, aryl, and heteroaryl;
Q is independently at each occurrence NH, NR or CR'R", where R is the tethered nucleophile, where R' and R" are independently selected at each occurrence from the group consisting of hydrogen, alkyl, aryl, heteroaryl, and the tethered nucleophile, and where at each occurrence of CR'R" at least one of R' and R" is the tethered nucleophile;
Z is independently at each occurrence a covalent linkage between X and a polymer, P, wherein Z is a direct bond, an alkyl amine, an oxygen atom, a sulfur atom, a substituted amine, an alkyl group, a cyclo-alkyl group, a heteroalkyl group, an aryl group, or an amino acid, wherein the alkyl amine, the alkyl group, the cyclo-alkyl group, the heteroalkyl group, the aryl group, or the amino acid is optionally substituted with the tethered nucleophile;
P is the polymer;
and m is an integer from 1 to 100,000;
wherein the opioid antagonist-polymer conjugate provides an opioid antagonist at a rate that attenuates the pharmacodynamic effects of the opioid agonist over a period of time, and wherein the opioid antagonist-polymer conjugate provides the opioid antagonist at least within the dose unit form.

2. The method of claim 1, wherein a therapeutically-effective plasma level of the opioid agonist is from about 10 pg/mL to about 1,000 ng/mL.

3. The method of claim 2, wherein the therapeutically-effective plasma level of the opioid agonist is from about 0.5 ng/mL to about 500 ng/mL.

4. The method of claim 2, wherein the therapeutically-effective plasma level of the opioid agonist is from about 0.1 ng/mL to about 100 ng/mL.

5. The method of claim 1, wherein the opioid agonist is morphine, hydromorphone, hydrocodone, oxycodone, codeine, levorphanol, meperidine, methadone, oxymorphone, dihydrocodeine, tramadol, pharmaceutically acceptable salts thereof, prodrugs thereof or mixtures thereof.

6. The method of claim 1, wherein the opioid antagonist is naltrexone, naloxone, nalmephene, cyclazocine, levallorphan, buprenorphine, derivatives thereof, or mixtures thereof.

7. The method of claim 1, wherein the opioid agonist and the opioid antagonist are present in a molar ratio of from about 1:10 to about 1:0.001.

8. The method of claim 1, wherein the opioid agonist and the opioid antagonist are present in a molar ratio of about 1:1 to about 1:0.001.

9. The method of claim 1, wherein the opioid agonist and the opioid antagonist are present in a molar ratio of about 1:0.5 to about 1:0.05.

10. The method of claim 1, wherein the opioid antagonist-polymer conjugate provides the opioid antagonist at a rate that limits a therapeutically-effective plasma level of the opioid agonist to a first period of time from a time of manufacture.

11. The method of claim 10, wherein the therapeutically-effective plasma level of the opioid agonist is from about 10 pg/mL to about 1,000 ng/mL, from about 0.5 ng/mL to about 500 ng/mL, or from about 0.1 ng/mL to about 100 ng/mL.

12. The method of claim 10, wherein the first period of time is up to 3 months, the first period of time is up to 6 months, the first period of time is up to 9 months, the first period of time is up to 12 months, the first period of time is up to 18 months, the first period of time is up to 24 months, or the first period of time is up to 36 months.

13. The method of claim 1, wherein the opioid antagonist-polymer conjugate provides the opioid antagonist via a kinetically controlled intramolecular cyclization-release reaction.

14. The method of claim 13, wherein a tethered nucleophile capable of mediating cyclization-release of the opioid antagonist is an amine.

15. The method of claim 14, wherein the amine is a primary or a secondary amine.

16. The method of claim 14, wherein the amine is a primary amine.

17. The method of claim 14, wherein the amine is a secondary amine.

18. The method of claim 1, wherein the opioid agonist and the opioid antagonist-polymer conjugate are present in the dose unit form at a time of manufacture in a molar ratio of from about 20:1 to about 1:1, a molar ratio of about 10:1 to about 1:1, a molar ratio of about 5:1 to about 1:1, or a molar ratio of about 10:1 to about 5:1.

19. The method of claim 1, wherein the dose unit form is a tablet, a capsule, a soft gelatin capsule, a hard gelatin capsule, a suspension, or a liquid.

20. The method of claim 19, wherein the dose unit form is a soft gelatin capsule, a suspension, or a liquid.

21. The method of claim 1, wherein the compound according to formula (I) is:

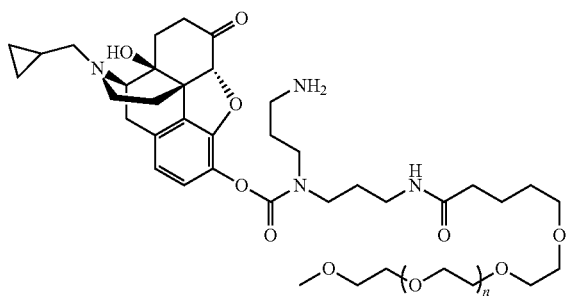

or a pharmaceutically acceptable salt thereof, and n is about 39.

22. The method of claim 1, wherein the compound according to formula (I) is:

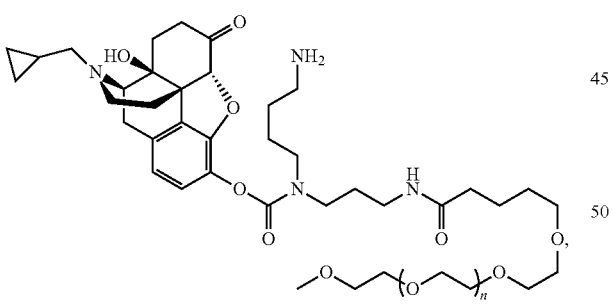

or a pharmaceutically acceptable salt thereof, and n is about 39.

23. The method of claim 1, wherein the compound according to formula (I) is:

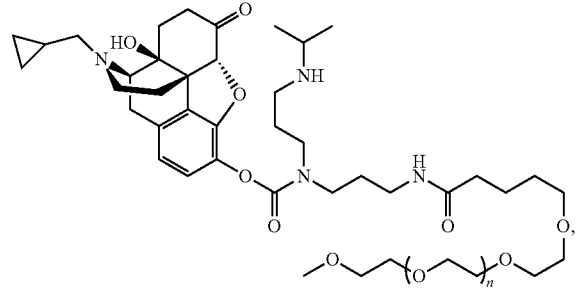

or a pharmaceutically acceptable salt thereof, and n is about 39.

24. The method of claim 1, wherein the compound according to formula (I) is:

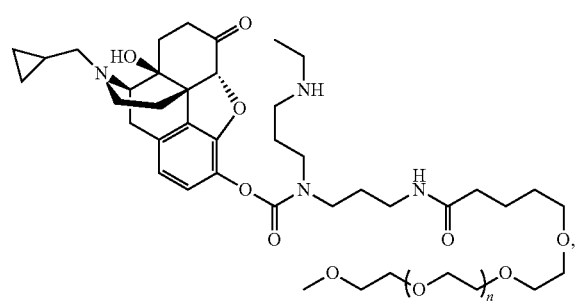

or a pharmaceutically acceptable salt thereof, and n is about 39.

* * * * *